(12) United States Patent
Nakamura et al.

(10) Patent No.: US 8,053,628 B2
(45) Date of Patent: Nov. 8, 2011

(54) WHEAT HAVING NEW STARCH AND METHOD FOR PRODUCING IT

(75) Inventors: Toshiki Nakamura, Iwate (JP); Mika Saito, Iwate (JP); Patricia Lynn Vrinten, Saskatchewan (CA); Junichi Yonemaru, Iwate (JP); Goro Ishikawa, Iwate (JP); Tomoya Shinbata, Kanagawa (JP); Hideyo Yasuda, Kanagawa (JP); Yasuhiro Seto, Kanagawa (JP); Youichi Kurimoto, Kanagawa (JP); Yoshikazu Ishihara, Kanagawa (JP)

(73) Assignees: Nippon Flour Mills Co., Ltd., Tokyo (JP); Incorporated Administrative Agency National Agriculture and Food Research Organization, Ibaraki (JP)

( * ) Notice: Subject to any disclaimer, the term of this patent is extended or adjusted under 35 U.S.C. 154(b) by 857 days.

(21) Appl. No.: 11/913,263

(22) PCT Filed: May 2, 2006

(86) PCT No.: PCT/JP2006/309152
§ 371 (c)(1),
(2), (4) Date: Oct. 31, 2007

(87) PCT Pub. No.: WO2006/118300
PCT Pub. Date: Nov. 9, 2006

(65) Prior Publication Data
US 2009/0285960 A1     Nov. 19, 2009

(30) Foreign Application Priority Data

May 2, 2005   (JP) ................................ 2005-134614
Feb. 20, 2006 (JP) ................................ 2006-042843

(51) Int. Cl.
*A01H 5/00*    (2006.01)
*A01H 1/00*    (2006.01)
*C12N 9/00*    (2006.01)

(52) U.S. Cl. ..................... 800/263; 800/278; 800/320.3; 435/183; 435/410

(58) Field of Classification Search .......................... None
See application file for complete search history.

(56) References Cited

U.S. PATENT DOCUMENTS

2002/0037352 A1   3/2002   Messager et al.
2003/0200581 A1  10/2003   Yamamori

FOREIGN PATENT DOCUMENTS

| EP | 0864258 A1 | 9/1998 |
| JP | 06125669 | 5/1994 |
| JP | 2004015390 | 1/2004 |
| WO | 0058366 | 10/2000 |

OTHER PUBLICATIONS

Yamamori et al 2000 Theor Appl Genet 100:32-38, provided in Applicant IDS.*
Yamamori et al 1 2000 Theor Appl Genet 100:32-38, provided by Applicant.*
Yamamori et al 2 2000 Theor Appl Genet 101:21-29, provided by Applicant.*
Jobling et al 2002 Nature Biotechnology 20:295-299.*
Chinese Office Action issued on Dec. 18, 2009.
Kiribuchi-Otobe et al.; Genetic Analysis and Some Properties of Starch in Waxy Mutant Wheat Tanikei A-6599-4; Breeding Science, vol. 51, No. 4, Dec. 2001, pp. 241-245.
Hoshino et al.; Development of Waxy Common Wheat by Haploid Breeding; Breeding Science; vol. 46, No. 2, Jan. 1, 1996, pp. 185-188.
Fujita et al.; The isolation and characterization of a waxy mutant of diploid wheat (*Triticum monococcum* L.); Plant Science, Elsevier Ireland, Ltd., IE, vol. 160, No. 4, Mar. 1, 2001, pp. 595-602.
Miura et al.; Development of near-isogenic lines of wheat carrying different null Wx alleles and their starch properties; Euphytica, vol. 123, No. 3, 2002, pp. 353-359.
Kim et al.; Thermostable, Raw-Starch-Digesting Amylase from *Bacillus-stearothermophilus*; Applied and Environmental Microbiology, vol. 55, No. 6, 1989, pp. 1638-1639.
Ugalde et al.; Substrate Gradients and Regional Patterns of Dry Matter Deposition Within Developing Wheat Endosperm, I. Carbohydrates; Australian Journal of Plant Physiology, vol. 17, No. 4, 1990, pp. 377-394.
Sebecic et al.; Wheat flour starch granule-size distribution and rheological properties of dough, Part I. Granulometric analysis of starch; Nahrung, vol. 39, No. 2, 1995, pp. 106-116.
Annex Q9SQ52_TRIMO; Nucleotide Sequence; "The genes encoding granule-bound starch synthases at the waxy loci of the A, B and D progenitors of common wheat."Yan, et al. (1999.).
Annex Q5NKR2_TRIMO, Nucleotide Sequence, "Comparative sequence analysis of homologous Wx1 regions in barley, maize, pearl millet, rice, sorghum and diploid wheat." Ma, et al. (Feb. 2002.).
European Office Action for 06 746 002.2-1212 dated Jan. 11, 2010.
Tohoku Nogyo Shiken Kenkyu Suishin Kaigi, Novel granule bound starch synthase gene: GBSSII; Agricultural Research and Development Promotion Committee; 2000, p. 119-120.

(Continued)

*Primary Examiner* — Brent T Page
(74) *Attorney, Agent, or Firm* — Hoffmann & Baron, LLP

(57) ABSTRACT

The object of the present invention is to provide a wheat which accumulates a starch with a novel property by controlling the expression of the enzymes described in claims.
The present invention provides a wheat, which does not express any of the following proteins (1)-(6): (1) Wheat Starch Synthase II-A1 Protein encoded by Wheat Starch Synthase II-A1 gene of SEQ ID NO:1, (2) Wheat Starch Synthase II-B1 Protein encoded by Wheat Starch Synthase II-B1 gene of SEQ ID NO:3, (3) Wheat Starch Synthase II-D1 Protein encoded by Wheat Starch Synthase II-D1 gene of SEQ ID NO:5, (4) Granule Bound Starch Synthase A1 Protein encoded by Granule Bound Starch Synthase A1 gene of SEQ ID NO:7, (5) Granule Bound Starch Synthase B1 Protein encoded by Granule Bound Starch Synthase B1 gene of SEQ ID NO:9, and (6) Granule Bound Starch Synthase D1 Protein encoded by Granule Bound Starch Synthase D1 gene of SEQ ID NO:11.

4 Claims, 14 Drawing Sheets

OTHER PUBLICATIONS

Yamamori et al.; Genetic elimination of a starch granule protein, SGP-1, of wheat generates an altered starch with apparent high amylose; Theor Appl Genet (2000) vol. 101, pp. 21-29.

Yamamori et al.; Differential effects of Wx-A1, -B1 and _D1 protein deficiencies on apparent amylose content and starch pasting properties in common wheat; Theor Appl Genet (2000); vol. 100, pp. 32-38.

Nakamura et al.; Production of waxy wheats; Ikushugaku Zasshi (Japanese Journal of Breeding) vol. 46 (Extra No. 1) 1996; pp. 6-7.

Nakamura et al.; Rapid classification of partial waxy wheats using PCR-based markers; Genome 45; 2002, pp. 1150-1156.

Shimbata et al.; Mutations in wheat starch synthase II genes and PCR-based selection of a SGP-1 null line; Theor Appl Genet (2005); vol. 111, pp. 1072-1079.

Nakamura et al.; Production of waxy (amylose-free) wheats; Mol Gen Genet (1995), vol. 248; pp. 253-259.

* cited by examiner

TYPE(I)

ANALYSIS OF GRANULE BOUND STARCH SYNTHASE
AND WHEAT STARCH SYNTHASE-II BY SDS-PAGE

WHEAT STARCH SYNTHASE II-A1,D1
WHEAT STARCH SYNTHASE II-B1

GRANULE BOUND STARCH SYNTHASE-A1
GRANULE BOUND STARCH SYNTHASE-B1,D1

MARKER   TYPE(I)   TYPE(II)   TYPE(III)   TYPE(VII)

WHEAT HAVING NEW STARCH AND METHOD FOR PRODUCING IT

CROSS-REFERENCE TO RELATED APPLICATIONS

This application is the National Stage of International Application No. PCT/JP2006/309152 filed May 2, 2006, which claims the benefit of Japanese Application Nos. 2005-134614, filed May 2, 2005 and 2006-042843, filed Feb. 20, 2006, the contents of which is incorporated by reference herein.

TECHNICAL FIELD

The present invention relates to a wheat which does not express Granule Bound Starch Synthase Proteins and Wheat Starch Synthase II Proteins in its endosperm.

BACKGROUND ART

Starch is a mixture of two components. One component is a linear amylose in which glucose are linked by α-1,4 linkage and the other component is an amylopectin which has a branched structure of glucose via α-1,6 linkage. These components are synthesized by the actions of various enzymes and in the case of cereals, they are accumulated in the endosperm of seeds. An amylose has been found to be mainly synthesized by Granule Bound Starch Synthase encoded by Granule Bound Starch Synthase gene. On the other hand, an amylopectin is synthesized by the actions of multiple enzymes. The enzymes include (soluble) Starch Synthase I, (soluble) Starch Synthase II, (soluble) Starch Synthase III, branching enzyme, debranching enzyme and the like.

Starch is also accumulated in the form of a grain highly crystallized in a plant. By adding water to this and heating it, the starch grain gradually swells and then the crystal structure is broken in one breath at a certain temperature (gelatinization peak temperature) to be pasty (gelatinized). Subsequently, on cooling the gelatinized starch, it is gradually increased in its viscosity to be gelled (retrogradated). It has been known that such a property and the ratio of amylose and amylopectin are greatly different depending on the plant species.

Starch is a reserve substance in a plant, as well as an important energy source for animals. In taking starch, not only cereals containing it are utilized as processed foodstuffs, but also it is used as an additive such as a thickener, water retention agent and gel-forming agent by making use of the above property. On the other hand, starch has been also used as a raw material of glue and film in industry. In addition, there is a lot of demands for processed starch which is chemically or physically modified. Starch occupies the majority of the quantity of the organ (seed or tuber) where starch is accumulated. The changes in the starch property highly affect the eating quality or processability of the above products making use of the property, so a demand for the development of starch having diverse properties is large.

The property of starch as described above is greatly different depending on the plant species. However, the diversity of starch in the same plant species owes much to the change of physical property due to the difference of amylose content. For example, in a wheat, the amylose content is about 30% in the usual type of starch, but a lower amylose line whose amylose content is about 20% has been known. The wheat starch of the lower amylose line is considered to be superior to one of the usual type in use as flour for noodle such as Japanese wheat noodle, it has been also commercially cultivated widely. Moreover, in rice and corn, the type in which waxy-type starch whose amylose content is extremely low is accumulated has been known. In a wheat, however, the waxy-type starch has been bred for the first time by Nakamura et al. (JP-A-6-125669 (the term "JP-A" as used herein means an "unexamined published Japanese patent application"), and it has been known to have unique processability and food quality compared to those of usual type. The amylose content has been discussed as one of features representing the characteristics of starch, but in the case of the same plant species, the diversity except for the amylose content is low. Therefore, the diversity of starch from wheat or wheat flour containing it become low, only leading to uniform commodities, so the market is felt to have been already matured. For this, if a wheat which accumulates a starch having a new property can be developed, it allows the development of an improved product providing features different from conventional ones or a new application. The development of such a wheat, therefore, has been desired.

As one example of producing a wheat having a new property, Yamamori et al. reports that they have developed a wheat line in which Wheat Starch Synthase II, one of enzymes which synthesize amylopectin branched chain, is deleted (see Yamamori et al., Theor. Appl. Genet (2000) 101: 21-29). Although it has also been reported that such wheat accumulates high content of amylose, study on other properties has been hardly proceeded, and it has not arrived a practical application.

In a wheat, an amylose is synthesized by Granule Bound Starch Synthase encoded by Granule Bound Starch Synthase gene. In a wheat chromosome which is an allohexaploid, three genomes A, B, D that are homologous chromosomes. Usually, three Granule Bound Starch Synthase genes would exist, and Granule Bound Starch Synthase would be expressed by these genes (Granule Bound Starch Synthase A1, Granule Bound Starch Synthase B1 and Granule Bound Starch Synthase D1). However, there exist the type of chromosomes in which the protein is not expressed due to the mutation produced on the genome DNA, result in 8 combinations of the expression, including wild types. It is known to be found a significant difference in the amylose content according to this pattern. The wheat line in which 1 or 2 proteins are deleted is a lower amylose line, and the type in which all of three proteins are deleted results in glutinous wheat. As a simple method for distinguishing these deleted patterns, a method for directly analyzing proteins expressed in endosperm and a method for investigating based on genome DNA sequences are established (see, for example, JP-A-6-125669 and Nakamura et al., (2002) Genome 45: 1150-1156).

On the other hand, Wheat Starch Synthase II Protein has been known as one of enzymes which are involved in the synthesis of branched chains of amylopection. Each Protein of Wheat Starch Synthase II is encoded by each of three Wheat Starch Synthase II genes located on 7A, 7B and 7D chromosome respectively (Wheat Starch Synthase II-A1, Wheat Starch Synthase II-B1 and Wheat Starch Synthase II-D1). As for Wheat Starch Synthase II Protein also, a method for distinguish deleted patterns has been already developed by present inventors. Although expression patterns can be also divided into 8 combinations as for Wheat Starch Synthase II Protein using this method, the sufficient research on starch property in each pattern has not been made.

DISCLOSURE OF THE INVENTION

The object of the present invention, therefore, is to provide a wheat which accumulates a starch with a new property by controlling the expression of the enzyme described above.

Various studies to obtain a wheat having a new property have been done and consequently a wheat having a very high raw starch-degradation rate and a wheat having a very low gelatinized starch viscosity can be obtained by allowing a certain gene to be mutated and by controlling the expression of a certain protein. That is to say, the present invention provides a wheat which does not express any of (1) Wheat Starch Synthase II-A1 Protein encoded by Wheat Starch Synthase II-A1 gene of SEQ ID NO:1, (2) Wheat Starch Synthase II-B1 Protein encoded by Wheat Starch Synthase II-B1 gene of SEQ ID NO:3, (3) Wheat Starch Synthase II-D1 Protein encoded by Wheat Starch Synthase II-D1 gene of SEQ ID NO:5, (4) Granule Bound Starch Synthase A1 Protein encoded by Granule Bound Starch Synthase A1 gene of SEQ ID NO:7, (5) Granule Bound Starch Synthase B1 Protein encoded by Granule Bound Starch Synthase B1 gene of SEQ ID NO:9, and (6) Granule Bound Starch Synthase D1 Protein encoded by Granule Bound Starch Synthase D1 gene of SEQ ID NO:11.

Moreover, the present invention provides a wheat which does not have any of enzyme activities of said proteins (1)-(6).

In addition, the present invention provides a wheat in which the content of starch which does not form a starch granule in the grain size of 10 µm or more is 30% by mass or more of starch accumulated therein.

In addition, the present invention provides a wheat in which a percentage of the number of a branched chain in which a degree of polymerization is 3 to 5 among branched chains having up to 70 of the degree of polymerization is not less than 1.5% in a branched chain of amylopectin.

Moreover, the present invention provides a wheat in which a percentage of the number of a branched chain in which a degree of polymerization is 3 to 5 among branched chains having up to 70 of the degree of polymerization is not less than 3% in a branched chain of amylopectin.

In addition, the present invention provides a wheat in which rate of raw starch digested by amylase is not less than 80%.

Moreover, the present invention provides a wheat which dose not express one or more of said proteins (1)-(3) and dose not express one or more of said proteins (4)-(6) (with the proviso that a wheat which dose not express only said proteins (2), (4) and (5) simultaneously is excepted).

In addition, the present invention provides a wheat which does not have one or more of enzyme activities of said proteins (1)-(3) and does not have one or more enzyme activities of said proteins (4)-(6) (with the proviso that a wheat does not have only activities of said proteins (2), (4) and (5) is excepted).

Moreover, the present invention provides a wheat which dose not express any two of said proteins (1)-(3) and dose not express one or more of said proteins (4)-(6).

In addition, the present invention provides a wheat which does not have any two of enzyme activities of said proteins (1-(3) and does not have one or more of enzyme activities of said proteins (4)-(6).

Moreover, the present invention provides a wheat which dose not express two or more of said proteins (1)-(3) and dose not express two or more of said proteins (4)-(6).

In addition, the present invention provides a wheat which does not have two or more of enzyme activities of said proteins (1)-(3) and does not have two ore more enzyme activities of said proteins (4)-(6).

Moreover, the present invention provides a wheat which dose not express any two of said proteins (1)-(3) and dose not express any of said proteins (4)-(6).

Moreover, the present invention provides a wheat which does not have any two of enzyme activities of said proteins (1)-(3) and dose not have any of enzyme activities of said proteins (4)-(6).

Moreover, the present invention provides a wheat which dose not express two or more of said proteins (1)-(3) and in which viscosity of gelatinized starch is small compared to that of another wheat, which other wheat expresses Granule Bound Starch Synthase Proteins in the same combination as the former wheat and which other wheat expresses all of said proteins (1)-(3).

In addition, the present invention provides a wheat which dose not express two or more of said proteins (1)-(3) and in which retrogradation tolerance of gelatinized starch is improved compared to that of another wheat, which other wheat expresses Granule Bound Starch Synthase Proteins in the same combination as the former wheat and which other wheat expresses all of said proteins (1)-(3).

Moreover, the present invention provides a method for screening the desired wheat comprising the steps of:
detecting one or more of the following gene mutants (7)-(9):
(7) Wheat Starch Synthase II-A1 gene mutant in which bases of at least positions 124 to 412 of Wheat Starch Synthase II-A1 gene of SEQ ID NO:1 are deleted and/or replaced,
(8) Wheat Starch Synthase II-B1 gene mutant in which one or more bases are inserted into at least between positions 6145 and 6146 of bases of Wheat Starch Synthase II-B1 gene of SEQ ID NO:3,
(9) Wheat Starch Synthase II-D1 gene mutant in which bases of at least positions 2590 to 2652 of Wheat Starch Synthase II-D1 gene of SEQ ID NO:5 are deleted; and
detecting one or more of the following proteins (4)-(6):
(4) Granule Bound Starch Synthase A1 Protein encoded by Granule Bound Starch Synthase A1 gene of SEQ ID NO:7,
(5) Granule Bound Starch Synthase B1 Protein encoded by Granule Bound Starch Synthase B1 gene of SEQ ID NO:9, and
(6) Granule Bound Starch Synthase D1 Protein encoded by Granule Bound Starch Synthase D1 gene of SEQ ID NO:11.

Moreover, the present invention provides a food comprising said wheat or a starch from said wheat.

Moreover, the present invention provides an industrial product comprising said wheat or a starch from said wheat.

Moreover, the present invention provides a processed product using said wheat or a starch from said wheat.

Further, the present invention provides a wheat containing not less than 0.1% by mass of glucose in a mature seed whose embryo has been removed.

In addition, the present invention provides a wheat containing not less than 0.1% by mass of maltose in a mature seed whose embryo has been removed.

Moreover, the present invention provides a wheat containing not less than 1% by mass of sucrose in a mature seed whose embryo has been removed.

As used herein, a mature seed refers to a seed at the time that "wheat head has turned yellow and grain hardness reached wax-like" (Tensaku Zensyo, vol. 1, Wheat, Nobunkyo edd., p. 88), which seed has no sign of germination.

In addition, the present invention provides a wheat in which a percentage of the number of a branched chain in which a degree of polymerization is 2 to 5 among branched chains having up to 60 of the degree of polymerization is not less than 3% in a branched chain of amylopectin.

Moreover, the present invention provides a wheat in which a percentage of the number of a branched chain in which a degree of polymerization is 2 to 5 among branched chains having up to 60 of the degree of polymerization is not less than 5% in a branched chain of amylopectin.

BEST MODE FOR CARRYING OUT THE INVENTION

The wheat according to the present invention does not express any of (1) Wheat Starch Synthase II-A1 Protein encoded by Wheat Starch Synthase II-A1 gene of SEQ ID NO:1, (2) Wheat Starch Synthase II-B1 Protein encoded by Wheat Starch Synthase II-B1 gene of SEQ ID NO:3, (3) Wheat Starch Synthase II-D1 Protein encoded by Wheat Starch Synthase II-D1 gene of SEQ ID NO:5, (4) Granule Bound Starch Synthase A1 Protein encoded by Granule Bound Starch Synthase A1 gene of SEQ ID NO:7, (5) Granule Bound Starch Synthase B1 Protein encoded by Granule Bound Starch Synthase B1 gene of SEQ ID NO:9, and (6) Granule Bound Starch Synthase-D1 Protein encoded by Granule Bound Starch Synthase-D1 gene of SEQ ID NO:11.

The examples of (1) Wheat Starch synthase II-A1 Protein encoded by Wheat Starch Synthase II-A1 gene of SEQ ID NO:1 include Wheat Starch Synthase II-A1 Protein represented by the sequence of SEQ ID NO:2 or Wheat Starch Synthase II-A1 Protein in which the homology with the sequence of SEQ ID NO:2 is not less than 90%. As used herein, the homology is calculated by using Genetyx (from Genetyx company).

The examples of (2) Wheat Starch Synthase II-B1 Protein encoded by Wheat Starch Synthase II-B1 gene of SEQ ID NO:3 include Wheat Starch Synthase II-B1 Protein represented by the sequence of SEQ ID NO:4 or Wheat Starch Synthase II-A1 Protein in which the homology with the sequence of SEQ ID NO:4 is not less than 90%.

The examples of (3) Wheat Starch Synthase II-D1 Protein encoded by Wheat Starch Synthase II-D1 gene of SEQ ID NO:5 include Wheat Starch Synthase II-B1 Protein represented by the sequence of SEQ ID NO:6 or Wheat Starch Synthase II-A1 Protein in which the homology with the sequence of SEQ ID NO:6 is not less than 90%.

The examples of (4) Granule Bound Starch Synthase A1 Protein encoded by Granule Bound Starch Synthase A1 gene of SEQ ID NO:7 include Granule Bound Starch Synthase A1 Protein represented by the sequence of SEQ ID NO:8 or Granule Bound Starch Synthase A1 Protein in which the homology with the sequence of SEQ ID NO:8 is not less than 90%.

The examples of (5) Granule Bound Starch Synthase B1 Protein encoded by Wheat Starch Synthase B1 gene of SEQ ID NO:9 include Granule Bound Starch Synthase B1 Protein represented by the sequence of SEQ ID NO:10 or Granule Bound Starch Synthase B1 Protein in which the homology with the sequence of SEQ ID NO:10 is not less than 90%.

The examples of (6) Granule Bound Starch Synthase D1 Protein encoded by Granule Bound Starch Synthase D1 gene of SEQ ID NO:11 include Granule Bound Starch Synthase D1 Protein represented by the sequence of SEQ ID NO:12 or Granule Bound Starch Synthase D1 Protein in which the homology with the sequence of SEQ ID NO:12 is not less than 90%.

By detecting the existence and mutation of the genes encoding above proteins (1)-(6), it can be confirmed that above proteins (1)-(6) are not expressed. The method for confirming that above proteins (1)-(6) are not expressed may be any methods which can detect any mutations of gene sequences known by those skilled in the art, including, for example, a PCR method and the like.

The PCR method is not particularly limited, and various known improved methods can be used. To give an example, a pair of primers, a template (to be tested) DNA, as well as Tris-HCl, KCl, $MgCl_2$, each dNTP, TaqNDA polymerase and the like are mixed to provide a PCR reaction solution. One cycle of PCR consists of the following three steps: thermal denaturation, annealing of primers and DNA synthesis reaction by DNA polymerase. Each step requires respective different reaction temperature and reaction time, so appropriate ranges are taken depending on the base sequence of DNA area to be amplified and the length thereof. The thermal cycler for such an operation is commercially available. By the examination of suitable PCR conditions such as TaqDNA polymerase, the concentration of $MgCl_2$, reaction cycle and the like, or by using a nested PCR, the detection sensitivity can be further improved.

PCR products may be identified by using immune reactions, or may be identified in any wise. PCR products are electrophoresed, if necessary, by using a positive control or a negative control, and if clear bands can be recognized in electrophoretograms, then can be confirmed the existence of detection substances (Granule Bound Starch Synthase gene and Wheat Starch Synthase II gene mutant wheat) in the substances to be tested.

As a primer used for PCR, any one which can detect the mutation of the genes encoding above proteins (1)-(6) can be used.

The present inventors have found (7) Wheat Starch Synthase II-A1 gene mutant in which bases of at least positions 124 to 412 are deleted and/or are replaced in Wheat Starch Synthase II-A1 gene of SEQ ID NO:1 (SEQ ID NO:27), (8) Wheat Starch Synthase II-B1 gene mutant in which one or more genes are inserted into at least between positions 6145 and 6146 in Wheat Starch Synthase II-B1 gene of SEQ ID NO:3 (SEQ ID NO:28), and (9) Wheat Starch Synthase II-D1 gene mutant in which bases of at least positions 2590 to 2652 are deleted in Wheat Starch Synthase II-D1 gene of SEQ ID NO:5 (SEQ ID NO:29), as a mutant of Wheat Starch Synthase II gene.

Therefore, primers that can detect the mutation of Wheat Starch Synthase II-A1 gene of SEQ ID NO: 1 include, for example, (i) a combination of a primer whose 3'-terminal is hybridized upstream from the position 124 in Wheat Starch Synthase II-A1 gene domain of SEQ ID NO:1 and a primer whose 5'-terminal is hybridized downstream from the position 412 in Wheat Starch Synthase II-A1 gene domain of SEQ ID NO:1, (ii) a combination of a primer whose 3'-terminal is hybridized downstream from the position 412 in Wheat Starch Synthase II-A1 gene domain of SEQ ID NO:1 in such a way that it straddles deleted region 124 to 412 and a primer whose 5'-terminal is hybridized downstream from the position 412 in Wheat Starch Synthase II-A1 gene domain of SEQ ID NO:1, and (iii) a combination of a primer whose 3'-terminal is hybridized upstream from the position 124 in Wheat Starch Synthase II-A1 gene domain of SEQ ID NO:1 and a primer whose 5'-terminal is hybridized upstream from the position 124 in Wheat Starch Synthase II-A1 gene domain of SEQ ID NO:1 in such a way that it straddles deleted region 124 to 412.

Furthermore, it is desirable to design such that the above primers of (i), (ii) and (iii) can detect specifically Wheat Starch Synthase II-A1 gene domain. Concretely, it is a primer that is designed into a domain which dose not match Wheat Starch Synthase II gene domain (Wheat Starch Synthase II-B1, starch synthase II-D1) derived from other genome completely.

Concretely, it includes a combination of a primer comprising the sequence according to any one of SEQ ID NO:13 or 14 and a primer comprising the sequence according to any one of SEQ ID NO:15 to 17.

In addition, primers that can detect the mutation of Wheat Starch Synthase II-B1 gene of SEQ ID NO:3 include, for example, (i) a combination of a primer whose 3'-terminal is hybridized upstream from the position 6145 in Wheat Starch Synthase II-B1 gene domain of SEQ ID NO:3 and a primer whose 5'-terminal is hybridized downstream from the position 6146 in Wheat Starch Synthase II-B1 gene domain of SEQ ID NO:3, (ii) a combination of a primer whose 3'-terminal is hybridized to the bases inserted between the position 6145 and 6146 in Wheat Starch Synthase II-B1 gene domain of SEQ ID NO:3 and a primer whose 5'-terminal is hybridized downstream from the position 6146 in Wheat Starch Synthase II-B1 gene domain of SEQ ID NO:3, (iii) a combination of a primer whose 3'-terminal is hybridized upstream from the position 6145 in Wheat Starch Synthase II-B1 gene domain of SEQ ID NO:3 and a primer whose 5'-terminal is hybridized to the base inserted between the position 6145 and 6146 in Wheat Starch Synthase II-B1 gene domain of SEQ ID NO:3, and (iv) a combination of a primer whose 3'-terminal is hybridized to the bases inserted between the position 6145 and 6146 in Wheat Starch Synthase II-B1 gene domain of SEQ ID NO:3 and a primer whose 5'-terminal is hybridized to the base inserted between the position 6145 and 6146 in Wheat Starch Synthase II-B1 gene domain of SEQ ID NO:3.

Furthermore, it is desirable to design such that the above primers of (i), (ii), (iii) and (iv) can detect specifically Wheat Starch Synthase II-B1 gene domain. Concretely, it is a primer that is designed into a domain which dose not match Wheat Starch Synthase II gene domain (starch synthase II-A1, starch synthase II-D1) derived from other genome completely.

Concretely, it includes a combination of a primer comprising the sequence according to any one of SEQ ID NO:18 to 20 and a primer comprising the sequence according to any one of SEQ ID NO:21 to 23.

In addition, primers that can detect the mutation of Wheat Starch Synthase II-D1 gene SEQ ID NO:5 include, for example, (i) a combination of a primer whose 3'-terminal is hybridized upstream from the position 2590 in Wheat Starch Synthase II-D1 gene domain of SEQ ID NO:5 and a primer whose 5'-terminal is hybridized downstream from the position 2652 in Wheat Starch Synthase II-D1 gene domain of SEQ ID NO:5, (ii) a combination of a primer whose 3'-terminal is hybridized downstream from the position 2652 in Wheat Starch Synthase II-D1 gene domain of SEQ ID NO:5 in such a way that it straddles deleted region 2590 to 2652 and a primer whose 5'-terminal is hybridized downstream from the position 2652 in Wheat Starch Synthase II-D1 gene domain of SEQ ID NO:5, and (iii) a combination of a primer whose 3'-terminal is hybridized upstream from the position 2590 in Wheat Starch Synthase II-D1 gene domain of SEQ ID NO:5 and a primer whose 5'-terminal is hybridized upstream from the position 2590 in Wheat Starch Synthase II-D1 gene domain of SEQ ID NO:5 in such a way that it straddles deleted region 2590 to 2652.

Furthermore, it is desirable to design such that the above primers of (i), (ii) and (iii) can detect specifically Wheat Starch Synthase II-D1 gene domain. Concretely, it is a primer that is designed into a domain which dose not match Wheat Starch Synthase II gene domain (starch synthase II-A1, starch synthase II-B1) derived from other genome completely.

Concretely, it includes a combination of a primer comprising the sequence according to any one of SEQ ID NO:24 or 25 and a primer comprising the sequence according to SEQ ID NO:26.

As a method for detecting the mutation of the genes encoding the above Proteins (4)-(6), the method described in Nakamura et al., (2002) Genome 45: 1150-1156 can be used.

Furthermore, methods for detecting the mutation of the genes encoding the above Proteins (1)-(6) include LAMP method, NASBA method, LCR method, SDA method, RCR method, TMA method, the qualitative or quantitative method of mRNA by RT-PCR and the like in addition to PCR method. Although any methods that can detect the mutation of the present gene sequence may be used, for example, including LAMP method, in which primers are designed with reference to the method described in the report by Notomi et al. (Notomi et al., Nucleic Acids Research (2000), 28, No. 12, e63). If the sequence to be detected at this time is the sequence of (1), a primer in which the region into which the positions 124 to 412 of SEQ ID NO:13 will be put is a detection region may be designed. Moreover, if the sequence to be detected is the sequence of (2), a primer in which a part of the sequence at the positions 6145 to 6146 of SEQ ID NO:14 is a detection region may be designed. Moreover, if the sequence to be detected is the sequence of (3), a primer in which the region into which the positions 2590 to 2652 of SEQ ID NO:15 will be put is a detection region may be designed. By adding a template DNA solution, dNTP, BstDNA polymerase required in the reaction and other reagents necessary for the reaction in addition to the designed primer and performing the reaction at 65° C. to detect the product by an appropriate method, the detection of Wheat Starch Synthase II gene mutant wheat or the judgment of the type of Wheat Starch Synthase II gene can be performed. Even other methods can perform the same detection and judgment by setting up detection systems according to the manuals in the same manner.

In addition, a method for confirming that the above Proteins (1)-(3) are not expressed includes the method described in the report by Yamamori et al. (Yamamori et al., Theor. Appl. Genet (2000) 101: 21-29).

Moreover, as a method for confirming that the above Proteins (4)-(6) are not expressed, the method described in JP-A-6-125669 can be also used.

In the wheat according to the present invention described above, the content of starch which dose not form a starch grain in the grain size of 10 μm or more is 30% by mass or more of starch accumulated. The percentage of forming a starch granule in the grain size of 10 μm or more can be calculated by using an electron microscope or a light microscope to observe the cross section of wheat seed endosperm and obtaining the percentage in a fixed area of granules of 10 μm or more in the fixed area. Alternately, during the purification process of starch, it can be obtained by separating a fraction in which dose not form starch granules and a fraction of starch granules to measure the dry quantities of these fractions. By decreasing the percentage of forming starch granules in the grain size of 10 μm or more, the digestion by starch-hydrolyzing enzyme such as amylase and pullulanase is easily caused and then easy-digestive starch can be provided. If such a starch is used, a food that is easy to be digested and absorbed into a body can be provided. Moreover, because starch forms a higher-order structure, it is not gelatinized completely even in heating in boiling water. However, because the type of starch according to the present invention is considered not to form a higher-order structure, the gelatinization may be possibly achieved at lower temperature and in shorter time, so it is a suitable material to cook at lower temperature and in shorter time. If a cooking at lower temperature and in shorter time is possible, it also has the advantage such as being able to significantly decrease the effect on other materials due to heating or being able to try energy-saving or the like. Further, because it dose not form a granule, it is suitable for use as raw material for film and the like.

Moreover, in the wheat according to the present invention described above, a percentage of the number of a glucose branched chain in which a degree of polymerization is 3 to 5 among branched chains having up to 70 of the degree of polymerization is not less than 1.5% in a branched chain of amylopectin. Preferably, it is not less than 3%. In addition, in the wheat according to the present invention described above, a percentage of the number of a branched chain in which a degree of polymerization is 2 to 5 among branched chains having up to 60 of the degree of polymerization is not less than 3%. Preferably, it is not less than 5%. The structure of a starch can be greatly changed by having such a chain-length distribution. Practically, in the present invention, by allowing starch to be of such a type, most polysaccharide do not form granule and then the structural property could be greatly changed. Practically, the sugar component which could not form starch granule is accumulated as a base substance consisting of a smooth continuous layer, which affects multilaterally the physical properties. For example, gel-like layer is formed during purification process of starch. Usually, such accumulation of gel-like substance cannot be seen during purification process of starch and it can be used, for example, as a material for industrial products such as films.

In addition, the application as a water retention agent and the like is expected because this gel-like substance has very high water retention capacity.

Alternately, it can be utilized as a coating agent for a surface.

Here, amylopectin is a macro molecule in which glucose chains linearly linked by α-1,4 linkage are branched via α-1,6 linkage and then linked to be constructed. The diversity between amylopectin molecules can be seen on their molecular weight and the number or length of the branches. Therefore, the chain-length distribution of the glucose branched chains in the amylopectin according to the present invention shows the average distribution over amylopectin accumulated in a seed.

Moreover, in the wheat according to the present invention as described above, rate of raw starch digested by amylase is not less than 80%. Preferably, it is not less than 90%. Because of the improvement of the degradability in the form of raw starch which gelatinization by heat is not performed, it is considered that such a starch will be easily digested and absorbed effectively even if it is not cooked by heating. Alternately, it can be also used as raw material for biodegradable plastic.

In addition, other wheat according to the present invention dose not have any of enzyme activities of (1) Wheat Starch Synthase II-A1 Protein encoded by Wheat Starch Synthase II-A1 gene of SEQ ID NO:1, (2) Wheat Starch Synthase II-B1 Protein encoded by Wheat Starch Synthase II-B1 gene of SEQ ID NO:3, (3) Wheat Starch Synthase II-D1 Protein encoded by Wheat Starch Synthase II-D1 gene of SEQ ID NO:5, (4) Granule Bound Starch Synthase A1 Protein encoded by Granule Bound Starch Synthase A1 gene of SEQ ID NO:7, (5) Granule Bound Starch Synthase B1 Protein encoded by Granule Bound Starch Synthase B1 gene of SEQ ID NO:9, and (6) Granule Bound Starch Synthase D1 Protein encoded by Granule Bound Starch Synthase D1 gene of SEQ ID NO:11.

The above proteins (1)-(3), as was stated previously, are said generally to be involved in the synthesis of amylopectin branched chains (glucose polymer branched via α-1,6 linkage), particularly the chains whose degree of polymerization is moderate (chains having degree of polymerization of from about 15 to 25). Therefore, the enzyme activities of these proteins can be also considered as activities which recognize ADP-glucose and amylopectin serving as substrates and link with them, and then allow glucose from ADP-glucose to link with the terminal of amylopectin branched chain. On the other hand, the above Proteins (4)-(6) are believed basically to be involved in the synthesis of amylose. Therefore, the enzyme activities can be also considered as actions which recognize ADP-glucose and amylose serving as substrates and link with them, and then allow glucose from ADP-glucose to add to the terminal of amylose during extension.

In order to confirm enzyme activities of the above Proteins (1)-(6), any methods generally used may be used. To give an example, these enzymes are purified from seeds and then reacted by adding [U-14C]ADP-glucose or glycogen or amylopectin serving as substrates, as well as any components to adjust reaction conditions to them. At the point of the reaction of a certain time has completed, the enzymes are inactivated by heating to 100° C., unreacted [U-14C]ADP-glucose is removed using an anion exchange column, and then the quantity of [U-14C]ADP-glucose incorporated in glycogen or amylopectin is measured by using a liquid scintillation counter. In another method, acrylamide gel electrophoresis are performed under condition which SDS and β-mercaptoethanol are removed from usual SDS-PAGE for protein fraction or starch fraction (expressing as protein content, 5-μg) roughly purified from seeds. The gel that the separation has been completed is soaked in a solution consisting of 50 mM glycine, 100 mM ammonium sulfate, 5 nM β-mercaptoethanol, 5 mM $MgCl_2$, 0.5 mg/ml bovine serum albumin, 0.01 mg/ml glycogen or amylose, and 4 mM ADP-glucose, and allowed to stand for from 4 to 12 hours. Subsequently, a solution consisting of 0.2% iodine and 0.02% potassium iodide are added to dye, and then the enzyme activities are determined. Such a method may be used.

Moreover, as described above, a method for confirming the expression of proteins in themselves or a method for distinguishing the mutations on genome DNA as allowing the enzyme activities to lose may be used. In the proteins (1)-(3), "the mutation on genome DNA as allowing the enzyme activities to lose" includes the recognition of ADP-glucose and amylopectin serving as substrates of the enzyme, the mutation at binding site, the mutation at the active center site where glucose is transferred to the non-reduced terminal of amylopectin, the mutation of signal sequence site present at N-terminal or the like. In the proteins (4)-(6), "the mutation on genome DNA as allowing the enzyme activities to lose" includes the recognition of ADP-glucose and amylose serving as substrates of the enzyme, the mutation at binding site, the mutation at the active center site where glucose is transferred to the non-reduced terminal of amylose or the like. When particularly mutagenesis treatment by irradiation of radioactive rays or administration of mutagenic chemical substances are performed, the mutation accompanied with amino acid replacement by only one residue is possibly caused. In such a case, a method for confirming the mutation on DNA is suitable because the confirmation by SDS-PAGE is often difficult to distinguish. Methods for confirming the mutation on DNA sequence are as described above.

In addition, another wheat according to the present invention dose not express one or more of the above Proteins (1)-(3), and dose not express one or more of the above Proteins (4)-(5) (with the proviso that a wheat which dose not express only proteins (2), (4) and (5) simultaneously is excepted). Such a wheat accumulates a starch with a new property compared to the starch accumulated in conventional wheat. New property includes, for example, the modifications of viscosity of the gelatinized solution, gelatinization peak temperature, retrogradation tolerance, freeze-thaw tolerance, degradability by digestive enzyme and the like. Particularly, in the present invention, it has been found that the deletion of one or more Wheat Starch Synthase II Proteins result in increased gelatinization degree, decreased viscosity of the gelatinized solution and decreased retrogradation degree compared to the type of non-deleted. Moreover, it has been found that its effect changes dramatically if one or more Granule Bound Starch Synthases are deleted simultaneously. The starch accumulated in such a wheat is a starch with higher gelatinization degree, a starch with lower viscosity, or a starch with improved retrogradation tolerance at the point of cooling after gelatinization compared to conventional starch. Particularly, a wheat which dose not express one of the above Proteins (1)-(3) and dose not express two of the above Proteins (4)-(6) is dramatically improved in retrogradation tolerance after gelatinization and freeze-thaw tolerance compared to a wheat which expresses all of the above Proteins (1)-(3) and dose not express two of the above Proteins (4)-(6). Alternately, a wheat which dose not express two of the above Proteins (1)-(3) and dose not express any of the above Proteins (4)-(6) is greatly decreased in viscosity of gelatinized solution. In order to confirm such a wheat, a method in which the existence and mutation of genes encoding the above Proteins (1)-(6) is detected to confirm or a method in which the expression of the proteins in themselves is confirmed may be used. Alternately, a method in which RNAs expressed by gene sequences according to SEQ ID NO:1 to 11 are purified to perform qualitative or quantitative analysis may be used.

A wheat which dose not express any two of the above Proteins (1)-(3) and dose not express one or more of the above Proteins (4)-(6) is preferable. In such a wheat, particularly viscosity of gelatinized starch is significantly decreased compared to that of conventional wheat. This feature is particularly remarkable in a wheat which dose not express two of the above Proteins (1)-(3) and dose not express any of the above Proteins (4)-(6).

A wheat which dose not express two or more of the above Proteins (1)-(3) and dose not express two or more of the above Proteins (4)-(5) is also preferable. In such a wheat, particularly retrogradation tolerance of gelatinized starch is improved compared to that of conventional wheat. This feature is particularly remarkable in a wheat which dose not express any two of the above Proteins (1)-(3) and dose not express any of the above Proteins (4)-(6).

In addition, the other wheat according to the present invention dose not have one or more of enzyme activities of the above Proteins (1)-(3) and dose not have one or more of enzyme activities of the above Proteins (4)-(6) (with the proviso that a wheat which dose not express only enzyme activities of the above Proteins (2), (4) and (5) is excepted).

A wheat which dose not have two or more of enzyme activities of the above Proteins (1)-(3) and dose not have two or more of enzyme activities of the above Proteins (4)-(6) is more preferable.

A wheat which dose not have any two of enzyme activities of the above Proteins (1)-(3) and dose not have one or more of enzyme activities of the above Proteins (4)-(6) is more preferable.

A wheat which dose not have any two of enzyme activities of the above Proteins (1)-(3) and dose not have any of enzyme activities of the above Proteins (4)-(6) is more preferable.

Moreover, in a wheat, by allowing two or more of the above Proteins (1)-(3) not to express, viscosity of gelatinized starch can be decreased compared to that of another wheat, which other wheat expresses Granule Bound Starch Synthase Protein in the same combination as the former wheat and which other wheat expresses all of the above Proteins (1)-(3).

Furthermore, in a wheat, by allowing two or more of the above Proteins (1)-(3) not to express, retrogradation tolerance of gelatinized starch can be improved compared to that of another wheat, which other wheat expresses Granule Bound Starch Synthase Protein in the same combination as the former wheat and which other wheat expresses all of the above Proteins (1)-(3).

From the above, the desired wheat can be screened using the steps of detecting one or more of the above gene mutants (7)-(9) and detecting one or more of the above Proteins (4)-(6). Here, the desired wheat includes a wheat which dose not have any of the above Proteins (1)-(6), in which rate of degradation of raw starch is not less than 80%. Alternately, the desired wheat includes a wheat which dose not express (1) and (2) of the above Proteins (1)-(3) and dose not express any of the above Proteins (4)-(6), in which viscosity of gelatinized solution is very small.

In addition, the wheat according to the present invention and the starch from the wheat according to the present invention can be used in foods. Said foods include foods which utilize general wheat flour (including whole grain flour) or starch. For example, said foods includes the use as bakery foods, noodles, cakes, deep-fried things, grilled things, pastes, a binder of hamburg steaks and the like. The grain flour and starch from the present wheat may be used as it is, or may be mixed with other flour to use. In addition, it may be used as fermentation material of alcoholic beverage or the like and raw material for microbial production of amino acid or polysaccharide.

Bakery foods which may be produced using the wheat according to the present invention include, for example, breads such as loaf breads, French breads, rolls and sweet breads, fried breads such as yeast doughnuts, steamed breads, pizzas such as pizza pies, cakes such as sponge cakes, and toasted snacks such as cookies and biscuits. Grain flours derived from the wheat according to the present invention used to produce these bakery foods may be those that are milled according to general methods to remove brans or may be whole grain flours that are not fractionated. Grain flours for bakery foods used in producing the bakery foods may be grain flours indicated above used alone, but preferably they are used in mixture with other grain flours. Said other grain flours include, for example, wheat flours such as hard flours, medium flours, soft flours and other wheat flours which are not classified into these groups, rye flours, rice flours and starch. Bakery foods according to the present invention may be produced by mixing grain flours obtained from the wheat according to the present invention or mixed grain flours in mixture with other grain flours with other ingredients generally used to produce bakery foods, such as yeast, chemical baking powder such as baking soda, yeast food, salt, sugar, oils and fats, egg, dairy products and water to produce a dough, and swelling it by fermentation etc. or directly toasting or frying it. Any of the generally used production methods, production devices, freezing methods and freezing devices may be used in producing the bakery foods according to the present invention.

Bakery products thus produced which include the grain flours derived from the wheat according to the present invention are sweet and have unique flavor, smell and texture. These features may be obtained when grain flours derived from the wheat according to the present invention are used alone, but preferably it is obtained by admixing them with other grain flours so that the mixture contains 0.1-60% by mass, more preferably 0.5-50% by mass of the grain flour derived from the wheat according to the present invention.

Moreover, the wheat according to the present invention and the starch from the wheat according to the present invention can be used in industrial products. Said industrial products include viscosity stabilizer, water retention agent, colloid stabilizer, glue, adhesive and the like.

In addition, the wheat according to the present invention and the starch from the wheat according to the present invention can be processed to use. For example, such a process includes a method in which dextrin is produced by acid, base or enzyme treatment and then the dextrin is used in adhesive, fiber, film and the like. Moreover, a water-soluble fraction of this dextrin can be used in a functional food with an excellent action for intestinal disorder or the like as a resistant dextrin. Alternately, it can be also used by reacting with various inorganic or organic acids to form starch ester. Particularly, starch phosphate obtained by reacting starch with phosphoric acid is useful as a thickener.

In addition, a wheat which dose not express any of the above Proteins (1)-(6) has an increased sugar content compared to that of conventional wheat. Concretely, such a wheat contains not less than 0.1% by mass of glucose in a mature seed whose embryo has been removed. Preferably, it contains not less than 0.3% by mass of glucose in a mature seed whose embryo has been removed. More preferably, it contains not less than 0.5% by mass of glucose in a mature seed whose embryo has been removed. Moreover, it contains not less than 0.1% by mass of maltose in a mature seed whose embryo has been removed. Preferably, it contains not less than 0.3% by mass of maltose in a mature seed whose embryo has been removed. More preferably, it contains not less than 0.5% by mass of maltose in a mature seed whose embryo has been removed. Moreover, it contains not less than 1% by mass of sucrose in a mature seed whose embryo has been removed. Preferably, it contains not less than 3% by mass of sucrose in a mature seed in whose embryo has been removed. More preferably, it contains not less than 5% by mass of sucrose in a mature seed in whose embryo has been removed.

As a method for measuring the content of glucose, maltose and sucrose in a seed, any methods in which low molecular weight sugar is extracted from a seed to analyze can be used. As a method for recovering low molecular weight sugar from a seed, a method in which a seed is ground followed by extraction with water, extraction with 80% ethanol, extraction with DMSO or the like is possible. However, in order to distinguish clearly the low molecular weight sugar from a sugar which starch or polysaccharide is digested by enzyme such as amylase to produce during operation, it is desirable to extract and measure the low molecular weight sugar under condition that amylase activity does not affect. Moreover, because the present invention is a wheat in which sugar is accumulated in high content at the wheat endosperm, a seed in which the embryo has been removed therefrom is preferably used as a sample for its measurement. As a method for identifying and quantifying the low molecular weight sugar contained in the extracted sample, any methods such as a method using capillary electrophoresis, a method using HPLC, a method by enzyme and chemical reaction or the like may be used.

The wheat of the present invention include those obtained by cross-fertilizing the above wheat with another variety and then self-fertilizing the F1 generation obtained or backcrossing it with one of its parental lines. For example, the above wheat is cross-fertilized with a generally known variety having high disease resistance, and then the F1 generation obtained is backcrossed with the parental line, the variety having high disease resistance. Among the next generation plants, plants expressing Granule Bound Starch Synthase Proteins and Wheat Starch Synthase II Proteins in a desired combination are screened using the aforementioned methods. By further repeating the backcrossing and screening of the screened plants, a desired starch property may be imparted to the variety having high disease resistance. Alternatively, it is also possible to impart disease resistance to the above wheat by using the above wheat as the parental line for backcrossing and carrying out the screening using appropriate methods. Other useful features include, but are not limited to, gluten property, lodging resistance, winter habit, spring habit, high-yield, cold tolerance, pre-harvesting sprouting resistance and aptitude for milling.

EXAMPLES

1. Sample

The types of Granule Bound Starch Synthase Proteins and Wheat Starch Synthase II Proteins of wheat line developed according to the presental invention are shown together with standard line (a comparative control) (type (i)) or parental line (type (ii) and type (iii)) in Table 1 below. For the wheat line used as parent line for the present invention, a wheat variety Moti Otome (Granule Bound Starch Synthase null type, Wheat Starch Synthase II Protein is wilde type) reared in Tohoku Agricultural Research Center were cross-fertilized with a heterogenous variety, and then F5 generation seed thereof was used to screen the line in which Granule Bound Starch Synthase Protein was deleted (type (ii)). For another parental line, Wheat Starch Synthase II Protein null line reared in the same place was used. This line was a line (type (iii)) in which Wheat Starch Synthase II was deleted completely by cross-fertilizing successively three varieties of generally known line Kanto 79 (Wheat Starch Synthase II-B1 null type), foreign variety Turkey 116 (Wheat Stacch Synthase II-D1 null type) and Chosen57 (Wheat Starch Synthase II-A1 null type).

The culture and cross-fertilization of wheat followed usual methods. Two varieties to be parental lines were cross-fertilized to yield $F_1$ generation. This was self-fertilized to produce the $F_2$ generation or later, and then a desired wheat line was screened from these by distinguishing the existence of Granule Bound Starch Synthase through two-dimensional electrophoresis and the gene type (wild type or mutant type) of Wheat Starch Synthase II gene via PCR method. The wheat line variety Norin 61 (type (i)) which was generally cultivated and distributed was used as a comparative control.

TABLE 1

Genotype of each seed line obtained by cross-fertilization

| | Granule Bound Starch Synthase A1 | Granule Bound Starch Synthase B1 | Granule Bound Starch Synthase D1 | Wheat Starch Synthase II-A1 | Wheat Starch Synthase II-B1 | Wheat Starch Synthase II-D1 | Remarks |
|---|---|---|---|---|---|---|---|
| (i) | ○ | ○ | ○ | ○ | ○ | ○ | wild type |
| (ii) | X | X | X | ○ | ○ | ○ | parent line of (iv)-(vii) |
| (iii) | ○ | ○ | ○ | X | X | X | parent line of (iv)-(vii) |
| (iv) | X | X | ○ | ○ | ○ | ○ | |
| (v) | X | ○ | X | ○ | X | ○ | |
| (vi) | X | X | X | X | X | ○ | |
| (vii) | X | X | X | X | X | X | |
| (viii) | X | ○ | X | ○ | X | X | |
| (ix) | X | X | ○ | ○ | X | X | |
| (x) | X | X | X | ○ | X | X | |

Whether Granule Bound Starch Synthase was wild type or null type was confirmed by two-dimensional electrophoresis of Starch Bound Protein. This method is as follows.

An embryo was removed from a mature seed, the seed was ground and then was passed through a sieve of 60 μm to prepare flour. Cooled SDS buffer (0.1 M Tris-HCl (pH 6.8), 2.3% SDS, 5% β-mercaptoethanol, 10% glycerol) was added at the ratio of 1 mL per 20 mg of the flour, and homogenized for two minutes. This suspension was filtered and then the filtrate was centrifuged for five minutes at 15000 rpm, the supernatant was removed, SDS buffer was added again, suspended and centrifuged. This operation was repeated three times, and then distilled water was added, same operation was repeated two times, the supernatant was removed, and the recovered starch layer was dried naturally to provide purified starch.

If the starch was a usual type, during said purification of the starch, most of the starch would be precipitated at such a stage that SDS buffer was added, filtered followed by centrifugation and then starch grain layer would be formed. So it was clearly distinguished from the above water layer. In the type (vii) of wheat according to the present invention, only trace amount of what seemed to be starch grain layer was precipitated at this stage, and on the upper layer thereof, a layer composed of cloudy structureless gel-like substance was accumulated in a large amount, further a water layer is formed on the upper layer thereof. After the water layer was removed, this gel-like layer that was a sugar component and the starch grain layer of the bottom layer put together, and then subsequent operation was performed in the same way as said purification method.

300 μl of Lysis buffer (8 M Ura, 2% Nonidet P-40, 2% ampholine (pH 3.5-10), 5% β-mercaptethanol, 5% polyvinylpyrrolidone) per 10 mg of this purified starch was added and heating treatment by boiling water at 100° C. was performed for 2 minutes. After cooling it with ice for 10 minutes, the gelatinized starch solution was centrifuged at 15000 rpm at 4° C. for 10 minutes, and 200 μl of the supernatant was subjected to two-dimensional electrophoresis. For the first-dimensional electrophoresis, IEF consisting of 3.5% of acrylamide gel was performed. For the second-dimensional electrophoresis, SDS-PAGE consisting of 15% of bisacrylamide gel was performed.

The result of detecting Granule Bound Starch Synthase is shown in FIG. 1. Granule Bound Starch Synthase-A1, B1 and D1 were detected at the position in FIG. 1A, respectively, but any bands were not detected from the wheat line of type (vii) at all (see FIG. 1B). Therefore, Granule Bound Starch Synthase was deleted completely in the wheat of type (vii).

For the confirmation of Wheat Starch Synthase II, the method which had been already developed by the present inventors (JP Patent Application NO. 2004-15390) was used. Such a method is as follows. A seed was sprouted, genome DNA from the young leaf was treated using DNeasy plant mini kit manufactured by Kiagen Corporation. 100 mg of the young leaf of the sprouted seed was taken to crush until it became powdery in liquid nitrogen. The crushed sample was transferred into 1.5 ml volume tube and then Buffer AP1 and RNase solution attached to the kit were added, heated at 65° C. for 10 minutes. Next, Buffer AP2 was added, the mixture was allowed to stand on ice for 5 minutes and then the precipitate was removed by centrifugal operation. Buffer AP3 was added to the supernatant to mix, then all amount of the mixture was subjected to mini spin column and centrifuged to allow DNA to be adsorbed to membrane. The DNA was washed two times by Buffer AW, then Buffer AE was added to allow it to stand for 5 minutes and DNA solution was recovered by centrifugation.

The sequence mutations occurred on the gene sequences encoding three of Wheat Starch Synthases II were identified by PCR method. The primer sequences used are as follows.

```
Wheat Starch Synthase II-A1
SSIIAF1:   GCGTTTACCCCACAGAGC      (SEQ ID NO: 13)

SSIIAR1:   ACGCGCCATACAGCAAGTCATA  (SEQ ID NO: 17)

Wheat Starch Synthase II-B1
SSIIBF1:   ATTTCTTCGGTACACCATTGG   (SEQ ID NO: 20)
           CTA

SSIIBR1:   TGCCGCAGCATGCC          (SEQ ID NO: 23)

Wheat Starch Synthase II-D1
SSIIDF1:   GGGAGCTGAAATTTTATTGCTT  (SEQ ID NO: 24)
           ATTG

SIIDR1:    TCGCGGTGAAGAGAACATGG    (SEQ ID NO: 26)
```

PCR reaction solution was prepared in the following way. LA Taq (Takara Bio Corporation) was used for reactions. Primers manufactured by FASMAC Corporation were used.

| | | |
|---|---|---|
| 10 x LA Taq buffer | 2 µl | |
| dNTP | 0.2 mM | |
| Mg(Cl)$_2$ | 2.25 mM | |
| Primer 1 | 0.25 µM | |
| Primer 2 | 0.25 µM | |
| Genome DNA | 1 ng/µl | |
| LA Taq | 0.025 U/µl | |
| Total | 20 µl | |

GeneAmp PCR System 9700 (Applied Bio Systems Corporation) was used as PCR amplifier, and the reaction conditions were set as follows.

| | | |
|---|---|---|
| 1st step | 98° C. | 5 min |
| 2nd step | 98° C. | 30 sec |
| (40 cycle) | 65° C. | 30 sec |
| | 74° C. | 1 min |
| 3rd step | 74° C. | 5 min |
| 4th step | 4° C. | |

PCR amplified reaction solution was subjected to electrophoresis by 3% agarose gel, then dyed with ethidium bromide, and the existence of wild type and mutant gene in the sample was determined by identifying optimal size of DNA amplified band by each primer. The results of the determination on the genotype of type (i) of control variety and type (vii) of wheat is shown in FIG. 2. In type (vii), it is shown that all of the three Wheat Starch Synthase II genes are mutant types. From above, in type (vii) of wheat it is found that Granule Bound Starch Synthase and Wheat Starch Synthase II are deleted completely.

[Confirmation of Deletion of Wheat Starch Synthase II and Granule Bound Starch Synthase by SDS-PAGE]

The expression of Wheat Starch Synthase II Proteins and Granule Bound Starch Synthase Proteins in each sample were confirmed by SDS-PAGE. 14 µl of SDS buffer was added per 1 mg of starch purified from type (i), type (ii), type (iii) and type (iv), boiled for 5 minutes and then cooled on ice for 2 minutes. After centrifuging at 15,000 rpm at 4° C. for 5 minutes, the supernatant was collected and used as samples for SDS-PAGE. In SDS-PAGE, acrylamide gels prepared to contain a final concentration of 12.5% of acrylamide solution (a mixture of acrylamide and methylene bisacrylamide in a ratio of 30:0.135) were used to carry out electrophoresis; other conditions were according to usual methods. Silver Staining Kit (Daiichi Pure Chemicals Co., Ltd.) was used for detecting proteins after electrophoresis.

These results also confirmed that type (vii) does not have any of Wheat Starch Synthase II Proteins or Granule Bound Starch Synthase Proteins (FIG. 13).

2. Percentage of Starch which does not Form a Starch Granule in the Grain Size of 10 µm or More in Accumulated Starch When the percentage of starch which does not form a starch granule in the grain size of 10 µm or more in accumulated starch is calculated, in the purification of the above starch, after washing with SDS buffer and washing with water, the gel-like layer and starch grain layer of the bottom layer were separated via a spatula. Each fraction was transferred to 1.5 ml tube which had been previously weighed and then the wet weight of each fraction was measured. After samples were dried naturally, dry weight of each fraction was measured. In usual type of wheat, almost 100% of the starch is starch grain layer and gel-like layer is hardly formed. In contrast to this, the dry weight of starch grain layer from type (vii) of wheat according to the present invention was 22 mg and the dry weight of gel-like layer was 13 mg. Therefore, the weight of the gel-like layer occupying the total weight of the recovered starch fraction was about 37%.

3. Observation by Electron Microscope

The electron micrograph for a seed produced by type (vii) of wheat line is shown in FIG. 3. A mature wheat was roughly ground and the fractured section thereof was observed by an electron microscope (Keyence Corporation). Type (vii) of the starch grain becomes distorted shape and the number of grains is also small compared to type (i) of wild type starch, and most of the starch granules are composed of smooth base substances.

4. Analysis of Chain-Length Distribution 4.1

The results obtained by the analysis of chain-length distribution of branched chains composing amylopectin contained in type (i), type (ii), type (iii) and type (vii) of starches are shown in FIGS. 4 to 6. The method is as follows. Purified starch was weighed, 60 µL of 250 mM NaOH per 1 mg of starch was added and was gelatinized completely by boiling it for 20 minutes. After cooling, 1.9 µL of acetic acid, 240 µL of 50 mM sodium acetate buffer (pH 4.0) and 3.75 µL of 2% sodium azide were added followed by addition of 1 µL of Isoamylase (Nakarai Corporation) and was reacted for 16 hours with stirring at 37° C. After completing the reaction, the reaction mixture was boiled for 20 minutes to inactivate enzymes, and then a supernatant was obtained by centrifugation at 14000 rpm, at 20° C., for 2 minutes, and resin (manufactured by Bio-Rad Corporation) was added to deionize. The resin was precipitated by centrifuging, and then the supernatant was transferred to a new tube and the concentration of oligosaccharide released by enzyme treatment was determined by modified Park-Johnson method (Biochemical Experimental Method 19 "Starch/Related Glucide Experimental Method", Michinori Nakamura and Keiji Kainuma editing, Gakkai Publishing Center, p. 123). A sample solution was appropriately diluted, 25 µl of 0.1% potassium ferricyanide and 25 µl of potassium cyanide solution (what 0.48 g of $Na_2CO_3$, 0.92 g of $NaHCO_3$ and 0.065 g of KCN were dissolved in water into 100 ml) per 50 µl of the resulting solution were added, sealed hermetically, and heated for 15 minutes in boiling water. Subsequently, the resulting mixture was cooled on ice for 10 minutes, 125 µl of 0.3% iron alum solution (what 1.5 g of Fe.NH$_4$(SO)$_2$.H$_2$O was dissolved in 500 ml of 50 mM sulfuric acid) was added, allowed to stand at room temperature for 20 minutes and then the absorbance at 715 nm was measured. The values measured in the same way for glucose solutions whose concentration were changed between 0 and 10 mM were used to create a calibration curve. This calibration curve was used to determine the quantity of reduced terminal groups in the sample solutions. 5 nmol aliquot of each sample was taken, dried under vacuum centrifugation to provide a sample for chain-length distribution analysis. For the chain-length distribution analysis, PA sugar chain analysis kit manufactured by Beckman Corporation was used. 2 µl of maltose quantitative control/mobility marker was added to the dried sample and dried under vacuum centrifugation again. 2 µl of 1M Sodium Cyanoborohydride solution was added to the dried sample and further APTS labeling reagent was added. The reaction was performed at 37° C. in the dark for 4 hours and 46 µl of distilled water was added to stop the reaction. Furthermore, 5 µl of this sample was taken and diluted with distilled water to 40-fold to provide a sample for measurement. For separating determination of oligosaccharides having different degree of polymerization of glucose, capillary electrophoresis apparatus PACE system 5000 manufactured by Beckman Corporation was used. A sample was injected with high pressure for 5 seconds by using eCAP N—CHO capillary as separatory capillary, and then eCAP sugar analysis gel buffer was used to electrophorese at 30 kV for 30 minutes. Each peak area of the oligosaccharide having 3 to 70 of degree of polymerization was calculated from the resulting peak chart, let the total of the peak areas be 100% and the percentage of the area occupied by each peak was obtained. The pattern obtained from type (i) of wheat line was used as a standard to make a graph of each value which the percentage of the peak corresponding to type (i) was subtracted from the percentage of the peak corresponding to each sample peak. In type (vii), the percentage of glucose side chains having degree of polymerization of from 3 to 10 is significantly increased compared to that of type (i) that is a standard line, and conversely the percentage of glucose side chains having degree of polymerization of from 11 to 24 is decreased (see FIG. 4). This is clearly different from the pattern of type (ii)(FIG. 5) or type (iii) (FIG. 6) that is parental line. It is considered that particularly the percentage of glucose side chains having amylose content of 1% or less and degree of polymerization of from 3 to 5 was decreased so that sugar components which could not take starch grain structures resulted in composing smooth base substances.

4.2

Embryo was removed from a seed, the resultant was ground with pestle and mortar, then transferred into 1.5 ml tube. 50 μl of 100% DMSO per 1 mg of the ground seed weight was added. Complete gelatinization was performed by sealing hermetically to boil for 30 minutes and insoluble components were removed by centrifugation. 2 μl of 0.5 M sodium acetate buffer (pH 4.0) and 7 units of isoamylase (Nakarai Corporation) per 20 μl of the resulting sample solution were added followed by addition of water to adjust the volume to 100 μl (Reaction 1).

At the same time, by using an isoamylase which had been previously inactive by boiling the isoamylase in this reaction solution to treat the same sample, a sample in order to measure oligosaccharide in free state originally contained in the sample was prepared (Reaction 2). After reacting at 37° C. for 16 hours or more, the resultant was boiled for 5 minutes to make isoamylase be inactive, the concentration of branched chains formed by the reaction in relation to Reaction 1 was calculated by modified Park-Johnson method (supra.), and the solution volume corresponding to 10 nmol aliquot of oligosaccharide was dried under vacuum centrifugation. In relation to Reaction 2, the equal volume of the solution volume for Reaction 1 was dried. After this, 2 μl of 1 M Sodium Cyanoborohydride solution (in THF) was added followed by addition of 2 μl of APTS labeling reagent to react at 60° C. in the dark for 90 minutes. 46 μl of water was added to stop the reaction, the resultant was diluted with another water to 40-fold to provide a sample for measurement. The analysis using PACE system 5000 was performed by the same method as described above. The peak area value of each branched chain obtained from Reaction 2 was subtracted from the corresponding area value of that obtained from Reaction 1 to calculate the value of branched chains released by the isoamylase treatment. The area values in relation to the branched chains having 1 to 60 of degree of polymerization were calculated, let the total of these values be 100% and the percentage of the area occupied by each peak was obtained.

In type (vii), the percentage of branched chains having degree of polymerization of 2 to 5 was increased compared to type (i) (see FIGS. 7 and 8). In FIG. 4 of Example, the analysis on branched chains having degree of polymerization of 3 or more was performed, but in the present example, analysis without using maltose quantitative control/mobility marker which would result in overlap with the peak of branched chain having degree of polymerization of 2 was performed, so the peak area of branched chains having degree of polymerization of 2 became clear. Consequently, in type (vii), the peak area of branched chains having degree of polymerization of 2 was also significantly increased compared to that of type (i).

Furthermore, amylopectine of type (ii) had almost the same structure as that of type (i) (FIG. 5), and there was almost no change in the chain-length structure of the amylopectine. On the other hand, in type (vi) and (x) (FIG. 12) which are also glutinous as in type (ii), the percentage of branched chains having degree of polymerization of about 2 to 10 was increased and chains having degree of polymerization of 11 to 25 was decreased compared to type (ii). This indicates that there was a change in amylopectine structure, and it is assumed that this resulted in a decrease in gelatinization peak temperature in DSC and a decrease in viscosity of the solution after gelatinization.

5. The Method for Measuring Amylose Content

The amylose content in the starch of each wheat line was measured. The measuring method is as follows. 25 μl of ethanol per 1 mg of purified starch was added followed by addition of 225 μl of 1 M sodium hydroxide solution and the starch was gelatinized by heating for 10 minutes in boiling water. This gelatinized solution was diluted with water to 10-fold and 50 μl of the resulting solution was taken for measurement. To this, 10 μl of 1 M acetic acid, 20 μl of iodine solution and 920 μl of water was added, mixed well, allowed to stand at 27° C. for 20 minutes, and then the absorbance at 620 nm was measured. Alternately, amylose derived from potato was treated as a sample for creating a calibration curve in the same way, and starch derived from Waxy Corn (the starch does not contain amylose) was treated as a blank in the same way. The absorbance obtained from Waxy Corn was subtracted from the absorbance of each sample and the resulting value was applied to data of calibration curve. In such way, the amylose content of each sample was determined.

6. Degradation of Raw Starch by α-Amylase

The examination on degradability of raw starch due to digestion by α-amylase treatment was performed as follows. A practical method which was improved with reference to "Starch/Related Glucide Experimental Method", pp. 189-192 was used. Each raw starch derived from type (i), (ii), (iii) and (vii) of wheat line was weighed and adjusted to be 1% suspension by adding water. 20 μL aliquots of this suspension were used to provide triplicate samples (I, II and III). 230 up of 0.8 M acetic acid buffer (pH 6.0) was added to I and II and 10 up of 2 M NaOH was added to III. Then they were heated at 50° C. for 5 minutes to provide completely gelatinized samples. The samples were neutralized with 20 μl of 1 M acetic acid and then 200 up of 0.8 M acetic acid buffer (pH 6.0) was added. Then 10 U of α-Amylase (manufactured by Megazyme Corporation) was added to I and III. Equivalent volume of the solution in which the same α-Amylase had been inactive by boiling for 20 minutes was added to II. All samples were reacted with stirring at 40° C. After 12 hours, the reaction solutions were diluted with water to 5-fold and stored at 4° C. to stop the reactions. The oligosaccharide released by α-Amylase treatment was determined by the modified method of the above-mentioned Park-Johnson method. The rate of raw starch digested by amylase was calculated by the following equation.

$$(I-II)/(III-II)*100$$

7. Gelatinization Degree

After gelatinization by heating, the degree of cloudiness of solution during cooling to room temperature and the gelatinization degree were examined. A method which was improved with reference to "Starch/Related Glucide Experimental Method", pp. 189-192 was used. The method is as follows. Each purified starch of type (i), (iii), (iv) and (v) was weighed and adjusted to be 1% suspension by adding water. 20 μL aliquots of this suspension were used to provide triplicate samples (I, II and III), I and II were boiled for 20 minutes and then cooled to room temperature. The degree of cloudiness of each sample at this time was confirmed visually. After this, each sample was stored at 4° C. for 2 hours followed by addition of 230 μl of 0.8 M acetic acid buffer (pH 6.0). 10 μl of 2 M NaOH was added to III followed by boiling for 5 minutes, it was cooled to room temperature and then neutralized with 20 μl of 1 M acetic acid followed by addition of 200 μl of 0.8 M acetic acid buffer (pH 6.0). Then 5 μl of each β-Amylase (manufactured by Sigma Corporation) and Pullulanase (manufactured by Hayashi Protista Chemical Laboratory) was added to I and III. Equal volume of the solution in which the same kind of enzyme had been inactive by boiling for 20 minutes was added to II. All samples were reacted with stirring at 40° C. After 30 minutes, the reaction solution was diluted with water to 5-fold and stored at 4° C. to stop the reaction. The oligosaccharide formed by enzyme treatment was determined by the modified method of the above-mentioned Park-Johnson method. The concentration of oligosaccharide in each sample was calculated and then the gelatinization degree was calculated by the following equation.

$$(I-II)/(III-II)*100$$

8. Viscosity

After gelatinizing the starch derived from each wheat line, the viscosity of the solution when cooled to 60° C. was measured. The measuring method is as follows. Purified starch was weighed and 4% starch suspension was prepared by adding distilled water. It was boiled in boiling water for 20 minutes and stored at 60° C. 100 μl of this gelatinized solution was transferred to a glass tube with inside diameter of 1 mm erected vertically and the time that the tip of the liquid surface required to drop a distance of 5 cm was measured. On the other hand, each starch solution prepared by Waxy Corn (manufactured by Honen Corporation) with concentration of from 2% to 7.5% at intervals of 0.5% was gelatinized and stored in the same way, and the dropping rate was measured similarly to create a calibration curve. For Waxy Corn, at the same concentration, the viscosity at 60° C. after gelatinization was measured by rapid viscoanalyzer, which was used to create a calibration curve. The dropping rate at 60° C. of the starch from each type of wheat was applied to the calibration curve created by using Waxy Corn and then relative viscosity was calculated.

9. Freeze-Thaw Tolerance after Gelatinization

The examination of freeze-thaw tolerance was carried as follows. Water was added to purified starch of each sample to provide 5% of starch suspension. After the starch suspension was gelatinized by boiling for 20 minutes, it was cooled to room temperature and at this point the appearance of gelatinized solution was observed. For the samples which were gotten cloudy and gelled by cooling to room temperature, the evaluation of "high", "medium" or "low" was determined according to the degree. In addition, for the samples which neither cloudiness nor gelation was seen, the evaluation of "no cloudiness" was given. An operation in which these gelatinized solutions or gelled samples were frozen at −80° C. for 1 hour followed by thawing at 25° C. for 30 minutes was repeated 10 times, and then the appearances of each sample was observed. The evaluation of "X>" was given to the samples which had been gelled at which time 10th thawing was completed, the evaluation of "Δ" was given to the samples in which the degree of gelation was small and the evaluation of "◯" was given to the samples in which gelation had hardly seen.

The results of property evaluation for the starch of each type of wheat are summarized in Table 2 below.

TABLE 2

| | Properties of starch | | | | | |
|---|---|---|---|---|---|---|
| Type | Amylose Content | Rate of Degradation by α-Amylase | Gelatinization Degree | Degree of Cloudiness | Relative Viscosity | Freeze-Thaw Tolerance |
| (i) | 26.3% | 34.5% | 47.9% | high | N.T. | X |
| (ii) | 1% or less | 34.4% | N.T. | no cloudiness | 384 | ◯ |
| (iii) | 34.8% | 77.2% | 68.6% | medium | 720 | Δ |
| (iv) | 19.1% | N.T. | 75.9% | medium | N.T. | X |
| (v) | 18.9% | N.T. | 91.5% | medium | 318 | ◯ |
| (vi) | 1% or less | N.T. | N.T. | no cloudiness | 269 | ◯ |
| (vii) | 1% or less | 93.9% | N.T. | no cloudiness | 136 | ◯ |
| (viii) | 18.8% | N.T. | N.T. | low | N.T. | N.T. |
| (ix) | 19.3% | N.T. | N.T. | low | N.T. | N.T. |
| (x) | 1% or less | N.T. | N.T. | no cloudiness | N.T. | N.T. |

As for type (vii), as described above, it is considered that degradability of raw starch is significantly increased because sugar components could not take starch grain structures and then be highly influenced by hydrolase such as α-Amylase. Type (vii) of wheat line based on such sugar components can provide a usage which is completely different from that of conventional wheat in processability or digestive ability in the case of using as foods. Concrete examples include easy-digestive breads, noodles or cakes. Moreover it is preferable as feed grain. In addition, amount of gelatinization energy during processing requires far less compared to the line which forms starch granules. That is to say, cooking at lower temperature is possible and the effect due to heating which may affect other food components can be limited as much as possible. In addition, because it is excellent in freeze-thaw tolerance after gelatinization, it is particularly suitable for food for cold storage or frozen storage. Furthermore, type (vii) of starch has very high water absorbency during starch purification compared to other types. If the amount of water absorption is large, a small amount of it can absorb a large quantity of water when used as a gelling agent. Alternately, preparation in a small amount is also possible in the case of application to jelly-like food. It is possible to apply it to production of resistant starch.

It is commonly known that the amylose content varies depending on the combination of genes of Granule Bound Starch Synthase genes that synthesize it. Meanwhile, as already described, it is known that the amylose content in plants in which all of Wheat Starch Synthase II are deleted is significantly increased (type (iii)), compared to wild type plants. It was assumed from the foregoing that for plants having the same combination of Granule Bound Starch Synthase, the apparent amylose content would increase if one or two of Wheat Starch Synthase II were also deleted. However, the actual results showed that the apparent amylose contents were about the same level (comparison of type (iv) and type (ix), type (v) and type (viii)), or tended to be slightly lower (data not shown).

Regarding retrogradation tolerance (higher "Degree of Cloudiness" means lower tolerance), for plant with the same type of Granule Bound Starch Synthase, the tolerance was increased when Wheat Starch Synthase II was deleted (comparison of type (iv) and type (ix), type (v) and type (viii)) and the relative viscosity of the gelatinized solution was decreased (comparison of type (ii) and type (v), type (vii)).

Based the foregoing, by deleting not only Granule Bound Starch Synthase but also one or more Wheat Starch Synthase II, wheats having the same level of amylose content as in the various conventional low-amylose content wheats and also having increased retrogradation tolerance or decreased viscosity of gelatinized solution after gelatinization, were successfully produced. Furthermore, it was found that this effect was greater when two or more of Wheat Starch Synthase II were deleted. Low-amylose wheats are commonly used as flours for noodles and the improvement in gelatinization and anti-retrogradation properties may bring about improvement effects in these uses. These may also be applied to, for example, dough shells for gyoza, steamed bread, etc.

In addition, as for type (vi) of wheat according to the present invention, in which all of Granule Bound Starch Synthases are deleted and only one of Wheat Starch Synthase II is expressed, the viscosity of this type of wheat is significantly decreased compared to that of type (ii) of wheat. As for type (ii) of wheat, it is known that the viscosity of the gelatinized solution when cooled after gelatinization is small. Type (vi) of wheat shows smaller viscosity than that, which leads to a novel property.

The above data show that a wheat line accumulating the type of starch which could not be screened conventionally by screening of wheat line by the existence of expression of Granule Bound Starch Synthase can be screened.

Although hexaploid wheats which have new starch are invented in the present invention, it is possible to produce tetraploid wheats having the similar effects by applying the present invention. It has been long known that tetraploid wheats may be obtained from the cross-fertilization progeny between hexaploid wheat and tetraploid wheat. Therefore, by cross-fertilizing the wheat according to the present invention that expresses Granule Bound Starch Synthase and Wheat Starch Synthase II in a desired combination with a tetraploid wheat and applying the above screening method to its progeny, a tetraploid wheat may be screened which has Granule Bound Starch Synthase and Wheat Starch Synthase II in a desired combination. Tetraploid wheat includes, for example, durum wheat.

10. Measurement of Content of Maltose or Glucose

The seed samples were previously roughly ground, dried at 135° C. for 2 hours, and the content of water was previously calculated from the change of weight of the samples before and after the drying.

Mature seeds of type (i) and type (vii) of wheat in which embryos had been removed were crushed in liquid nitrogen, 1 ml of DMSO per 10 mg of the crushed powder weight was added to mix well and allowed the mixture to stand at room temperature with occasional stirring. After 1.5 hours, the mixture was centrifuged at 13,000 rpm for 5 minutes and the supernatant was transferred to a new tube. After boiling for 10 minutes, a certain quantity of the mixture was accurately measured and dried in vacuum (DMSO extraction sample).

In addition, dried seeds of type (i) and type (vii) of wheat in which embryos had been removed were crushed in liquid nitrogen, and then 1 ml of 80% ethanol per 10 mg of the powder weight was added. The resultant in sealed tube was boiled for 20 minutes. After cooling, the resultant was centrifuged at 10,000 rpm for 5 minutes and a certain quantity of the resultant was accurately measured and dried in vacuum (Ethanol extraction sample).

In the same way as the method described for the chain-length distribution analysis, 2 µl of 1 M Sodium Cyanoborohydride solution and 2 µl of APTS labeling reagent were added to these samples, reacted at 37° C. in the dark for 4 hours followed by addition of 46 µl of distilled water to stop the reaction. Furthermore the resulting product was diluted with distilled water to 40-fold to provide a sample for measurement. The same analyzer and conditions as those of the method described for the chain-length analysis were used to measure. Based on a calibration curve which had been previously created by using a standard substance, the concentration was calculated from the peak area of glucose and maltose, each sugar concentration per seed dry weight was calculated and the comparison between samples was carried out.

11. Measurement of Sucrose Content

Mature seeds of type (i) and type (vii) of wheat in which embryos had been removed were crushed in liquid nitrogen, and then 1 ml of 80% ethanol per 10 mg of the powder weight was added. The resultant in sealed tube with a lid was boiled for 20 minutes. After cooling, the resultant was centrifuged at 10,000 rpm for 5 minutes and a certain quantity of the supernatant was accurately measured and dried in vacuum. Equal amount of sterilized water as the volume before drying was added to dissolve the sample. Then the sample was filtered by passing it through 0.45 µm filter. Further the sample was filtered by using a ultrafilter membrane with molecular cutoff of 10,000 to provide a solution for sucrose measurement. HP capillary electrophoresis apparatus manufactured by Hewlett Packard Corporation was used for the analysis of sucrose content in the sample, and commercially available buffer (basic anion buffer for HPCE (Agilent Corporation)) and capillary (CE standard capillary (50 µm, 104 cm) (Agilent Corporation)) were used to perform the separation. The sucrose content in the samples was calculated in the light of a calibration curve which had been previously created by using commercially available sucrose and the comparison between samples was carried out.

[Result of Sugar Content Measurement]

It was confirmed that at least 5-fold or more of glucose, at least 10-fold or more of maltose and at least 2-fold or more of sucrose were contained in type (vii) of wheat compared to type (i) wheat which was the same type of wheat used commercially widely. Moreover, these sugars were contained in type (vii) of seed so much level as to be able to feel the sweetness even in mouth, which may be said a novel feature that had not been in conventional type of seed. The increase of sugar content not only allows the wheat of the present invention to use without adding another sugar component during processing it to food, but also allows it to use as raw material in which sugar in itself is provided.

12. Gelatinization Property (DSC)

Each of about 3 mg aliquot of purified starch from each wheat was accurately weighed, 3-fold quantity of water was added over a half day or more such that enough water was contained. This sample was enclosed in a sealed cell, heated from 30° C. to 105° C. at the rate of 5° C./min by differential scanning calorimeter, and then gelatinization start temperature (TO), gelatinization peak temperature (Tp), gelatinization conclusion temperature (Tc) and enthalpy were measured.

In this result, TO was increased in type (ii) which is one parental line of type (vii) compared to type (i) which is a wild type, and TO was decreased in type (iii) which is another parent line. In the contrast to this, type (vii) showed a gelatinization peak temperature further smaller than that of type (iii) which is its parental line. Notwithstanding, enthalpy was larger than that of type (iii), which may be a very characteristic property. Furthermore, it is commonly known that starch of glutinous type in which all three Granule Bound Starch Synthases are deleted (type (ii)) exhibits higher gelatinization peak temperature compared to type (i) which has all three Granule Bound Starch Synthases. Meanwhile, type (vi) has lower gelatinization peak temperature compared to type (i) even though it is the type which does not have amylose. By deleting not only Granule Bound Starch Synthase but also Wheat Starch Synthase II simultaneously, the gelatinization peak temperature and the enthalpy was successfully decreased.

If gelatinization peak temperature in the DSC measurement becomes lower, the gelatinization at lower temperature is possible, which not only may greatly affect the processability, but also allows it to process with materials which are not good to heat. Furthermore, if the gelatinization proceeds at low temperature, the starch becomes susceptible to degradation by amylase and the like, free sugar due to these may lead to further feeling to the sweetness, which may be also considered to give a great effect on the taste.

TABLE 3

| Sample | Glatinization start temperature (TO) | Glatinization peak temperature (Tp) | Glatinization conclusion temperature (Tc) | Enthalpy (ΔH) |
|---|---|---|---|---|
| (i) | 54 | 60.1 | 65.7 | −6.672 |
| (ii) | 57.3 | 62.7 | 70.7 | −9.047 |
| (iii) | 46.1 | 49.7 | 54.9 | −3.238 |
| (vi) | 52.6 | 58.3 | 70.1 | −8.192 |
| (vii) | 43.7 | 47.3 | 52.3 | −6.47 |

13. Measurement of Water Soluble Polyglucan (WSP) Content

Mature seeds in which embryos had been removed were crushed and a fraction which went through 65 μm nylon mesh was used. After the collected fraction was boiled in methanol for 15 minutes, it was centrifuged and precipitation was recovered. The precipitation was further washed with 90% methanol, centrifuged, recovered, dried and the its weight was measured. Approximately 50 mg of the sample was weighed out, 20 μl of water was added per mg sample, and water soluble polyglucan was extracted with stirring at room temperature for 20 minutes. Soluble fraction and insoluble fraction were collected separately after centrifuging at 600×g for 20 minutes. Further extraction with water was carried out on the insoluble fraction, and soluble fraction and insoluble fraction were collected. The first and the second soluble fraction were combined and used in the later process.

The combined soluble fraction was deproteinized by adding trichloroacetid acid (TCA) in a final concentration of 5% and placing it on ice for 3.5 hours. The protein layer was removed after centrifugation at 2,400×g for 10 minutes, 3 fold amount of methanol was added to the supernatant to precipitate the WSP, WSP was collected by centrifugation, dried and its weight was measured.

As for the insoluble fraction, 1050 μl of water was added and suspended, after which 150 μl of toluene was added and stirred for 1 hour for deproteinization. Precipitation was collected by centrifugation at 700×g for 10 minutes. Deproteininzation was carried out two more times, and the finally collected precipitation was washed three times with water, once with methanol, dried in vacuo and had its weight measured. For each sample, the weight of soluble fraction and the weight of WSP were summed as the total sugar weight, and the ratio of the WSP weight to the total sugar weight was calculated (FIG. 14). WSP content in type (viii) was clearly increased compared to type (i), (ii) and (iii).

14. Bakery Foods

Among the wheats according to the present invention, those of type (vii) were used to produce bakery foods. 1.5 mg of water was added per 100 g of harvested mature seeds and mixed well, tempered for 30 minutes, and then milled using Brabender Quadrumat Jr. test mill to obtain wheat flour. The yield rate was 46% by weight. Next, loaf breads were produced using the composition shown in Table 4 and 5 and according to the following production method. Ingredients shown in Table 4 except for shortening were put together and mixed in a mixer at low speed for 1 minute and at high speed for 2 minutes (27° C.). After stopping the mixer, shortening was added and was mixed again at low speed for 1 minute and at high speed for 3 minutes, and the kneaded dough was fermented at 27° C., 75% humidity for 90 minutes. After punching, the dough was fermented again under the same condition for 30 minutes, divided up into pieces of 100 g, rolled up and benched for 20 minutes. After molding using a molder, they were subjected to final proof in a fermentation room of 38° C. and 85% humidity and were then baked (205° C., 20 minutes).

The flavor and texture of the loaf breads produced according to the above conditions were evaluated by 10 panelists. A 5-level evaluation was carried out according to items and evaluation standards set out in table 6, and the average of each item was calculated. The average values were summed up to obtain an overall evaluation of each test area (FIG. 7). The results confirmed that bakery foods that have sweetness and strong flavor such as smell and taste may be produced by using grain flours obtained from the wheat according to the present invention. In addition, it was found that it is preferable to use 0.1 to 60% by mass, more preferably 0.5 to 50% by mass when producing bakery foods.

TABLE 4

| Grain Flour (grain flour indicated in Table 5) | 600 parts by mass |
|---|---|
| Yeast | 12 parts by mass |
| Sugar | 30 parts by mass |
| Salt | 12 parts by mass |
| Skim Milk | 12 parts by mass |

TABLE 4-continued

| | |
|---|---|
| Yeast Food | 0.2 parts by mass |
| Shortening | 30 parts by mass |
| Water | 420 parts by mass |

TABLE 5

| Test Area | Hard Flour | Grain Flour derived from the Wheat according to the Present Invention | Soft Flour |
|---|---|---|---|
| ① | 100 | 0 | |
| ② | 99.99 | 0.01 | |
| ③ | 99.9 | 0.1 | |
| ④ | 99.5 | 0.5 | |
| ⑤ | 99 | 1 | |
| ⑥ | 98 | 2 | |
| ⑦ | 95 | 5 | |
| ⑧ | 90 | 10 | |
| ⑨ | 80 | 20 | |
| ⑩ | 70 | 30 | |
| ⑪ | 60 | 40 | |
| ⑫ | 50 | 50 | |
| ⑬ | 40 | 60 | |
| ⑭ | 30 | 70 | |
| ⑮ | | 80 | 20 |

* Amounts in parts by mass
* Flours obtained by milling with Brabender test mill was used as grain flours derived from the wheat according to the present invention.
* Hard Flour used was Eagle (Nippon Flour Mills Co., Ltd.); Soft Flour used was Heart (Nippon Flour Mills Co., Ltd.).

TABLE 6

| Sensory Evaluation Standards for Loaf Breads | |
|---|---|
| Smell | 5. aromatic and strong fragrance |
| | 4. relatively strong fragrance |
| | 3. some fragrance |
| | 2. no fragrance |
| | 1. unpleasant fragrance |
| Texture | 5. very suave |
| | 4. suave |
| | 3. moderate suaveness |
| | 2. relatively not suave |
| | 1. not suave and remains in the mouth |
| Taste | 5. strong taste and flavory |
| | 4. relatively strong taste |
| | 3. not much taste |
| | 2. no taste |
| | 1. no taste and sour |
| Sweetness | 5. very sweet |
| | 4. relatively strong sweetness |
| | 3. moderate sweetness |
| | 2. very little sweetness |
| | 1. no sweetness |

TABLE 7

Results of Sensory Evaluation

| | Smell | Texture | Taste | Sweetness | Overall evaluation |
|---|---|---|---|---|---|
| ① | 3.0 | 3.3 | 2.5 | 1.7 | 10.5 |
| ② | 2.9 | 3.3 | 2.3 | 1.7 | 10.2 |
| ③ | 3.0 | 3.7 | 2.7 | 2.0 | 11.4 |
| ④ | 3.0 | 3.5 | 2.7 | 2.2 | 11.4 |
| ⑤ | 3.3 | 3.7 | 2.9 | 2.0 | 11.9 |
| ⑥ | 3.5 | 3.9 | 3.1 | 2.3 | 12.8 |
| ⑦ | 3.5 | 4.3 | 3.0 | 2.4 | 13.2 |
| ⑧ | 3.4 | 4.4 | 3.1 | 2.3 | 13.2 |
| ⑨ | 3.8 | 4.6 | 3.5 | 2.5 | 14.4 |
| ⑩ | 3.9 | 4.2 | 3.7 | 3.1 | 14.9 |
| ⑪ | 4.2 | 3.1 | 3.9 | 3.5 | 14.7 |
| ⑫ | 4.2 | 2.2 | 3.8 | 4.1 | 14.3 |
| ⑬ | 4.6 | 1.6 | 4.1 | 4.0 | 14.3 |
| ⑭ | 4.7 | 1.2 | 4.1 | 4.2 | 14.2 |
| ⑮ | 2.8 | 2.9 | 2.3 | 1.5 | 9.5 |

SEQUENCE LISTING

Figure 1A:
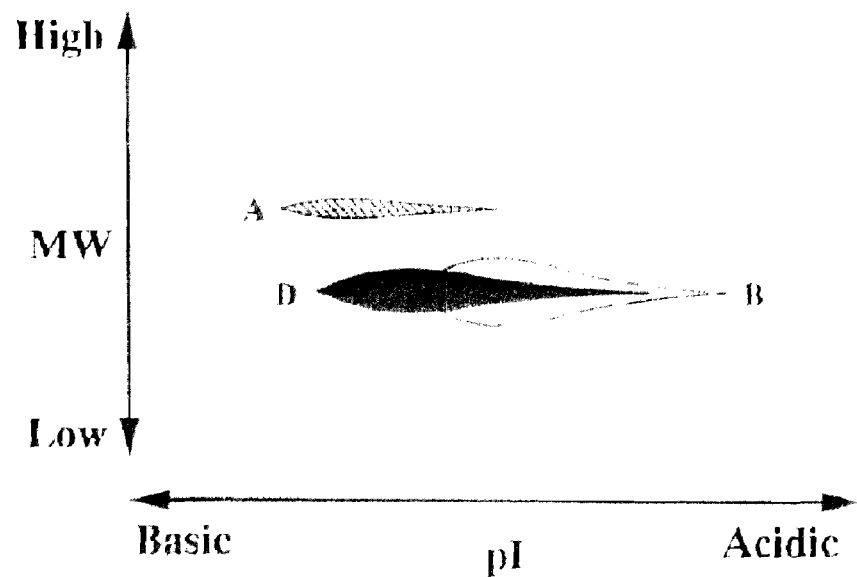
FIG. 1A is a schematic diagram of the migration result obtained by two-dimensional electrophoresis of type (i).
Figure 1B:
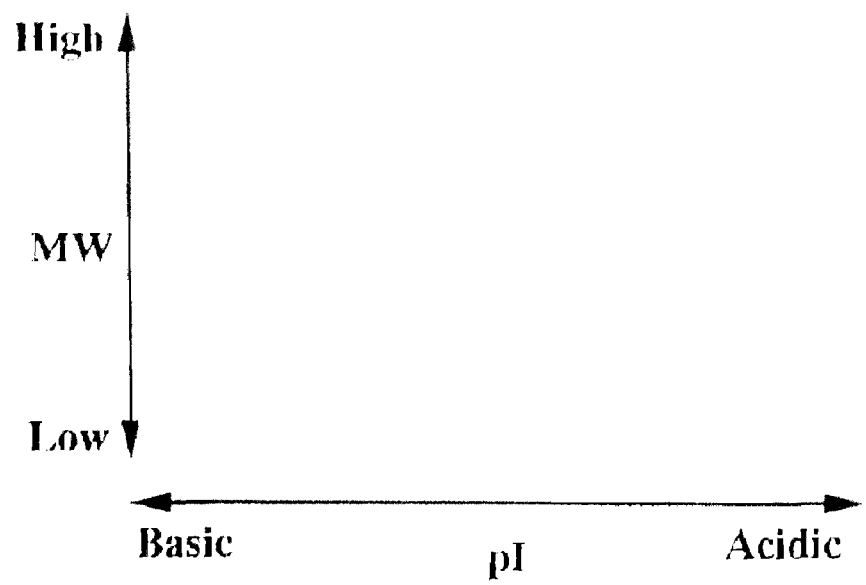
FIG. 1B is the result obtained by two-dimensional electrophoresis of type (vii).
Figure 2:
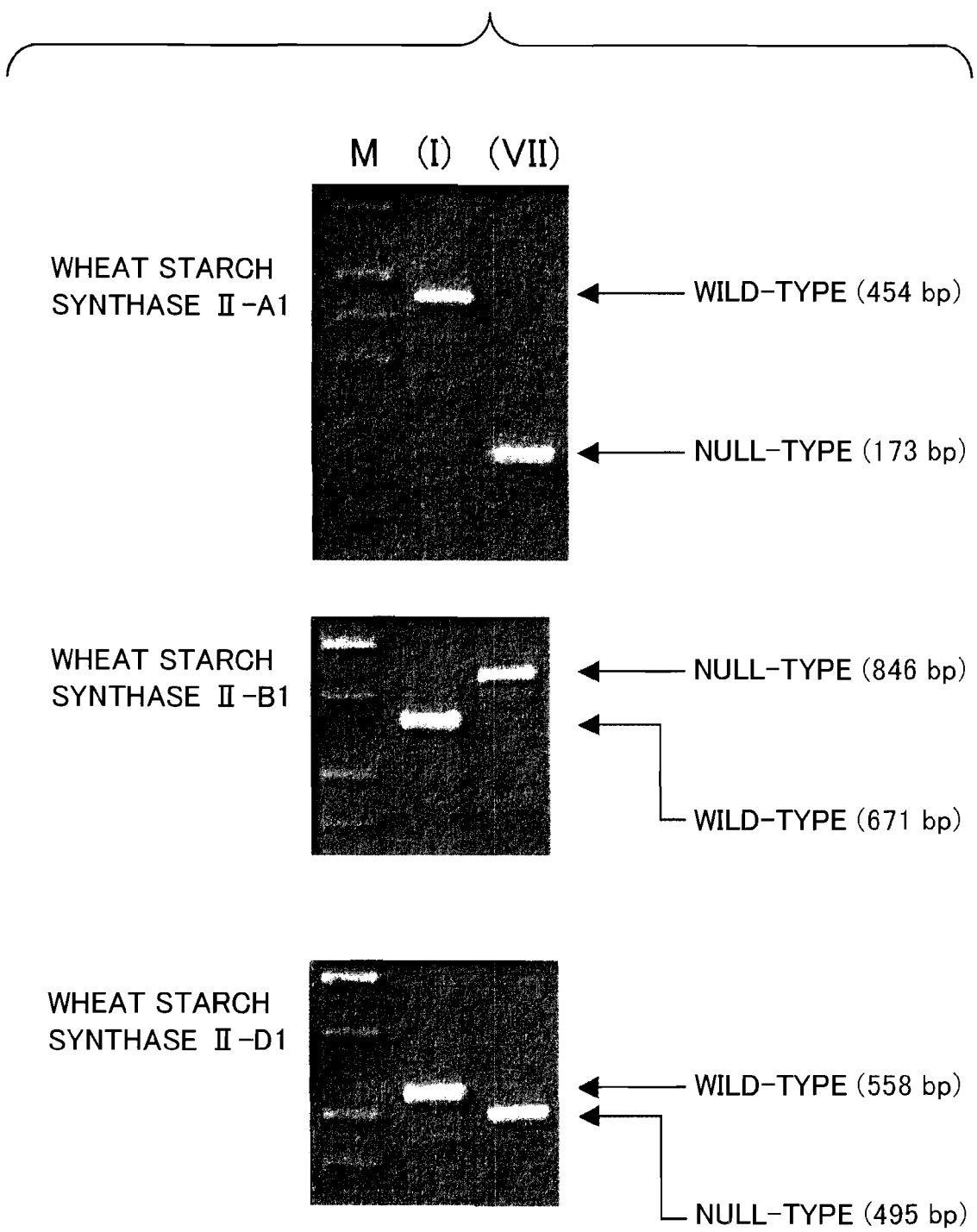
FIG. 2 is the result obtained by performing genotype determination of control variety of type (i) and type (vii) of wheat.
Figure 3:
FIG. 3 is the electron micrograph for a seed produced by type (vii) of wheat line.
Figure 4:
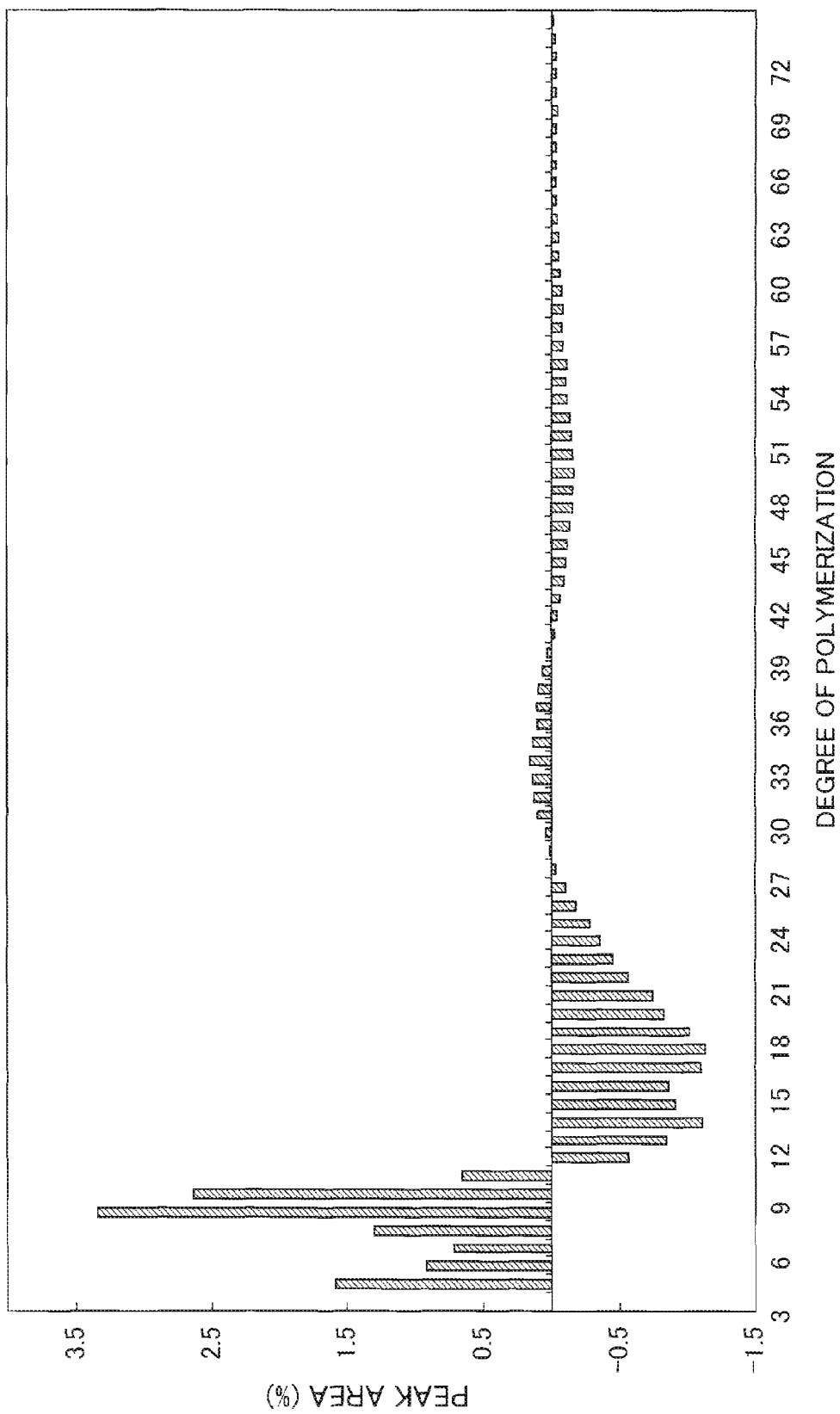
FIG. 4 is the analysis result ((vii)-(i)) of chain-length distribution of side chains which compose the amylopectin in the starch derived from type (vii) line.
Figure 5:
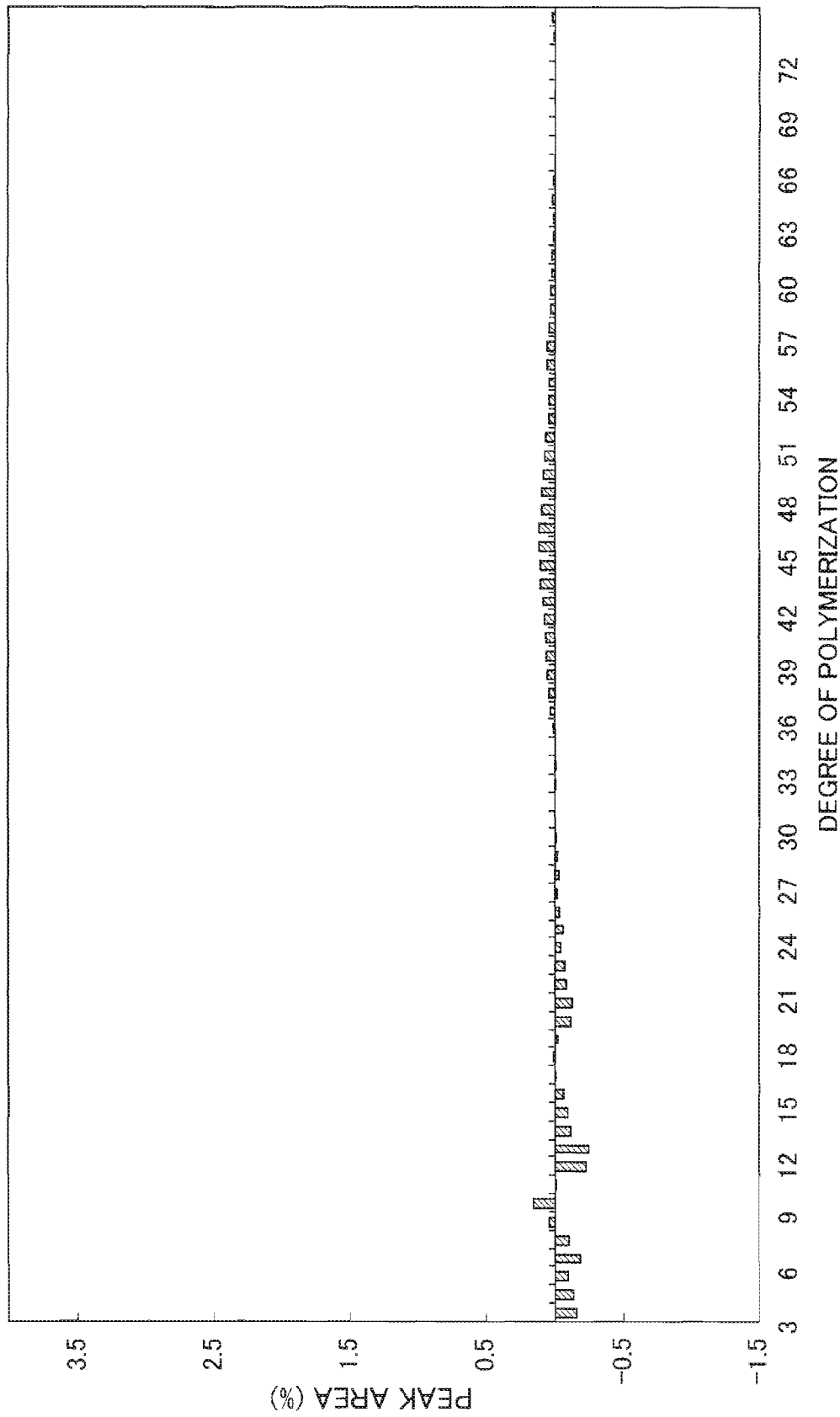
FIG. 5 is the analysis result ((ii)-(i)) of chain-length distribution of side chains which compose the amylopectin in the starch derived from type (ii) line.
Figure 6:
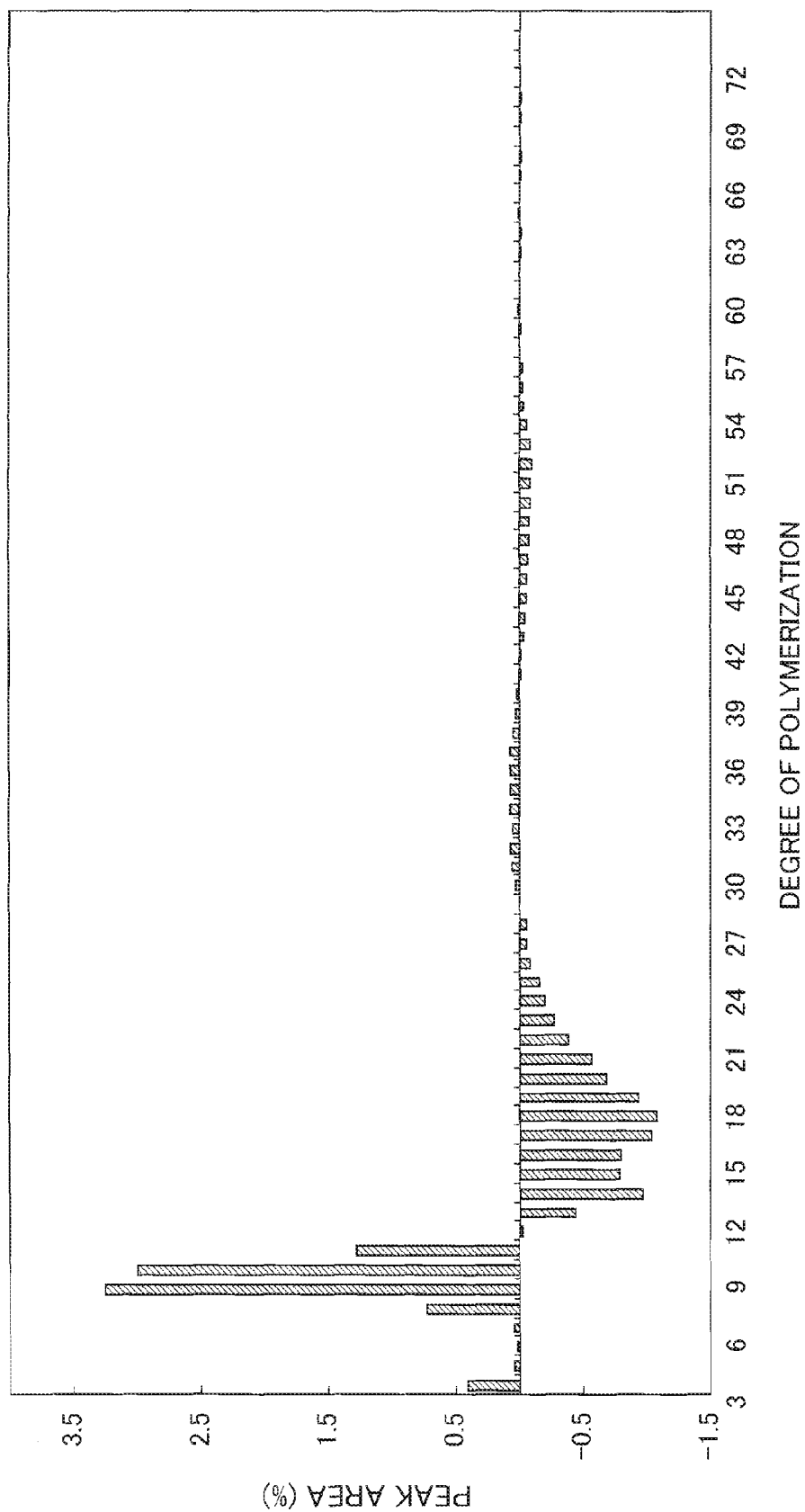
FIG. 6 is the analysis result ((iii)-(i)) of chain-length distribution of side chains which compose the amylopectin in the starch derived from type (iii) line.
Figure 7:
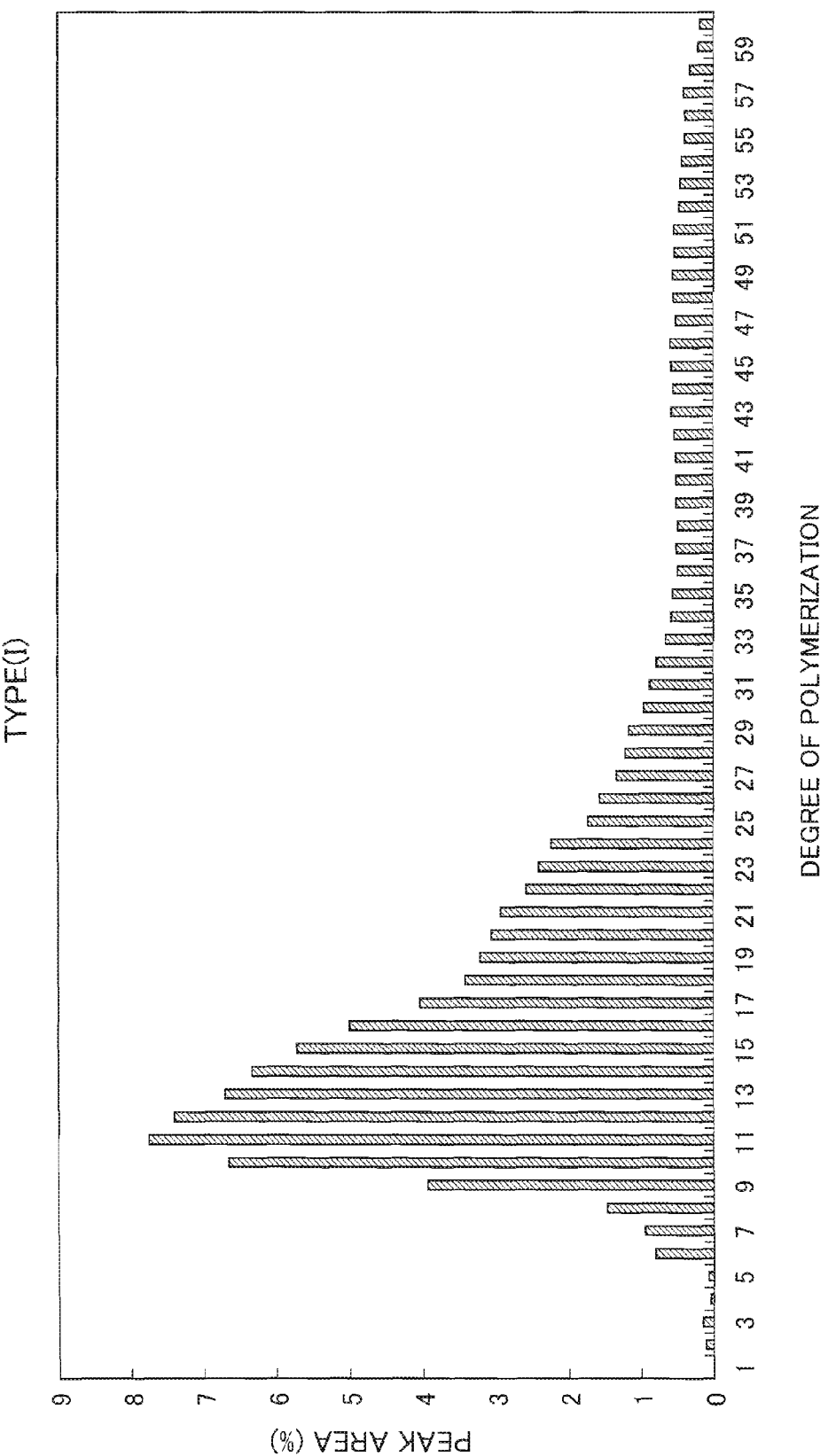
FIG. 7 is the analysis result of chain-length distribution of side chains which compose the amylopectin in the starch derived from type (i) line.
Figure 8:
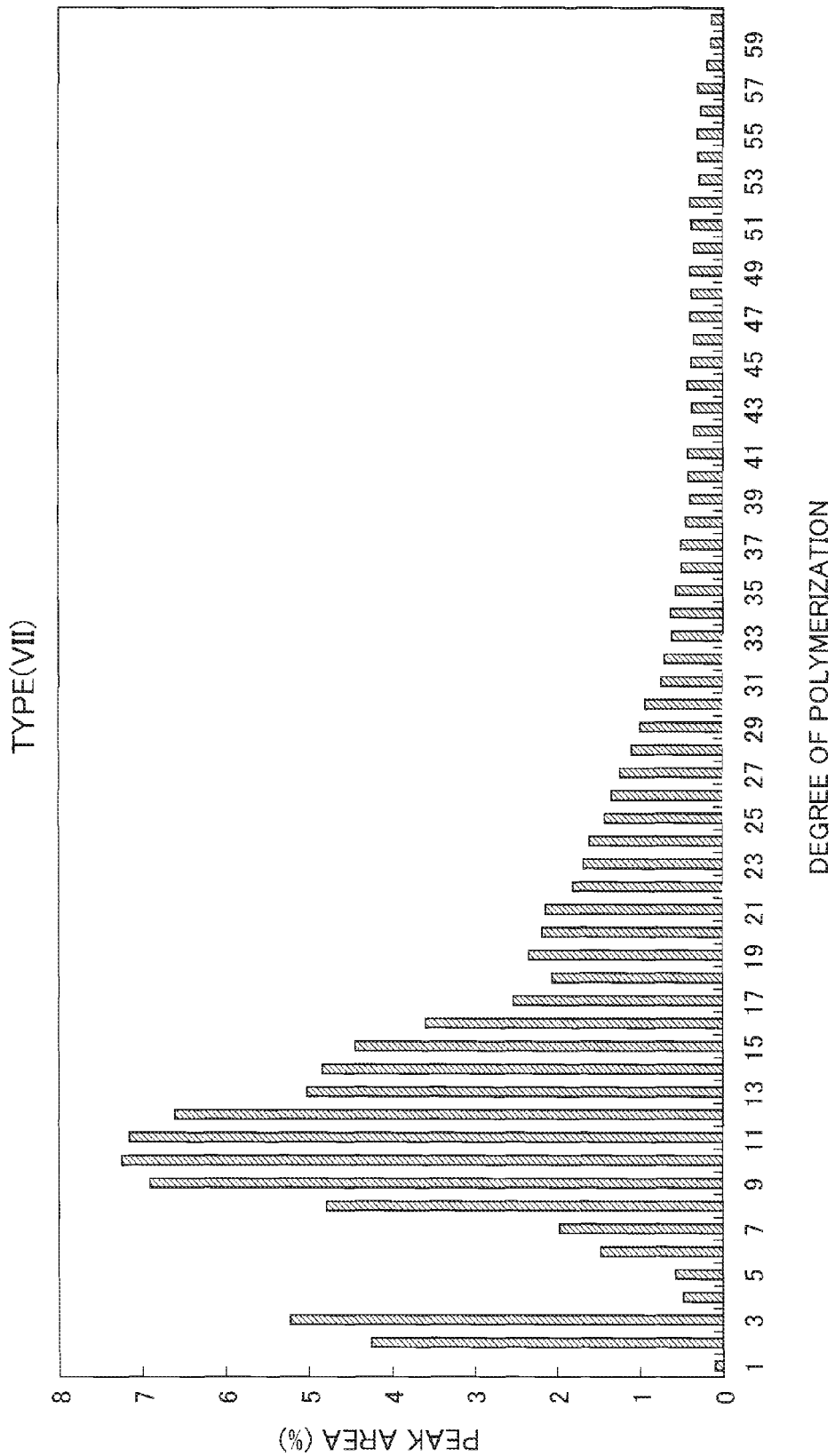
FIG. 8 is the analysis result of chain-length distribution of side chains which compose the amylopectin in the starch derived from type (vii) line.
Figure 9:
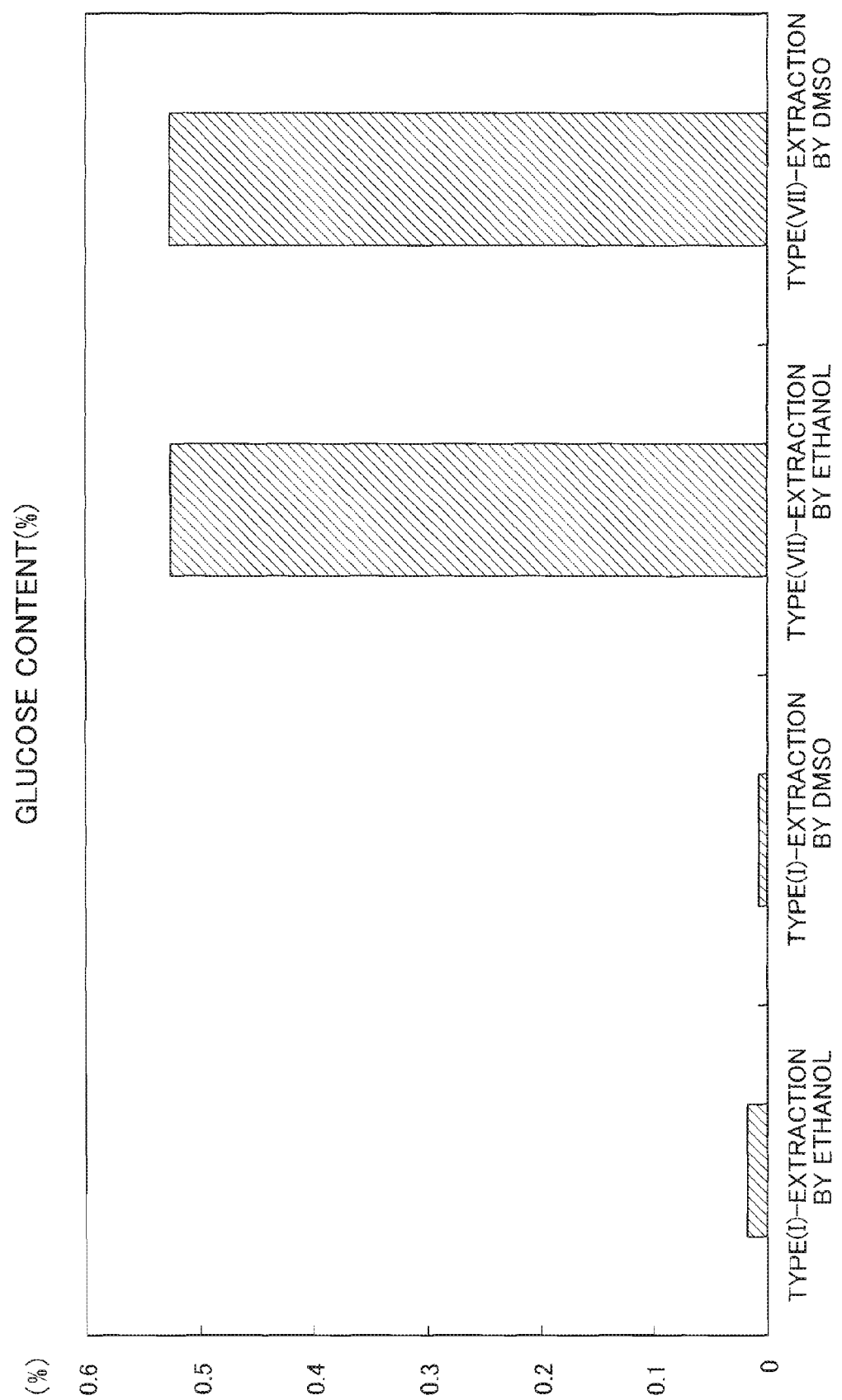
FIG. 9 is a graph for showing glucose content in a mature seed.
Figure 10:
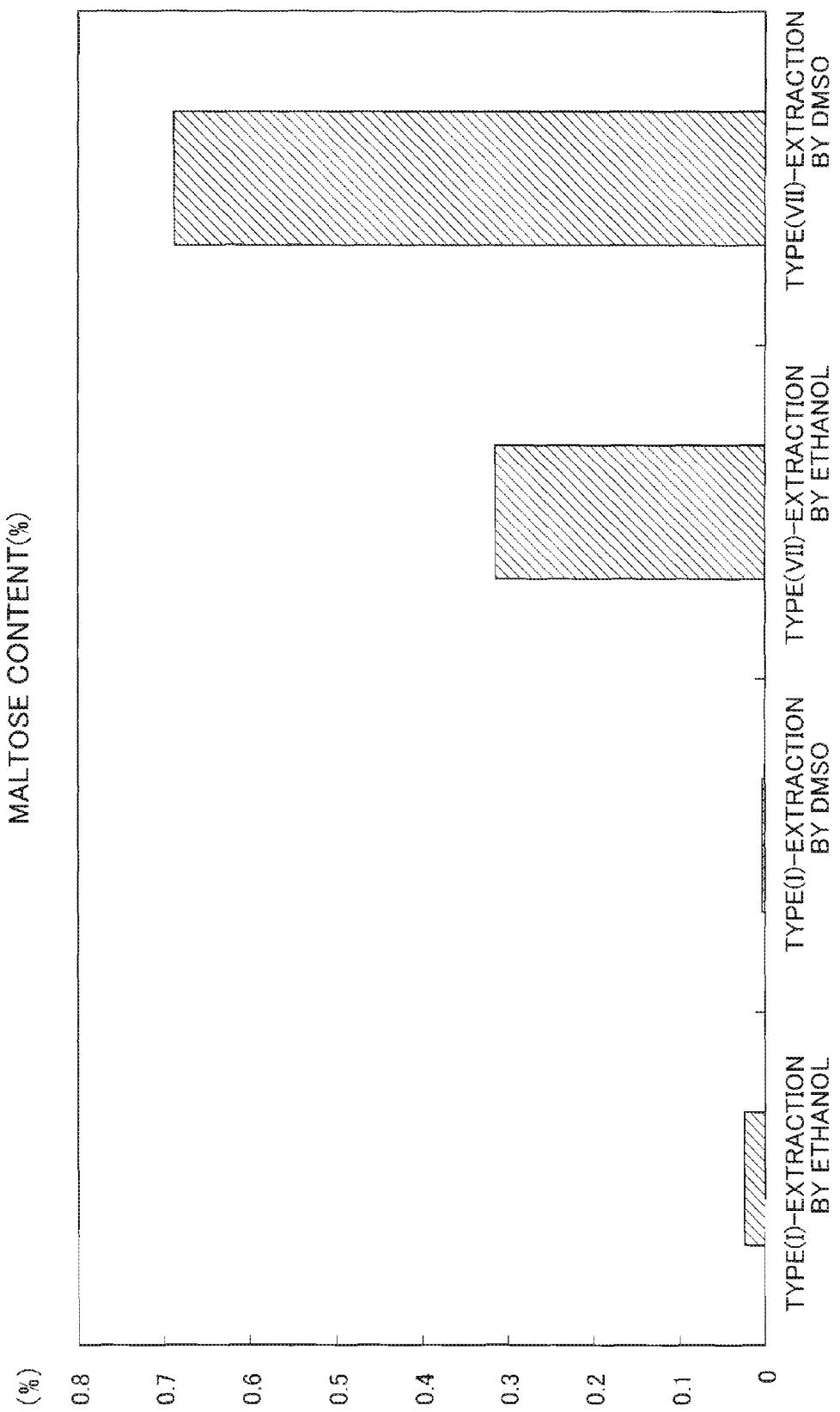
FIG. 10 is a graph for showing maltose content in a mature seed.
Figure 11:
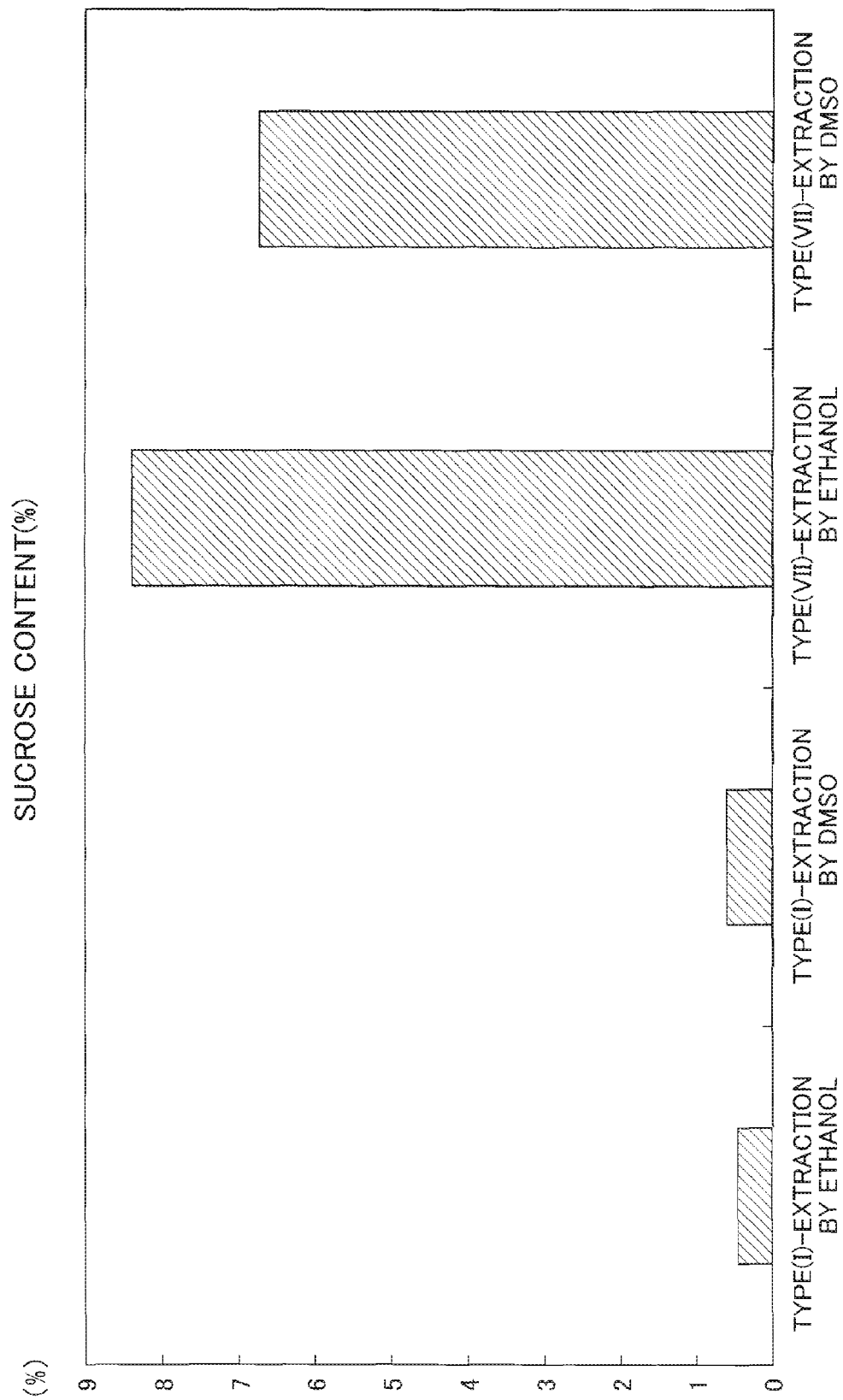
FIG. 11 is a graph for showing sucrose content in a mature seed.
Figure 12:
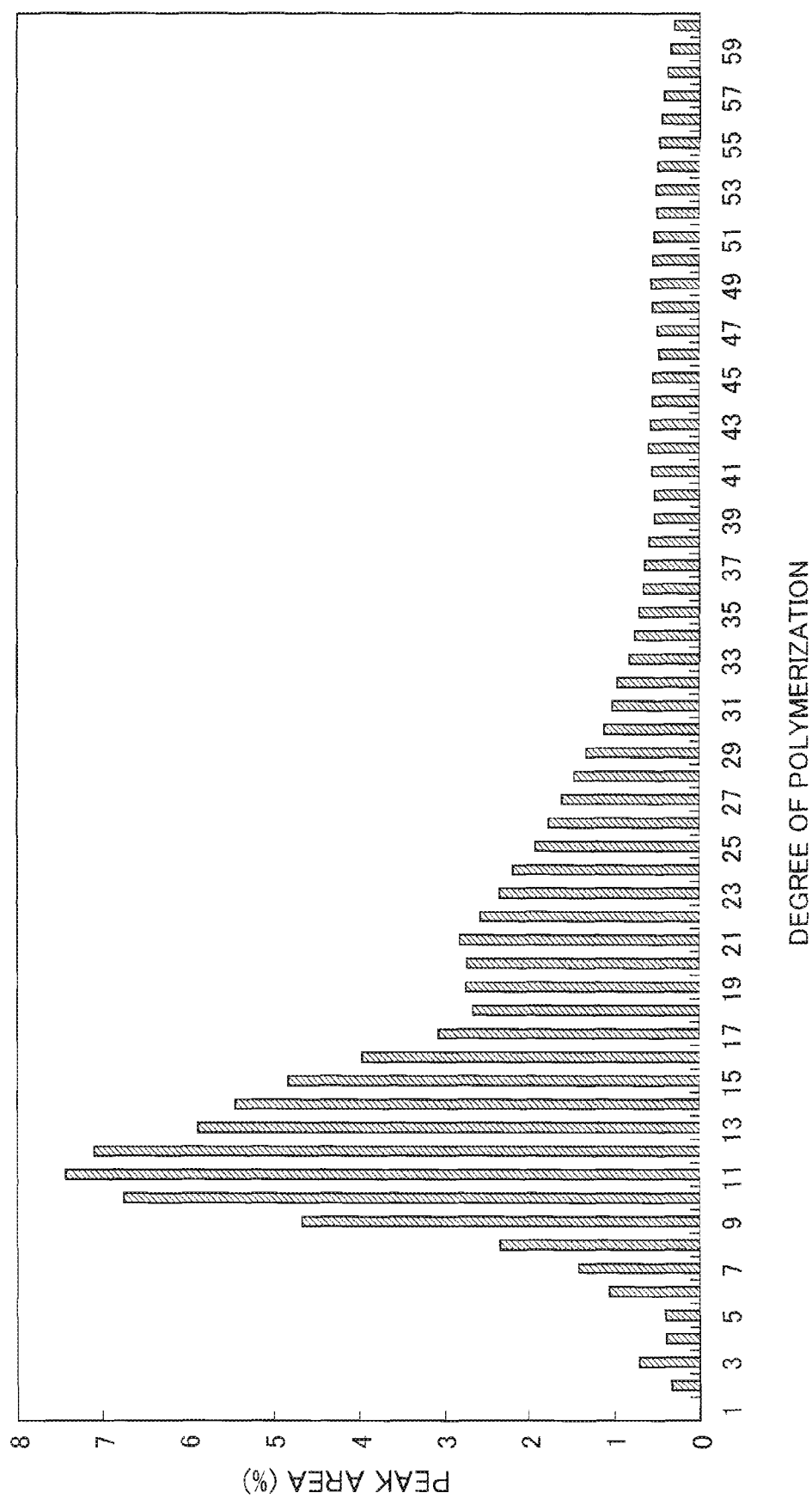
FIG. 12 is the analysis result ((x)-(i)) of chain-length distribution of side chains which compose the amylopectin in the starch derived from type (x) line.
Figure 13:
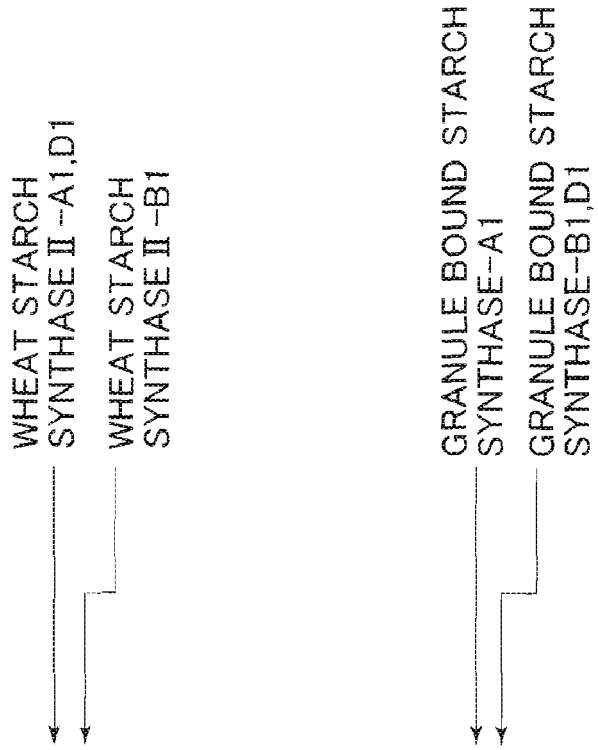
FIG. 13 is the result of electrophoresis by SDS-PAGE.
Figure 14:
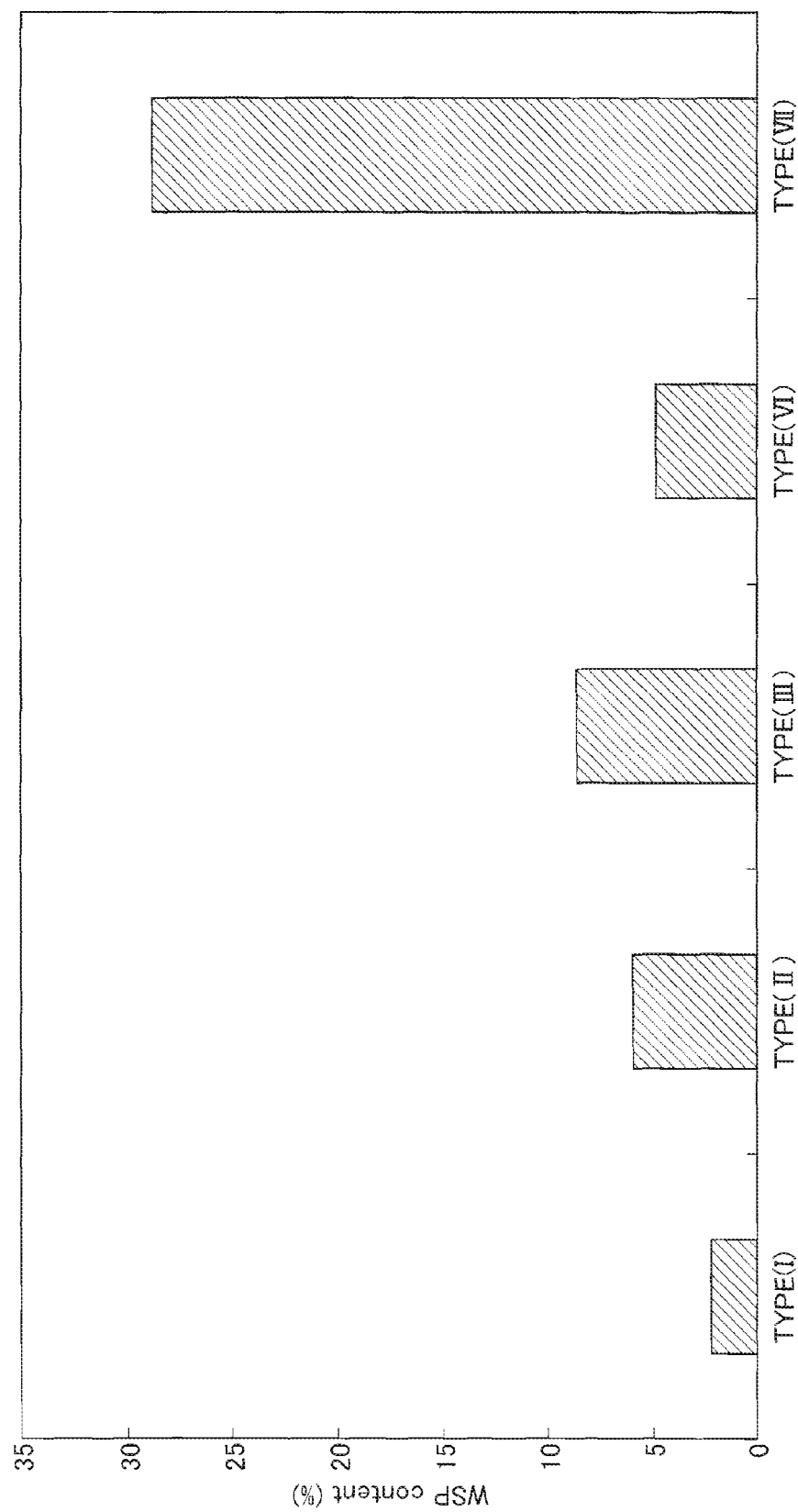
FIG. 14 is a graph for showing water soluble polyglucan content in a mature seed.

```
<160> NUMBER OF SEQ ID NOS: 29

<210> SEQ ID NO 1
<211> LENGTH: 6898
```

<212> TYPE: DNA
<213> ORGANISM: Triticum aestivum

<400> SEQUENCE: 1

```
gggggccgtt cgtacgtacc cgcccctcgt gtaaagccgc cgccgtcgtc gccgtccccc      60
gctcgcggcc atttccccgg cctgaccccg tgcgtttacc ccacagagca cactccagtc     120
cagtccagcc cactgccgcc gcgctactcc ccactcccgc tgccaccacc tccgcctgcg     180
ccgcgctctg ggcggaggac caacccgcgc atcgtaccat cgcccgcccc gatcccggcc     240
gccgccatgt cgtcggcggt cgcgtccgcc gcgtccttcc tcgcgctcgc ctccgcctcc     300
cccgggagat cacgcaggcg ggcgagggtg agcgcgccgc caccccacgc cggggccggc     360
aggctgcact ggccgccgtg gccgccgcag cgcacggctc gcgacggagg tgtggccgcg     420
cgcgccgccg ggaagaagga cgcgagggtc gacgacgacg ccgcgtccgc gaggcagccc     480
cgcgcacgcc gcggtggcgc cgccaccaag gtagttggtt cgttatgact tgctgtatgg     540
cgcgtgcgcc tcgagatcag ctcacgaatt gtttctacaa aacgcacgcg ctcgtgtgca     600
ggtcgcggag cggagggatc ccgtcaagac gctcgatcgc gacgccgcgg aaggtggcgc     660
gccggcaccg ccggcaccga ggcaggacgc cgcccgtcca ccgagtatga acggcacgcc     720
ggtgaacggt gagaacaaat ctaccggcgg cggcggcgcg accaaagaca gcgggctgcc     780
cgcacccgca cgcgcgcccc atccgtcgac ccagaacaga gtaccagtga acggtgaaaa     840
caaagctaac gtcgcctcgc cgccgacgag catagccgag gtcgtggctc cggattccgc     900
agctaccatt tccatcagtg acaaggcgcc ggagtccgtt gtcccagccg agaagccgcc     960
gccgtcgtcc ggctcaaatt tcgtggtctc ggcttctgct cccaggctgg acattgacag    1020
cgatgttgaa cctgaactga agaagggtgc ggtcatcgtc gaagaagctc aaacccaaa     1080
ggctctttcg ccgcctgcag ccccgctgt acaagaagac ctttgggact tcaagaaata    1140
cattggcttc gaggagcccg tggaggccaa ggatgatggc tgggctgttg cagatgatgc    1200
gggctccttt gaacatcacc agaaccatga ttccggacct ttggcagggg agaacgtcat    1260
gaacgtggtc gtcgtggctg ctgaatgttc tccctggtgc aaaacaggca tggacattac    1320
ctcttcagtc tctcttcccg ttgttcataa aactttgctc gaatcactca taagaacaaa    1380
cattgtgttg cataggtggt cttggagatg ttgcgggtgc tctgcccaag gcttggcaa     1440
agagaggaca tcgtgttatg gtactgcagg cttttcactta actctgttga gtccatatgt    1500
tcgaataata tcagtgattg gcataatgtt attaagtgca agacatgaaa gtgttcttct    1560
gttagagtat ttcatagcca accctggagg ttaggttgtt ggggcctact gggtgcggga    1620
gggggtttgc aaaaagtggt ggttagcagt cggatttcac aaataaggag gctgataacc    1680
acgccatcag tgaagggaat gagtgtcggg tacccgatcg accgttttgc ccgacgtcag    1740
gtttaccctgc cctgtagatc cgaataagta gttcctatcc tcagttaagt accaaatatc    1800
gccagcaccc gtgtgtgtat ttatagtact ggatgatcaa tttatcaaca tttccggtta    1860
atggttgcta tcatattcac tgtaattgtt agtaaacagt ggatgtttgt aatgtagatg    1920
atggctaaat gtatgttgtc aagctttcat tttaaagaaa attttattgg gagctagttt    1980
tcgggtttgg ttagagccac caaaacccca gaatttttgg gagttggctt gtgacagagg    2040
gttttgggga gttaactttc gggattcagt tagagacgct cttactagtt ccagtaaaga    2100
gtaaactatt ttctgcagtc atcccaattg ttctgtagaa attaaaagta gaaaatagtt    2160
gtggtatcat ataaaccata tattattcaa aatctagaat catggacttg gctagacttt    2220
gatgatctga aattttaaat ttgatgataa ttgagaaatg atcctttcta tcttaggttg    2280
```

```
tggtaccaag gtatgggac  tatgaggaag cctacgatgt cggagtccga aaatactaca   2340
aggctgctgg acaggtaagc gaaaatgcaa tcaaagggga gctgaaattt caatgcttac   2400
tatcataata aatcaattt  aagtaaaaaa atttgtcctg caggatatgg aagtgaatta   2460
tttccatgct tatatcgatg gagttgattt tgtgttcatt gacgctccta tcttccgaca   2520
ccgtcaggaa gacatttatg ggggcagcag acaggttaat tttctatatg ttggtgtttg   2580
attgcactga taaactgaga ataagccaag gcctactgac tggcatatga ttacacattt   2640
tattttttca ggaaattatg aagcgcatga ttttgttctg caaggccgct gtcgaggtat   2700
cctctccaac tcaattgaca acctattacc actatacaat tatgtgtatg catgtatttc   2760
aacagatacg taatctccct tgtgaagtgt atatatacta ataacatttc aatacctcac   2820
atgcacattt ggtcaagcgt tatgatttaa cttctgataa tctattgcac tgatgaacaa   2880
taatattgat gatccttgtt acttcatcgt tatgttatg  ttctcttcac cggcgcattg   2940
attttggaaa tagcatttcc acctgccaca acaataata  tatactccta ctttcatcca   3000
atgtagatat tttcgcactt ggcatatcat cccattaaat attattggtc catcattttt   3060
attcctctat aatttgcagg ttccttggca cgttccatgc ggcggtgtcc cttatgggga   3120
tggaaatctg gtgtttattg caaatgattg gcacacggca ctcctgcctg tctatctgaa   3180
agcatattac agggaccatg gtttgatgca gtacactcgg tccattatgg tgatacataa   3240
catcgcgcac caggttcctt ttctcctaat cttgtttttt ctctagtctc tactattcac   3300
tccacattgt ttgaggaaac taaaggggtt gcaaaattat gatggcttat gaaagttatg   3360
gaggtaaatg catcagtggt gcttgaactt gtcacgcatg ttcactttgg tgcttacagt   3420
tgtagactac ggaaaactgg tgcaaaaact tggctattgt gtgcaatacg gtgtattttc   3480
cgtatgtagg gtcaaatgtt gcctatgtgg cattgtattc ccgtctatag atgttagacc   3540
gtgcctacat cgccattggg cccacacact ccctattaca tgtgggaccc acttgtcagc   3600
ctatgacata aataaaatgg aaatttataa taaaaatgat ggcctggggt cttgaaaatg   3660
ggacctcgca ggtatgccgc tagccagcac gccctaatca ttaatcccct atgcacttca   3720
gtatgtgtgt gtctgtgtgt ggagtcgggg gggggggggg tatgtattct tatatccttt   3780
gctctaaggc tatcattggc gtgctagcac cgccgggtct ccatcaacac cgacatcatc   3840
cacgacccca tccagctctt cctcaacaag cccacctcca gcctcaactc gggcagcacc   3900
ttcatggtgg cctaggtgct ctgcaccatc gctcgaagtg gcaacgtcgt tgtcatgacc   3960
atccaccaac ccaacacgca aaatcctcaa catcatttga cagtgagcat gcccctcttg   4020
tcatttcccc ctcataccca aacctgtctc gataaccctt ggagctgcac aagttgtgac   4080
catcgcctgc gtcgctgcac aacgcctgac ctagccggac cattatagaa gcctgccttg   4140
ggagcccata cctccctgca catcctcctc tttccccata gaccgtgccg ccatcgcaaa   4200
tcgacttctc ctctcctcct tctcctgctc tggccgtttt ccccgccgcg aagctgcaat   4260
ccatggcgag ttggccatgg ccctattccc caattgctcg cactaggagg tcctccttga   4320
agcctagcac ctttccccct cactaattgc aagttgggga gccctcacg  agctccctac   4380
attggccgta gtcgcctgcc gcctcaactc tggtccagac ctcgttcccg tggcctcgac   4440
gacatctcct cgacctccca ttccacacgc ggcctggaga ggatcaccgc atgttcatcc   4500
atccgacccg aatcatcata gaaccaacgc cagagaggtc atcccgacga cgtcgcactg   4560
ttcctctatt tcccccaagc tgtgtcgcgt cataatataa gacgggcttg tttgtatctc   4620
tagggttcat cgggttcaat ggctagctca tgcatggacc tgactttagg tcccaggttc   4680
```

```
gaacccccgc gtgcacataa tttatttgct atttatttct cctatctact aataagtggg    4740
acccacacat catactaagc ccttttgtc tcttgcctgc tgataagtgg gacccacacg    4800
caatacttag ccagagagag aacatgagct tgttggtgcc gcgttggcaa gccacgccag    4860
cagtcttaac ggctacaaac agaggatatg tgtcacatc aacgtgcaga gcgtttacga    4920
atggaaagtg tactatatgc acacaagagc cagagccagg tttttgcacc agttttttgt    4980
attctacaac tgcgagcacc aaagtgtaca tgccgaacca aagtgaacac ggcgagtcca    5040
ttcttttctg gtacgatggg tggctcaaag acaccccaat agaagctatc acctcggaca    5100
ttgccaattg ggtgccgaac tacattaaag tggcaaggtc agttgattgc gctatgtgtt    5160
ggatcaggga cataaacgat tccataaata ttgcaatgtt cattcaaatt cttaacattt    5220
gcgaggcgct tcatgatttc catctccctc atatcagaga catttggtcg tgtacactaa    5280
atttctcagg tcacttctcg tctaaatccg catatgtagc tcacttcaat gacttgactt    5340
tggtccagct aacgccattt ggcgctcttg ggcccctttg cgtagcaatt ttttcatatg    5400
gctcgctccg cgcaatagga tttggatcac gggcagacgc gctagatgag gtcttccaca    5460
caatgaacat tgcgttcttt gctctgctct tccagaagac acttgtgatt ttattacgag    5520
ttgtgccata gatgccggtg ggtttcagct aggaacaggg tgtcaccttc ggacaagaag    5580
aagttgcata gtttggtcgt cttaactgct tggtcgattt ggaaggagca caacaacagt    5640 cttttgaaggc aaagctaatt ccctcgatca agttattaga cggatcaaat gtggtacagt    5700
gccatggcta gttgcttgga gtcacttta agctaggtcg cttgccatca cgctttgtgt    5760
taagcgcttg gggtcgcttt tgctcaattt gtattttgtt gttatgtgtt tttagttatg    5820
tagcctgaac tttctggact tagttttttc ctctataatg atcacatgct ttggtcagtt    5880
attcctttct tgggtactcc gttgggctaa ttctttctct tgattgatgt tgtatatgca    5940
gggccgtggc ccagtagatg aattcccgtt caccgagttg cctgagcact acctggaaca    6000
cttcagactg tacgaccccg tgggtggtga gcacgccaac tacttcgccg ccggcctgaa    6060
gatggcggac caggttgtcg tggtgagccc cgggtacctg tgggagctca agacggtgga    6120
gggcggctgg gggcttcacg acatcatacg gcagaacgac tggaagaccc gcggcatcgt    6180
caacggcatc gacaacatgg agtggaaccc cgaggtggac gtccacctcc agtcggacgg    6240
ctacaccaac ttctccctga gcacgctgga ctccggcaag cggcagtgca aggaggccct    6300
gcagcgcgag ctgggcctgc aggtccgcgc cgacgtgccg ctgctcggct tcatcggccg    6360
cctggacggg cagaagggcg tggagatcat cgcggacgcc atgccctgga tcgtgagcca    6420
ggacgtgcag ctggtcatgc tgggcaccgg ccgccacgac ctggagagca tgctgcggca    6480
cttcgagcgg gagcaccacg acaaggtgcg cgggtgggtg gggttctccg tgcgcctggc    6540
gcaccggatc acggcgggcg ccgacgcgct cctcatgccc tcccggttcg agccgtgcgg    6600
gctgaaccag ctctacgcca tggcctacgg caccgtcccc gtcgtgcacg ccgtcggcgg    6660
gctgagggac accgtgccgc cgttcgaccc cttcaaccac tccggcctcg ggtggacgtt    6720
cgaccgcgcc gaggcgcaca agctgatcga ggcgctcggg cactgcctcc gcacctaccg    6780
ggactacaag gagagctgga ggggcctcca ggagcgcggc atgtcgcagg acttcagctg    6840
ggagcatgcc gccaagctct acgaggacgt cctcctcaag gccaagtacc agtggtga     6898
```

<210> SEQ ID NO 2
<211> LENGTH: 799
<212> TYPE: PRT
<213> ORGANISM: Triticum aestivum

<400> SEQUENCE: 2

```
Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Pro Pro
            20                  25                  30

Pro His Ala Gly Ala Gly Arg Leu His Trp Pro Pro Trp Pro Gln
            35                  40                  45

Arg Thr Ala Arg Asp Gly Gly Val Ala Arg Ala Ala Gly Lys Lys
50                  55                  60

Asp Ala Arg Val Asp Asp Ala Ala Ser Ala Arg Gln Pro Arg Ala
65                  70                  75                  80

Arg Arg Gly Gly Ala Ala Thr Lys Val Ala Glu Arg Arg Asp Pro Val
                85                  90                  95

Lys Thr Leu Asp Arg Asp Ala Ala Glu Gly Ala Pro Ala Pro Pro
            100                 105                 110

Ala Pro Arg Gln Asp Ala Ala Arg Pro Pro Ser Met Asn Gly Thr Pro
            115                 120                 125

Val Asn Gly Glu Asn Lys Ser Thr Gly Gly Gly Ala Thr Lys Asp
130                 135                 140

Ser Gly Leu Pro Ala Pro Ala Arg Ala Pro His Pro Ser Thr Gln Asn
145                 150                 155                 160

Arg Val Pro Val Asn Gly Glu Asn Lys Ala Asn Val Ala Ser Pro Pro
                165                 170                 175

Thr Ser Ile Ala Glu Val Val Ala Pro Asp Ser Ala Ala Thr Ile Ser
            180                 185                 190

Ile Ser Asp Lys Ala Pro Glu Ser Val Val Pro Ala Glu Lys Pro Pro
            195                 200                 205

Pro Ser Ser Gly Ser Asn Phe Val Val Ser Ala Ser Ala Pro Arg Leu
            210                 215                 220

Asp Ile Asp Ser Asp Val Glu Pro Glu Leu Lys Lys Gly Ala Val Ile
225                 230                 235                 240

Val Glu Glu Ala Pro Asn Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Trp Ala Val Ala Asp Asp Ala
            275                 280                 285

Gly Ser Phe Glu His His Gln Asn His Asp Ser Gly Pro Leu Ala Gly
            290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
            325                 330                 335

Leu Ala Lys Arg Gly His Arg Val Met Val Val Pro Arg Tyr Gly
            340                 345                 350

Asp Tyr Glu Glu Ala Tyr Asp Val Gly Val Arg Lys Tyr Tyr Lys Ala
            355                 360                 365

Ala Gly Gln Asp Met Glu Val Asn Tyr Phe His Ala Tyr Ile Asp Gly
370                 375                 380

Val Asp Phe Val Phe Ile Asp Ala Pro Ile Phe Arg His Arg Gln Glu
385                 390                 395                 400

Asp Ile Tyr Gly Gly Ser Arg Gln Glu Ile Met Lys Arg Met Ile Leu
            405                 410                 415
```

Phe Cys Lys Ala Ala Val Glu Val Pro Trp His Val Pro Cys Gly Gly
              420                 425                 430

Val Pro Tyr Gly Asp Gly Asn Leu Val Phe Ile Ala Asn Asp Trp His
              435                 440                 445

Thr Ala Leu Leu Pro Val Tyr Leu Lys Ala Tyr Tyr Arg Asp His Gly
450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
              485                 490                 495

His Tyr Leu Glu His Phe Arg Leu Tyr Asp Pro Val Gly Gly Glu His
              500                 505                 510

Ala Asn Tyr Phe Ala Ala Gly Leu Lys Met Ala Asp Gln Val Val Val
              515                 520                 525

Val Ser Pro Gly Tyr Leu Trp Glu Leu Lys Thr Val Glu Gly Gly Trp
              530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Val His
              565                 570                 575

Leu Gln Ser Asp Gly Tyr Thr Asn Phe Ser Leu Ser Thr Leu Asp Ser
              580                 585                 590

Gly Lys Arg Gln Cys Lys Glu Ala Leu Gln Arg Glu Leu Gly Leu Gln
              595                 600                 605

Val Arg Ala Asp Val Pro Leu Leu Gly Phe Ile Gly Arg Leu Asp Gly
              610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
              645                 650                 655

Ser Met Leu Arg His Phe Glu Arg Glu His His Asp Lys Val Arg Gly
              660                 665                 670

Trp Val Gly Phe Ser Val Arg Leu Ala His Arg Ile Thr Ala Gly Ala
              675                 680                 685

Asp Ala Leu Leu Met Pro Ser Arg Phe Glu Pro Cys Gly Leu Asn Gln
690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
              725                 730                 735

Leu Gly Trp Thr Phe Asp Arg Ala Glu Ala His Lys Leu Ile Glu Ala
              740                 745                 750

Leu Gly His Cys Leu Arg Thr Tyr Arg Asp Tyr Lys Glu Ser Trp Arg
              755                 760                 765

Gly Leu Gln Glu Arg Gly Met Ser Gln Asp Phe Ser Trp Glu His Ala
              770                 775                 780

Ala Lys Leu Tyr Glu Asp Val Leu Leu Lys Ala Lys Tyr Gln Trp
785                 790                 795

<210> SEQ ID NO 3
<211> LENGTH: 6811
<212> TYPE: DNA
<213> ORGANISM: Triticum aestivum

<400> SEQUENCE: 3

```
gggggccgtt cgtacgtacc caccCctcgt gtaaagccgc cgccgtcgtc gccgtccccc    60
gctcgcggcc atttcctcgg cctgaccccg tgcgtttacc ccacacagag cacactccag   120
tccagtccag cccactgccg cgctactccc cactcccact gccaccacct ccgcctgcgc   180
cgcgctctgg gcggaccaac ccgcgcatcg tatcacgatc acccaccccg atcccggccg   240
ccgccatgtc gtcggcggtc gcgtccgccg cgtccttcct cgcgctcgcg tccgcctccc   300
ccgggagatc acggaggagg acgagggtga gcgcgtcgcc accccacacc ggggctggca   360
ggttgcactg gccgccgtcg ccgccgcagc gcacggctcg cgacggagca gtggccgcgc   420
gcgccgccgg gaagaaggac gcggggatcg acgacgccgc cccgcgagg cagccccgcg    480
cactccgcgg tggcgccgcc accaaggtag ttagttatga ccaagttatg acgcgtgcgc   540
gcgccttgag atcatcgtcg tctcgctgac aaattgttta tacaaaacgc acgcgcgcgc   600
gtgtgtgcag gttgcggagc ggagggatcc cgtcaagacg ctcgatcgcg acgccgcgga   660
aggtggcgcg ccgtccccgc cggcaccgag gcaggaggac gcccgtctgc cgagcatgaa   720
cggcatgccg gtgaacggtg aaaacaaatc taccggcggc ggcggcgcga ctaaagacag   780
cgggctgccc gcacccgcac gcgcgcccca gccgtcgagc cagaacagag taccggtgaa   840
tggtgaaaac aaagctaacg tcgcctcgcc gccgacgagc atagccgagg tcgcggctcc   900
ggatcccgca gctaccattt ccatcagtga caaggcgcca gagtccgttg tcccagccga   960
gaaggcgccg ccgtcgtccg gctcaaattt cgtgccctcg gcttctgctc ccgggtctga  1020
cactgtcagc gacgtggaac ttgaactgaa gaagggtgcg gtcattgtca aagaagctcc  1080
aaacccaaag gctctttcgc cgcctgcagc accgctgtat aacaagacc tttgggactt   1140
caagaaatac attggtttcg aggagcccgt ggaggccaag gatgatggcc gggctgttgc  1200
agatgatgcg ggctccttcg aacaccacca gaatcacgat tccgggcctt tggcagggga  1260
gaacgtcatg aacgtggtcg tcgtggctgc tgaatgttct ccctggtgca aaacaggcat  1320
ggacattacc tcttcagtgt ctttttttctc tctgttcata aaacctggct tgaattactc  1380
ataagaacaa acgttgtgtt gcataggtgg tcttggagat gttgccggtg cttttgcccaa 1440
ggctttggcg aagagaggac atcgtgttat ggtaccacat gctttcattt aactctgttg  1500
aatccatatg ttcgaataat atcagtgagc agtataatgt tattaagtgc aagacatgaa  1560
agtgttcttc tgttatagag tatttcatag ccaaccctgg aggttaggtt gttggggcct  1620
actgggtgtg ggaggggtt tgaaaaaagt gttggttagc agtcggattt cacaaagaac   1680
gctgataacc acgccatcag tgaagggaat gaatgtcggg tacccgatcg accgttttgc  1740
ccgacgtcag gttacccgc cctgtaggtc cgaataagta gttcctatcc tcagttaagt   1800
accaaatatc ggcagcgccc gtgtgtgtat ttatagtact ggatgatcaa tttatcaaca  1860
ttttcagtta atggttgcta tcatattcac tgtaattgtt agtaaacagt ggatgtttgt  1920
aatgtagatg atggctaaat gtatgttgtc aagctttcat ttcaatgcaa tttttattgg  1980
gagctagttt tggggttcgg ttagagccac caaaacccca gaattctgg gagttggctt    2040
gtgagagagg gttttggcga gttgacttc gggattcagt tagagacgct cttactagtt   2100
ccagtaaaga agtaaactat tttctgcaga catcccaatt attctgtaga aattagaagt  2160
agaaaatagt tatggtatca tataaccata tattattcaa aatctagaat catggacttg  2220
gctagacttt gatgatctga aattttaaat ttgatgataa ttgagaaatg atcctttcta  2280
tcttaggttg tggtaccaag gtatggggac tatgaggaag cctacgatgt cggagtccga  2340
aaatactaca aggctgctgg acaggtaagc gaaaatgcaa tcaaagggga gctgaaattt  2400
```

| | |
|---|---|
| caatgcttac tatcataata aatcaatttt aagtgttttt ttttgtcctg caggatatgg | 2460 |
| aagtgaatta tttccatgct tatatcgatg gagttgattt tgtgttcatt gacgctcctc | 2520 |
| tcttccgaca ccgccaggaa gacatttatg ggggcagcag acaggttaat cttctatatg | 2580 |
| ttggtgtttg attgcactga taaactgaga acaagccaag gcctactgac cggcatatga | 2640 |
| ttacacattt tatttttca ggaaattatg aagcgcatga ttttgttctg caaggccgct | 2700 |
| gtcgaggtat cctctccaac tcaattgaca acctattaca actatacaat tatgtgtatg | 2760 |
| catgtatttc aacagatacg taatctcttg tgaagtgcat atatactaac aacatttcaa | 2820 |
| taccttacat gcacatttgg tcaagcgtta tgatttaact tctaataatc tattgcactg | 2880 |
| atgaacaatt atcttgatga tccttggtac ttcatcgtta tgtttccatg ttctcttcac | 2940 |
| cgattgattt ggaaatagca tttccacctg ccacaaacaa taatatacac tcctactttc | 3000 |
| atccaatgta gatattttcg cacttggcat atcatcccat taaatattat tggtccatca | 3060 |
| tttttattcc tctataattt gcaggttcca tggcacgttc catgcggcgg tgtcccttat | 3120 |
| ggggatggaa atctggtgtt tattgcaaat gattggcaca cggcactcct gcctgtctat | 3180 |
| ctgaaagcat attacaggga ccatggtttg atgcagtaca ctcggtccat tatggtgata | 3240 |
| cataacatcg ctcaccaggt tccttttctc caaatcttga ttttctcta gtctctacta | 3300 |
| tttactccac attgtttgag gaaactaaac ggggttgcaaa attatgatgg cttatgaaag | 3360 |
| ttatagtctt atataggtaa atgcaccagt ggtgcttgca cttgtcacgc gtgttcactt | 3420 |
| tggtgcttac agttgtagac aataaaaaac tagtgcaaaa acttggctgt tgtgtgcaat | 3480 |
| acggtgcatt ttccgtatgt aggagtcaaa tattgcctgt gtggcattgt attcccgtct | 3540 |
| atagctgtta gaccatgcct acgtcgccat tgggcccaca caccctctat tacatgtggg | 3600 |
| ccccacttgt cagcctatga cataaataaa tggaaattta taatgaaaat gatggcctgg | 3660 |
| ggtcttgaaa atgggccgtc gcaggtatgc tggtagccag catgccctaa tcattaatcc | 3720 |
| ccctatgcac ttcatgtctt gtgtatgtgt gtgtgggaaa gggggggggt atgtatgctt | 3780 |
| atgcttatat cctttgctcc aaggctgcca tcctcaacaa gcccacctcc agcttcaaca | 3840 |
| cggccagcgc cttcatgatg gcccaggtgc tccgcaccat cgatcgaagc ggcaacgtcg | 3900 |
| tcgtcacgac catccaccaa cccaacgcac aaaatcctca ggctccgttc ggtacggagg | 3960 |
| aagagaaaat gcaggaaaaa acaacttcat gggaacaagg tttggtgaac agtaaaaaca | 4020 |
| tgtggaatct gaaaatgtag gtaccagaaa aaccggcctg ttcggtttgc aggaaaaagc | 4080 |
| atacttgcag cagcactgtt tggccctttc cagtgtaagg ctaaccatag tgggagtaac | 4140 |
| ataactaata ttatgtactt ggaactcaca aacatgctta tgtggcaggc aattaaagaa | 4200 |
| gagagagaga gtcatagtaa catagttaga taccgtatca taataaatat tatgttacta | 4260 |
| tgtgtcatgc atgacaataa atgagaccat ctgtgatact acgttatgat attatgcact | 4320 |
| atagatgtag tatcatacac tagtatcata tgcatgatac tagtgtatgt tactccccac | 4380 |
| tatgaccagc ctaacgaggg gatgggcatc agtagtgatt accagttttt attattttt | 4440 |
| attcggctgg acgccctact cttgtggtgc gtagcggaaa aaggcagtgc tagcttcggg | 4500 |
| actccgcgag cacatgaggt tctaccggat tttagatttc ctataaaaag tacaggctca | 4560 |
| cgcaactttt caatggaaca gaccatcaag attcctttga accgaacgca ctgcatgcaa | 4620 |
| gaattccaat gaaaacgag ccgtcaaatg ttcctgcgaa tttcctctat accgaacaga | 4680 |
| ccctcaacat cctcaaatag tgagcatgcc cctcttgtcc tttccccctc gtacccaaac | 4740 |
| gccatttggc gctcttggtg ttggatcatt tgcctcgggc atttgccaat tggcgccga | 4800 |

```
accatattaa agctatgact acttggtgtt ggatcaggga cgcaaagaat cccataaata      4860
ttgcaacgtt cattcaaatt cttaacattt gcgaggcgct tcatgatttc catctccgtc      4920
aggtctgaga catttggtcg tgtacactaa atttctcagg tcacttctcg tctaaatccg      4980
catatgtagc tcacttcaat gacttgcctt tggtctagct aacgccattt ggcgctcttg      5040 ggccccttg cttagcaaat ttttcatatg gctcgcactg cgcaagagga tttagatcac       5100
gggcagacgc gctagacgag gtcttccgca caatgaacat tgcgttcttt gctctgctct      5160
tcccggagac acttgtgatc ttattacgag ttgtgccatt tcaaacatct gtctctccat      5220
ggtcgctcca gccatagatg ccttgttctc tgaatggtgg gtttcagcta ggaacagggt      5280
gccaccttcg acaagaagtt gcatagtttg gtcgtcttga ctgcttggtc gatttggaag      5340
gaacgcaaca taagagtctt tgaaggcaaa gctaatttct ttgatcaagt tattagccag      5400
atcaaatgtg atgtattcta ctggtacaag gccggggcta tttgctttga gtcacttttt      5460
agctaaggcc gcttgggcta agcgcttggg gtcgttttg ctcaactgta gcctgaactt       5520
tctggacttt gtaattttt ttatcctcta taatgatcac atacagctct cctgcatggt       5580
tcgaaaagga aaaatgtgaa catgtgtggc aagtttaagc acaacccgtg catttacctc      5640
aaagttatac aacactgaca tgctgaatta cattttttt gaggatctga catgccgaat       5700
tacatgcttt ggacagttat tcatttcttc ggtacaccat tggctaatta tttctcttga      5760
cagttgctga attagtacat gctttggtcg cagttattcc tttgttcggt actctgttgg      5820
gctaattatt tctcttgatt gatgttgcat gcagggccgt ggcccagtag atgagttccc      5880
gttcaccgag ttgcctgagc actacctgga acacttcaga ctgtacgacc ccgtgggtgg      5940
tgaacacgcc aactacttcg ccgccggcct gaagatggcg gaccaggttg tcgtcgtgag      6000
cccggggtac ctgtgggagc tgaagacggt ggagggcggc tgggggcttc acgacatcat      6060
acggcagaac gactggaaga cccgcggcat cgtgaacggc atcgacaaca tggagtggaa      6120
ccccgaggtg gacgtccacc tcaagtcgga cggctacacc aacttctccc tggggacgct      6180
ggactccggc aagcggcagt gcaaggaggc cctgcagcgg gagctgggcc tgcaggtccg      6240
cggcgacgtg ccgctgctcg gcttcatcgg gcgcctggac gggcagaagg gcgtggagat      6300
catcgcggac gcgatgccct ggatcgtgag ccaggacgtg cagctggtca tgctgggcac      6360
cgggcgccac gacctggagg gcatgctgcg gcacttcgag cgggagcacc acgacaaggt      6420
gcgcgggtgg gtgggttct ccgtgcggct ggcgcaccgg atcacggccg gcgccgacgc      6480
gctcctcatg ccctcccggt tcgagccgtg cggactgaac cagctctacg ccatggccta      6540
cggcaccgtc ccgtcgtgc atgccgtcgg cggcctgagg gacaccgtgc cgccgttcga      6600 cccttcaac cactccgggc tcgggtggac gttcgaccgc gcagaggcgc agaagctgat       6660
cgaggcgctc gggcactgcc tccgcaccta ccgggactac aaggagagct ggaggggct       6720 ccaggagcgc ggcatgtcgc aggacttcag ctggagcat gccgccaagc tctacgagga       6780
cgtcctcgtc aaggccaagt accagtggtg a                                     6811
```

<210> SEQ ID NO 4
<211> LENGTH: 798
<212> TYPE: PRT
<213> ORGANISM: Triticum aestivum

<400> SEQUENCE: 4

Met Ser Ser Ala Val Ala Ser Ala Ala Ser Phe Leu Ala Leu Ala Ser
1               5                   10                  15

```
Ala Ser Pro Gly Arg Ser Arg Arg Thr Arg Val Ser Ala Ser Pro
         20                  25                  30

Pro His Thr Gly Ala Gly Arg Leu His Trp Pro Pro Ser Pro Pro Gln
             35                  40                  45

Arg Thr Ala Arg Asp Gly Ala Val Ala Ala Arg Ala Ala Gly Lys Lys
 50                  55                  60

Asp Ala Gly Ile Asp Asp Ala Pro Ala Arg Gln Pro Arg Ala Leu
 65                  70                  75                  80

Arg Gly Gly Ala Ala Thr Lys Val Ala Glu Arg Arg Asp Pro Val Lys
                 85                  90                  95

Thr Leu Asp Arg Asp Ala Ala Glu Gly Ala Pro Ser Pro Pro Ala
        100                 105                 110

Pro Arg Gln Glu Asp Ala Arg Leu Pro Ser Met Asn Gly Met Pro Val
            115                 120                 125

Asn Gly Glu Asn Lys Ser Thr Gly Gly Gly Ala Thr Lys Asp Ser
    130                 135                 140

Gly Leu Pro Ala Pro Ala Arg Ala Pro Gln Pro Ser Ser Gln Asn Arg
145                 150                 155                 160

Val Pro Val Asn Gly Glu Asn Lys Ala Asn Val Ala Ser Pro Thr
                165                 170                 175

Ser Ile Ala Glu Val Ala Ala Pro Asp Pro Ala Ala Thr Ile Ser Ile
                180                 185                 190

Ser Asp Lys Ala Pro Glu Ser Val Pro Ala Glu Lys Ala Pro Pro
        195                 200                 205

Ser Ser Gly Ser Asn Phe Val Pro Ser Ala Ser Ala Pro Gly Ser Asp
        210                 215                 220

Thr Val Ser Asp Val Glu Leu Glu Leu Lys Lys Gly Ala Val Ile Val
225                 230                 235                 240

Lys Glu Ala Pro Asn Pro Lys Ala Leu Ser Pro Pro Ala Ala Pro Ala
                245                 250                 255

Val Gln Gln Asp Leu Trp Asp Phe Lys Lys Tyr Ile Gly Phe Glu Glu
            260                 265                 270

Pro Val Glu Ala Lys Asp Asp Gly Arg Ala Val Ala Asp Ala Gly
        275                 280                 285

Ser Phe Glu His His Gln Asn His Asp Ser Gly Pro Leu Ala Gly Glu
        290                 295                 300

Asn Val Met Asn Val Val Val Ala Ala Glu Cys Ser Pro Trp Cys
305                 310                 315                 320

Lys Thr Gly Gly Leu Gly Asp Val Ala Gly Ala Leu Pro Lys Ala Leu
                325                 330                 335

Ala Lys Arg Gly His Arg Val Met Val Val Pro Arg Tyr Gly Asp
            340                 345                 350

Tyr Glu Glu Ala Tyr Asp Val Gly Val Arg Lys Tyr Lys Ala Ala
        355                 360                 365

Gly Gln Asp Met Glu Val Asn Tyr Phe His Ala Tyr Ile Asp Gly Val
        370                 375                 380

Asp Phe Val Phe Ile Asp Ala Pro Leu Phe Arg His Arg Gln Glu Asp
385                 390                 395                 400

Ile Tyr Gly Gly Ser Arg Gln Glu Ile Met Lys Arg Met Ile Leu Phe
        405                 410                 415

Cys Lys Ala Ala Val Glu Val Pro Trp His Val Pro Cys Gly Gly Val
            420                 425                 430

Pro Tyr Gly Asp Gly Asn Leu Val Phe Ile Ala Asn Asp Trp His Thr
        435                 440                 445
```

Ala Leu Leu Pro Val Tyr Leu Lys Ala Tyr Tyr Arg Asp His Gly Leu
    450                 455                 460

Met Gln Tyr Thr Arg Ser Ile Met Val Ile His Asn Ile Ala His Gln
465                 470                 475                 480

Gly Arg Gly Pro Val Asp Glu Phe Pro Phe Thr Glu Leu Pro Glu His
                485                 490                 495

Tyr Leu Glu His Phe Arg Leu Tyr Asp Pro Val Gly Gly Glu His Ala
            500                 505                 510

Asn Tyr Phe Ala Ala Gly Leu Lys Met Ala Asp Gln Val Val Val
        515                 520                 525

Ser Pro Gly Tyr Leu Trp Glu Leu Lys Thr Val Glu Gly Gly Trp Gly
    530                 535                 540

Leu His Asp Ile Ile Arg Gln Asn Asp Trp Lys Thr Arg Gly Ile Val
545                 550                 555                 560

Asn Gly Ile Asp Asn Met Glu Trp Asn Pro Glu Val Asp Val His Leu
                565                 570                 575

Lys Ser Asp Gly Tyr Thr Asn Phe Ser Leu Gly Thr Leu Asp Ser Gly
            580                 585                 590

Lys Arg Gln Cys Lys Glu Ala Leu Gln Arg Glu Leu Gly Leu Gln Val
        595                 600                 605

Arg Gly Asp Val Pro Leu Leu Gly Phe Ile Gly Arg Leu Asp Gly Gln
    610                 615                 620

Lys Gly Val Glu Ile Ile Ala Asp Ala Met Pro Trp Ile Val Ser Gln
625                 630                 635                 640

Asp Val Gln Leu Val Met Leu Gly Thr Gly Arg His Asp Leu Glu Gly
                645                 650                 655

Met Leu Arg His Phe Glu Arg Glu His His Asp Lys Val Arg Gly Trp
            660                 665                 670

Val Gly Phe Ser Val Arg Leu Ala His Arg Ile Thr Ala Gly Ala Asp
        675                 680                 685

Ala Leu Leu Met Pro Ser Arg Phe Glu Pro Cys Gly Leu Asn Gln Leu
    690                 695                 700

Tyr Ala Met Ala Tyr Gly Thr Val Pro Val Val His Ala Val Gly Gly
705                 710                 715                 720

Leu Arg Asp Thr Val Pro Pro Phe Asp Pro Phe Asn His Ser Gly Leu
                725                 730                 735

Gly Trp Thr Phe Asp Arg Ala Glu Ala Gln Lys Leu Ile Glu Ala Leu
            740                 745                 750

Gly His Cys Leu Arg Thr Tyr Arg Asp Tyr Lys Glu Ser Trp Arg Gly
        755                 760                 765

Leu Gln Glu Arg Gly Met Ser Gln Asp Phe Ser Trp Glu His Ala Ala
    770                 775                 780

Lys Leu Tyr Glu Asp Val Leu Val Lys Ala Lys Tyr Gln Trp
785                 790                 795

<210> SEQ ID NO 5
<211> LENGTH: 7010
<212> TYPE: DNA
<213> ORGANISM: Triticum aestivum

<400> SEQUENCE: 5
gggggccgtt cgtacgtacc cgcccctcgt gtaaagccgc cgccgtcgtc gccgtccccc      60
gctcgcggcc atttcttcgg cctgaccccg ttcgtttacc cccacacaga gcacactcca     120
gtccagtcca gcccactgcc accgcgctac tctccactcc cactgccacc acctccgcct     180

```
gcgccgcgct ctgggcggac caacccgcga accgtaccat ctcccgcccc gatccatgtc    240
gtcggcggtc gcgtccgccg catccttcct cgcgctcgcg tcagcctccc ccgggagatc    300
acgcaggcgg gcgagggtga gcgcgcagcc accccacgcc ggggccggca ggttgcactg    360
gccgccgtgg ccgccgcagc gcacggctcg cgacggagct gtggcggcgc tcgccgccgg    420
gaagaaggac gcggggatcg acgacgccgc cgcgtccgtg aggcagcccc gcgcactccg    480
cggtggcgcc gccaccaagg tagttagtta tgaccaagtt atgacgcgtg cgcgcgcctc    540
gagatcatcg tcgtctcgct cacgaattgt ttatttatac aaaacgcacg cccgcgtgtg    600
caggtcgcgg agcgaaggga tcccgtcaag acgctcgacc gcgacgccgc ggaaggcggc    660
gggccgtccc cgccggcagc gaggcaggac gccgcccgtc cgccgagtat gaacggcatg    720
ccggtgaacg gcgagaacaa atctaccggc ggcggcggcg cgactaaaga cagcgggctg    780
cccacgcccg cacgcgcgcc ccatccgtcg acccagaaca gagcaccggt gaacggtgaa    840
aacaaagcta acgtcgcctc gccgccgacg agcatagccg aggccgcggc ttcggattcc    900
gcagctacca tttccatcag cgacaaggcg ccggagtccg ttgtcccagc tgagaagacg    960
ccgccgtcgt ccggctcaaa tttcgagtcc tcggcctctg ctcccgggtc tgacactgtc   1020
agcgacgtgg aacaagaact gaagaagggt gcggtcgttg tcgaagaagc tccaaagcca   1080
aaggctcttt cgccgcctgc agccccogct gtacaagaag acctttggga tttcaagaaa   1140
tacattggtt tcgaggagcc cgtggaggcc aaggatgatg ccgggctgt cgcagatgat    1200 gcgggctcct ttgaacacca ccagaatcac gactccggac cttggcagg ggagaatgtc    1260 atgaacgtgg tcgtcgtggc tgctgagtgt tctccctggt gcaaaacagg catggacatt   1320
acctcttcag tctctcttcc tgttgttcat aaaactttgc tcgaattact cataagaaca   1380
aacattgtgt tgcataggtg gtctgggaga tgttgcgggt gctctgccca aggctttggc   1440
aaagagagga catcgtgtta tggtactaca agctttcatt taactctgtt gggtccatat   1500
gttcgaataa tatcagtgag tagtataatg ttattaagtg caagacatga aagtgttctt   1560
ttgtcatact ccctccgtaa attaatataa gagcgtttag attactactt tagtgatcta   1620
aacgctctta tagtagttta cagacggagt agagtatttc atagccaacc ctggaggtta   1680
ggttgctgag gcctactggg tgggggaggg ggtttgaaac aagtggtggt tagcagccag   1740
atttcacaaa gaaggaggct gataaccaca ccatcagtga aggaatgaat gtcgggtacc   1800
cgatcgaccg ttttgcccaa cgtcgggttt accogccota tagatccgaa taagtagttc   1860
ctatcttcaa ttaggtacca aatatcgcca gcgcccgtgt gtgtatttat actactggat   1920
gatcaattta tcaacatttc cggttaatgg tttctatcat attcactgta attgttagta   1980
aacagtagat gtttgtaatg tagatgatgg ataaatgtat gttgtcgagc tttcatttca   2040
atgcaatttt gattgggagc tagtttcgcg gttcggttag agccatcaaa accccagaat   2100
ttttgggagt tggcttgtga gagagggttt tggggagtta actttcggga ttcagttaga   2160
gacgctctta ctagttccag taaagagtaa actatttct gcaggcatcc caattattct    2220
gtagaaatta gaagtggaaa atagttatgg tatcatataa accatatatt attcaaaatc   2280
tagaatcatg gacttggcta gactttgata atctgaaatt ttaaatttga tgataattga   2340
gaaatgatcc tttctatctt aggttgtggt accaaggtat ggggactatg aagaagccta   2400
cgatgtcgga gtccgaaaat actacaaggc tgctggacag gtaagcaaaa atgcaatcga   2460
aggggagctg aaatttatt gcttattgtc ataataaatc aatttttaag tgttttttt    2520 gtcctgcagg atatggaagt gaattatttc catgcttata tcgatggagt tgattttgtg   2580
```

```
ttcattgacg ctcctctctt ccgacaccgt caggaagaca tttatggggg cagcagacag    2640
gttaatcttc tatatgttgg tgtttgattg cactgataaa ctgagaacaa gccaaggcct    2700
actgactggc atatgattac acattttatt ttttcaggaa attatgaagc gcatgatttt    2760
gttctgcaag gccgctgttg aggtatctct ccaactcaat tgacaaccta ttaccactat    2820
acaattatgt gtatgcatgt atttcaacag atacataatc tcttgtgaag tgcatatata    2880
ctaataacat ttcaataccct tacatgcaca tttggtcaag cgttatgatt taacttctga    2940
taatctattg cactgatgaa caattatctt gatgatcctt gttacttcat cgttatgttt    3000
ccatgttctc ttcaccgcga attgatttgg aaatagcatt tccacctgcc acaaacaata    3060
atatacactc ctactttcat ccaatttaga tattttcgta cttggcatat catcccatta    3120
aatattattg gtccatcatt tttattcctc tataatttgc aggttccatg gcacgttcca    3180
tgcggcggtg tcccttatgg ggatggaaat ctggtgttta ttgcaaatga ttggcacacg    3240
gcactcctgc ctgtctatct gaaagcatat tacagggacc atggtttgat gcagtacact    3300
cggtccatta tggtgataca taacatcgct caccaggttc ctttttctcct aatcttgatt    3360 tttctctagt ctctactatt tactccacat tgtttgagga aactaaacgg gttgcaaaat    3420
tatgatggct tatgaaagtt atagtcttat agaggtaaat gcaccagtgg tgcttgaact    3480
tgtcacgcgt gttcactttg gtgcttacag ttgtagacta tgaaaaacgg gtgcaaaaac    3540
ttgctgttgt gtgccatacg gtgcattttc cgtatgtagg agtcaaacgt tgcctatgtg    3600
ggcattgtat tcccgtctat agctgttaga ccgtgcctac gtcgccattg gcccacaca    3660 ctctctattt acatgtgggc cccacttgtc aacctatgac ataaataaat ggaaatttat    3720
aataaaaatg atggcctggg gtcttgaaaa tgggacctcg caggtatgct ggtagccagc    3780
acgccctaaa cattaatccc ctatgcactt catgtcttgt gtatgtgtgt gtctgtgtgg    3840
ggaggggggg ggtatgtatg cttatatcct ttgctccaag gctaccatcc tcaacaagcc    3900
cacctccgct tcaacacggc cagcgccttc atgatggccc aggtgctccg caccatcgct    3960
caaagcggca acgtcgttgt catgaccatc caccaaccca acacacaaaa tcctcaacat    4020
ccgcaaatag tgagcatgcc cctcttgtcc tttccccctcg tacccaaaca tgtcttgata    4080
acccttggag ctgcacaagt tgtgaccatc gcctgcgtcg cctcatagag cccgacctag    4140
ccggaccgtt atagaagcct acttgggagc ccatacctcc ctgcacatcc tcctctttcc    4200
ccatagatcg tgccgccatc gcaaaccaac ttctcctctc cttctcccac tctggccgtt    4260
tcccccgccg cgaagctgca atacatgccg agttggccat ggcccatttc cccaattgct    4320
cgcactagga ggtcctcctc taagcctagc acctttttccc ctcaccaatt gcaagttggg    4380
gagcccctcg cgagctccct acgtcggctg cagttgcctg ccgcctcaac tctgatccag    4440
acctcgttcc cgtggcctcg cgacatctc ctcgacctcc cattccacac gtggcctggc    4500
gaggatcacc gcatgttcat ccatgtgaac cgaatcatca tagaactaac accggagagg    4560
tcatcccgac ggcgtcgcac tgttcctcta ttcccccccaa gccgtgtcgc gtcataatat    4620
aagacggact tatttgtatc ccttgggtca tcggttcaat ggctatttct ttctcctgtc    4680
tactgataag tgggacccac acgccacact aagcccttte tttctcctac ccgttgataa    4740
gtgggaccca cacacagtac ttagccgagag agaacatg agcttgttgg tgccacgtcg    4800
gcaagccatg tcagcagtct taacggctac aaacaacgga tatggtgtca cgtgagcgtt    4860
tacgaatgga aagtgcatca tactgcatgc gagagccaga gccaggtttt tgcaccagtt    4920
ttctgtattt tacaactgcg agcatcaaag tgtacatatg ccgaaccaaa gtgaacatgg    4980
```

```
tgagtccatt cttttctggt gcggtgggtg gctcaaagac accccaatag aagctattgc   5040
ctccgacatt gccaattcgg tgccgaacca tattgaagtg gtgaggtcag ttgcttgtgc   5100
tatgactact aggtattgga tgagggacat aaaggatctc ataaatattg caatgttcat   5160
tcaaattctt aacatttgcg aagcgcttca tgatttccat ctcccctaga tcagagacac   5220
ttggtcgtgt acactgaatt tctcaggtcg cttctcgtct aaatccgcat atgtagctca   5280
cttcaatgac ttgcctttgg tccagctaac gccatttgcg tagcaaattt ttcatatggc   5340
tcgctctgcg caagaggatt tggatcacgg gcagacgcgc tagacaaggt cttccgcaca   5400
atgaacattg agttttttga tccgctcttc ccgaagacac ttgtgatctt attacgagtt   5460
gtgccatttc aaacatctgt ctctccatgg tcgccccagc catagatgcc ttgttctctg   5520
aatggtgggt ttcagctagg aacagggtgc caccttcgga caagaagttg cgtagtttgg   5580
tcgtcttaac tgcttggttg atttggaagg aacacaacaa cagtctttga aggcaaagct   5640
aattccttcg atcaagttat tagacggatc aagtgtgatg aatcctactg gtacaatgcc   5700
gttgctagtt gcttggagtc actatttggc taggtcgctt gccatcccgc tctgtgctaa   5760
gcgcttgggg tcgcttttgc tcaatttgta ttttgttgtt atgtgttttt agtaatgtaa   5820
cctgaacttt ctggactaag tagaaaaaaa ttctcctcca taatgatcac atacagttct   5880
cctgcatggt tcgaaaaaaa aatgagaaca tccgtggcaa gtttaagcac caccggtgca   5940
tttttacctc aaagttatat acaacactga catgccgaat tacatgcttt ggtcagttat   6000
tccattcttc ggtactccgt tgggctaatt cttctcttc atgttgcatg cagggccgtg   6060
gccctgtaga tgaattcccg ttcaccgagt tgcctgagca ctacctggaa cacttcagac   6120
tgtacgaccc cgtgggtggt gaacacgcca actacttcgc cgccggcctg aagatggcgg   6180
accaggttgt cgtggtgagc cccgggtacc tgtgggagct gaagacggtg gagggcggct   6240
gggggcttca cgacatcata cggcagaacg actggaagac ccgcggcatc gtcaacggca   6300
tcgacaacat ggagtggaac cccgaggtgg acgcccacct caagtcggac ggctacacca   6360
acttctccct gaggacgctg gactccggca agcggcagtg caaggaggcc ctgcagcgcg   6420
agctgggcct gcaggtccgc gccgacgtgc cgctgctcgg cttcatcggc cgcctggacg   6480
ggcagaaggg cgtggagatc atcgcggacg ccatgcccctg gatcgtgagc caggacgtgc   6540
agctggtgat gctgggcacc gggcgccacg acctggagag catgctgcag cacttcgagc   6600
gggagcacca cgacaaggtg cgcggtgggt ggggttctc cgtgcgcctg gcgcaccgga   6660
tcacggcggg ggcggacgcg ctcctcatgc cctcccggtt cgagccgtgc gggctgaacc   6720
agctctacgc catggcctac ggcaccgtcc ccgtcgtgca cgccgtcggc ggcctcaggg   6780
acaccgtgcc gccgttcgac cccttcaacc actccgggct cgggtggacg ttcgaccgcg   6840
ccgaggcgca caagctgatc gaggcgctcg ggcactgcct ccgcacctac cgagacttca   6900
aggagagctg gagggccctc caggagcgcg gcatgtcgca ggacttcagc tgggagcacg   6960
ccgccaagct ctacgaggac gtcctcgtca aggccaagta ccagtggtga            7010
```

<210> SEQ ID NO 6
<211> LENGTH: 799
<212> TYPE: PRT
<213> ORGANISM: Triticum aestivum

<400> SEQUENCE: 6

```
Met Ser Ser Ala Val Ala Ser Ala Ala Ser Phe Leu Ala Leu Ala Ser
1               5                   10                  15
```

-continued

```
Ala Ser Pro Gly Arg Ser Arg Arg Ala Arg Val Ser Ala Gln Pro
         20                  25                  30

Pro His Ala Gly Ala Gly Arg Leu His Trp Pro Trp Pro Pro Gln
         35                  40                  45

Arg Thr Ala Arg Asp Gly Ala Val Ala Ala Leu Ala Ala Gly Lys Lys
    50                  55                  60

Asp Ala Gly Ile Asp Ala Ala Ser Val Arg Gln Pro Arg Ala
65                  70                  75                  80

Leu Arg Gly Gly Ala Ala Thr Lys Val Ala Glu Arg Arg Asp Pro Val
                 85                  90                  95

Lys Thr Leu Asp Arg Asp Ala Ala Glu Gly Gly Pro Ser Pro Pro
         100                 105                 110

Ala Ala Arg Gln Asp Ala Ala Arg Pro Pro Ser Met Asn Gly Met Pro
         115                 120                 125

Val Asn Gly Glu Asn Lys Ser Thr Gly Gly Gly Ala Thr Lys Asp
    130                 135                 140

Ser Gly Leu Pro Thr Pro Ala Arg Ala Pro His Pro Ser Thr Gln Asn
145                 150                 155                 160

Arg Ala Pro Val Asn Gly Glu Asn Lys Ala Asn Val Ala Ser Pro Pro
                 165                 170                 175

Thr Ser Ile Ala Glu Ala Ala Ala Ser Asp Ser Ala Ala Thr Ile Ser
         180                 185                 190

Ile Ser Asp Lys Ala Pro Glu Ser Val Val Pro Ala Glu Lys Thr Pro
    195                 200                 205

Pro Ser Ser Gly Ser Asn Phe Glu Ser Ser Ala Ser Ala Pro Gly Ser
210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
                 245                 250                 255

Ala Val Gln Glu Asp Leu Trp Asp Phe Lys Lys Tyr Ile Gly Phe Glu
         260                 265                 270

Glu Pro Val Glu Ala Lys Asp Asp Gly Arg Ala Val Ala Asp Asp Ala
    275                 280                 285

Gly Ser Phe Glu His His Gln Asn His Asp Ser Gly Pro Leu Ala Gly
290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
                 325                 330                 335

Leu Ala Lys Arg Gly His Arg Val Met Val Val Val Pro Arg Tyr Gly
         340                 345                 350

Asp Tyr Glu Glu Ala Tyr Asp Val Gly Val Arg Lys Tyr Tyr Lys Ala
    355                 360                 365

Ala Gly Gln Asp Met Glu Val Asn Tyr Phe His Ala Tyr Ile Asp Gly
370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
                 405                 410                 415

Phe Cys Lys Ala Ala Val Glu Val Pro Trp His Val Pro Cys Gly Gly
         420                 425                 430

Val Pro Tyr Gly Asp Gly Asn Leu Val Phe Ile Ala Asn Asp Trp His
    435                 440                 445
```

Thr Ala Leu Leu Pro Val Tyr Leu Lys Ala Tyr Tyr Arg Asp His Gly
    450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
    530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
            580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
    610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
    690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
        755                 760                 765

Ala Leu Gln Glu Arg Gly Met Ser Gln Asp Phe Ser Trp Glu His Ala
    770                 775                 780

Ala Lys Leu Tyr Glu Asp Val Leu Val Lys Ala Lys Tyr Gln Trp
785                 790                 795

<210> SEQ ID NO 7
<211> LENGTH: 2805
<212> TYPE: DNA
<213> ORGANISM: Tviticum aestivum L.

<400> SEQUENCE: 7
cctgcgcgcg ccatggcggc tctggtcacg tcccagctcg ccacctccgg caccgtcctc    60
agcgtcaccg acagattccg gcgtccaggt tttcagggcc tgaggccccg gaacccggcg   120
gatgcggcgc tcggcatgag gactgtcgga gcgagcgccg ccccaaagca aagcaggaaa   180

```
ccgcaccgat tcgaccggcg gtgcctctcc atggtggtgc gcgccacggg cagcggcggc    240
atgaacctcg tgttcgtcgg cgccgagatg gcgccctgga gcaagactgg cggcctcggc    300
gacgtcctcg ggggcctccc cgccgccatg gccgtaagct tgcgccactg ccttcttata    360
aatgtttctt cctgcagcca tgcctgccgt tacaacgggt gccgtgtccg tgcaggccaa    420
cggtcaccgg gtcatggtca tctccccgcg ctacgaccag tacaaggacg cctgggacac    480
cagcgtcatc tccgaggtat atatccgcca catgaattat cacaattcac atgctcctgc    540
acatttctgc aagactttac tgactggctg gatctcgcag atcaaggtcg ttgacaggta    600
cgagagggtg aggtacttcc actgctacaa gcgcggggtg gaccgcgtgt tcgtcgacca    660
cccgtgcttc ctggagaagg tgaccgatcg ctcgccgtcg atcgatcaag ctagctcctc    720
gtcgtctcaa cccgcatggt gtttgataat ttcagtgagt ctttgcgtct gctggttaca    780
atttccaggt ccggggcaag accaaggaga agatctatgg acccgacgcc ggcaccgact    840
acgaggacaa ccagcagcgc ttcagccttc tctgccaggc agcacttgag gtgcccagga    900
tcctcgacct caacaacaac ccacactttt ctggacccta cggtaagatc aagaacaact    960
agagtgtatc tgaagaactt gatttctact tgagagcact ggatgattat catcttcctt   1020
gtatcttggt gctgccatgc tatgccgtgc cgtgccgcgc cgcgcagggg aagacgtggt   1080
gtttgtgtgc aacgactggc acacgggcct tctggcctgc tacctcaaga gcaactacca   1140
gtccaatggc atctatagga cggccaaggt tttgcatctt ctgaaacttt atattcgctc   1200
tgcatatcaa ttttgcggtt cattctggca gcctgaattt tacattgcaa ctccatttca   1260
tggctaggtg gcattctgca tccacaacat ctcgtaccag ggccgcttct ccttcgacga   1320
cttcgcgcag ctcaacctgc ctgacaggtt caagtcgtcc ttcgacttca tcgacggcta   1380
cgacaagccg gtggaggggc gcaagatcaa ctggatgaag gccgggatcc tgcaggccga   1440
caaggtgctg actgtgagcc cctactatgc tgaggagcta atctctggcg aagccagggg   1500
ctgcgagctc gacaacatca tgcgcctcac tgggatcacc ggcatcgtca acggcatgga   1560
cgtcagcgag tgggacccca tcaaggacaa gttcctcacc gtcaactacg acgtcaccac   1620
cgtgagcacc cacccaccca cacaaagatt tcttccggtg atcgctggtt ctgggtggat   1680
tctgagttct gacaaacgag gcaaagtgac aggcgttgga ggggaaggcg ctgaacaagg   1740
aggcgctgca ggccgaggtg gggctgccgg tggaccggaa ggtgcccctg gtggcgttca   1800
tcggcaggct ggaggagcag aagggccccg acgtgatgat cgccgccatc ccggagatcg   1860
tgaaggagga ggacgtccag atcgttctcc tggtacgatc gaccgacatt gctgacccgt   1920
tcaggaaaat ctcctgatag ctcgccgtgg ggatgggtgg gtgactgact gatcgaatgc   1980
attgcagggc accgggaaga agaagtttga gcggctgctc aagagcgtgg aggagaagtt   2040
cccgaccaag gtgtgggccg tggtcaggtt caacgcgccg ctggctcacc agatgatggc   2100
cggcgccgac gtgctggcgg tcaccagccg cttcgagccc tgcggcctca tccagctcca   2160
gggaatgcgc tacggaacgg taaacgcatc ctccttcagt ccttcttgcc agttcctcac   2220
ctcctttgca tatccatggc catgaccgaa gtttctttca aattttcagc cgtgcgcctg   2280
cgcgtcgaca gcggggctcg tcgacactat cgtggaaggc aagaccgggt tccacatggg   2340
ccgcctcagc gttgacgtat gctcatcgat cctcttgtat acattcattc atcttgttca   2400
tcatggcagc tcagacagat catgaagtgg tgcactttc ttgttggtgg ccagtgcaac   2460
gtggtggagc cggccgacgt gaagaaggtg gtcaccaccc tgaagcgcgc cgtcaaggtc   2520
gtcggcacgc cggcgtacca tgagatggtc aagaactgca tgatacagga tctctcctgg   2580
```

```
aaggtaagtc gtctctggtt cagtatgcac ttcctggaac aactaagagt gaagggccga    2640
tgtatccatt aatggtggct tgcgcatatg atgcagggc ctgccaagaa ctgggaggac    2700
gtgcttctgg aactgggggt ggaggggagc gagccgggca tcgtcggcga ggagatcgcg    2760
ccgctcgccc tggagaacgt cgccgctccc tgaagagaga agaa                    2805
```

<210> SEQ ID NO 8
<211> LENGTH: 604
<212> TYPE: PRT
<213> ORGANISM: Tviticum aestivum L.

<400> SEQUENCE: 8

```
Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val Arg Ala Thr Gly Ser Gly Met Asn Leu Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Ala Ala Met Ala Ala Asn Gly His Arg
            100                 105                 110

Val Met Val Ile Ser Pro Arg Tyr Asp Gln Tyr Lys Asp Ala Trp Asp
        115                 120                 125

Thr Ser Val Ile Ser Glu Ile Lys Val Val Asp Arg Tyr Glu Arg Val
    130                 135                 140

Arg Tyr Phe His Cys Tyr Lys Arg Gly Val Asp Arg Val Phe Val Asp
145                 150                 155                 160

His Pro Cys Phe Leu Glu Lys Val Arg Gly Lys Thr Lys Glu Lys Ile
                165                 170                 175

Tyr Gly Pro Asp Ala Gly Thr Asp Tyr Glu Asp Asn Gln Gln Arg Phe
            180                 185                 190

Ser Leu Leu Cys Gln Ala Ala Leu Glu Val Pro Arg Ile Leu Asp Leu
        195                 200                 205

Asn Asn Asn Pro His Phe Ser Gly Pro Tyr Gly Glu Asp Val Val Phe
    210                 215                 220

Val Cys Asn Asp Trp His Thr Gly Leu Leu Ala Cys Tyr Leu Lys Ser
225                 230                 235                 240

Asn Tyr Gln Ser Asn Gly Ile Tyr Arg Thr Ala Lys Val Ala Phe Cys
                245                 250                 255

Ile His Asn Ile Ser Tyr Gln Gly Arg Phe Ser Phe Asp Phe Ala
            260                 265                 270

Gln Leu Asn Leu Pro Asp Arg Phe Lys Ser Ser Phe Asp Phe Ile Asp
        275                 280                 285

Gly Tyr Asp Lys Pro Val Glu Gly Arg Lys Ile Asn Trp Met Lys Ala
    290                 295                 300

Gly Ile Leu Gln Ala Asp Lys Val Leu Thr Val Ser Pro Tyr Tyr Ala
305                 310                 315                 320

Glu Glu Leu Ile Ser Gly Glu Ala Arg Gly Cys Glu Leu Asp Asn Ile
                325                 330                 335
```

```
Met Arg Leu Thr Gly Ile Thr Gly Ile Val Asn Gly Met Asp Val Ser
            340                 345                 350
Glu Trp Asp Pro Ile Lys Asp Lys Phe Leu Thr Val Asn Tyr Asp Val
        355                 360                 365
Thr Thr Ala Leu Glu Gly Lys Ala Leu Asn Lys Glu Ala Leu Gln Ala
370                 375                 380
Glu Val Gly Leu Pro Val Asp Arg Lys Val Pro Leu Val Ala Phe Ile
385                 390                 395                 400
Gly Arg Leu Glu Glu Gln Lys Gly Pro Asp Val Met Ile Ala Ala Ile
                405                 410                 415
Pro Glu Ile Val Lys Glu Asp Val Gln Ile Val Leu Leu Gly Thr
            420                 425                 430
Gly Lys Lys Lys Phe Glu Arg Leu Leu Lys Ser Val Glu Glu Lys Phe
        435                 440                 445
Pro Thr Lys Val Trp Ala Val Arg Phe Asn Ala Pro Leu Ala His
    450                 455                 460
Gln Met Met Ala Gly Ala Asp Val Leu Ala Val Thr Ser Arg Phe Glu
465                 470                 475                 480
Pro Cys Gly Leu Ile Gln Leu Gln Gly Met Arg Tyr Gly Thr Pro Cys
                485                 490                 495
Ala Cys Ala Ser Thr Gly Gly Leu Val Asp Thr Ile Val Glu Gly Lys
            500                 505                 510
Thr Gly Phe His Met Gly Arg Leu Ser Val Asp Cys Asn Val Val Glu
        515                 520                 525
Pro Ala Asp Val Lys Lys Val Val Thr Thr Leu Lys Arg Ala Val Lys
    530                 535                 540
Val Val Gly Thr Pro Ala Tyr His Glu Met Val Lys Asn Cys Met Ile
545                 550                 555                 560
Gln Asp Leu Ser Trp Lys Gly Pro Ala Lys Asn Trp Glu Asp Val Leu
                565                 570                 575
Leu Glu Leu Gly Val Glu Gly Ser Glu Pro Gly Ile Val Gly Glu Glu
            580                 585                 590
Ile Ala Pro Leu Ala Leu Glu Asn Val Ala Ala Pro
        595                 600

<210> SEQ ID NO 9
<211> LENGTH: 2818
<212> TYPE: DNA
<213> ORGANISM: Tviticum aestivum L.

<400> SEQUENCE: 9
cctgcgcgcg cgatggcggc tctggtcacg tcgcagctcg ccacctccgg caccgtcctc    60
ggcatcaccg acaggttccg gcgtgcaggt tttcagggtg tgaggccccg gagcccggca   120
gatgcgccgc tcggcatgag gactaccgga gcgagcgccg ccccgaagca acaaagccgg   180
aaagcgcacc gcgggacccg gcggtgcctc tccatggtgg tgcgcgccac gggcagcgcc   240
ggcatgaacc tcgtgttcgt cggcgccgag atggcgccct ggagcaagac cggcggcctc   300
ggcgacgtcc tcgggggcct cccccagcc atggccgtaa gctagctagc tagcaccact   360
gtcttctgat aatgtttctt cttgcagcca gccatgcctg ccattacaag tttacaactg   420
atgctgtgtc tgcaggccaa cggtcaccgg gtcatgtca tctccccgcg ctacgaccag   480
tacaaggacg cctgggacac cagcgtcgtc tccgaggtac acatatatcc gccacatgaa   540
ttatcacagt tcacatgctc ctgcacattt ctgcaaggtt ccactcaccg actggatttc   600
acagatcaag gtcgcggacg agtacgagag ggtgaggtac ttccactgct acaagcgcgg   660
```

```
ggtggaccgc gtgttcgtcg accacccgtg cttcctggag aaggtgacca atcgtcgtcg    720
tcgatcgatc aatcgatcaa gctatctttt cgtcgtctca acattcatgg tgattgattt    780
gggtgagtct ttgtttctgc tggttgcaat ttccaggtcc ggggcaagac caaggagaag    840
atctacgggc ccgatgccgg cacggactac gaggacaacc agctacgctt cagcctgctc    900
tgccaggcag cgcttgaggc acccaggatc ctcgacctca acaacaaccc atacttctcc    960
ggaccctacg gtaagatcaa caacacccag cagctactag agtgtctgaa gaacttgatt   1020
tcttcttgag agcactggat gattatcatc ttccctgtgt cttggtgctg ccacgccatg   1080
ctatgccgcg ccacgccgcg caggggaaga cgtggtgttc gtgtgcaacg actggcacac   1140
gggccttctg gcctgctacc tcaagagcaa ctaccagtcc agtggcatct ataggacggc   1200
caaggttttg catcttctca aactttatat tctctctgca gaattttaca ttgcaacttc   1260
atttcatgtc caggtagcgt tctgcatcca caacatctcg tatcagggcc gcttctcctt   1320
cgacgacttc gcgcagctca acctgcccga caggttcaag tcgtccttcg acttcatcga   1380
cggctacgac aagccggtgg aggggcgcaa gatcaactgg atgaaggccg ggatcctgca   1440
ggccgacaag gtgctcacgg tgagccccta ctacgcggag gagctcatct ccggcgaagc   1500
caggggctgc gagctcgaca acatcatgcg cctcacgggc atcaccggca tcgtcaacgg   1560
catggacgtc agcgagtggg accccgccaa ggacaagttc ctcgccgcca actacgacgt   1620
caccaccgtg agcacccgcc cacccacaca cccacacaaa gatttcttcc ggtgattgct   1680
ggttctgggt gggttctgac ggacgaggca aagtgacagg cgttggaggg gaaggcgctg   1740
aacaaggagg cgctgcaggc cgaggtgggg ctgccggtgg accggaaggt gccccctggtg  1800 gccttcatcg gcaggctgga ggagcagaag ggccccgacg tgatgatcgc cgccatcccg   1860
gagatcttga aggaggagga cgtccagatc gttctcctgg tacgtcatcg accccaaccg   1920
caacccgacc gccattgctg aagcttcaat caagcagacc taaggaatga tcggatgcat   1980
tgcagggcac cgggaagaag aagtttgagc ggctgctcaa gagcgtggag gagaagttcc   2040
cgagcaaggt gagggccgtg gtcaggttca acgcgccgct ggctcaccag atgatggccg   2100
gcgccgacgt gctcgccgtc accagccgct tcgagccctg cggcctcatc cagctccagg   2160
ggatgcgcta cggaacggta aacgccgcct cctccttcct gccgattcct tatctccccg   2220
cgtatccatg gccatgaccg aagtttcttt caaatttgca gccgtgcgcg tgcgcgtcca   2280
ccggcgggct cgtcgacacg atcatggagg gcaagaccgg gttccacatg gccgccctca   2340
gcgtcgacgt aggctcgtcg atcccttgtg taaattcttc attttgttca tcctgggagc   2400
tcaggcagat catgaaatgg tttccttttt cctcttggtg gccagtgcaa cgtggtggag   2460
ccggccgacg tgaagaaggt ggtgaccacc ctgaagcgcg ccgtcaaggt cgtcggcacg   2520
ccagcctacc atgagatggt caagaactgc atgatccagg atctctcctg gaaggtaagt   2580
cgtctctggt ctggtttagg atgcattttc cagaacaact aagagttgag actacaatgg   2640
tgctcgtgct cgatgcatcc attaatggtg gcttgcgcat atggtgcagg gccagccaa    2700 gaactgggag gacgtgcttc tggaactggg ggtcgagggg agcgagccag gggtcatcgg   2760
cgaggagatt gcgccgctcg ccatggagaa cgtcgccgct ccctgaagag aggaaaga    2818
```

<210> SEQ ID NO 10
<211> LENGTH: 605
<212> TYPE: PRT
<213> ORGANISM: Tviticum aestivum L.

<400> SEQUENCE: 10

```
Met Ala Ala Leu Val Thr Ser Gln Leu Ala Thr Ser Gly Thr Val Leu
1               5                   10                  15

Gly Ile Thr Asp Arg Phe Arg Arg Ala Gly Phe Gln Gly Val Arg Pro
            20                  25                  30

Arg Ser Pro Ala Asp Ala Pro Leu Gly Met Arg Thr Thr Gly Ala Ser
        35                  40                  45

Ala Ala Pro Lys Gln Gln Ser Arg Lys Ala His Arg Gly Thr Arg Arg
    50                  55                  60

Cys Leu Ser Met Val Val Arg Ala Thr Gly Ser Ala Gly Met Asn Leu
65                  70                  75                  80

Val Phe Val Gly Ala Glu Met Ala Pro Trp Ser Lys Thr Gly Gly Leu
                85                  90                  95

Gly Asp Val Leu Gly Gly Leu Pro Pro Ala Met Ala Ala Asn Gly His
                100                 105                 110

Arg Val Met Val Ile Ser Pro Arg Tyr Asp Gln Tyr Lys Asp Ala Trp
            115                 120                 125

Asp Thr Ser Val Val Ser Glu Ile Lys Val Ala Asp Glu Tyr Glu Arg
    130                 135                 140

Val Arg Tyr Phe His Cys Tyr Lys Arg Gly Val Asp Arg Val Phe Val
145                 150                 155                 160

Asp His Pro Cys Phe Leu Glu Lys Val Arg Gly Lys Thr Lys Glu Lys
                165                 170                 175

Ile Tyr Gly Pro Asp Ala Gly Thr Asp Tyr Glu Asp Asn Gln Leu Arg
            180                 185                 190

Phe Ser Leu Leu Cys Gln Ala Ala Leu Glu Ala Pro Arg Ile Leu Asp
    195                 200                 205

Leu Asn Asn Asn Pro Tyr Phe Ser Gly Pro Tyr Gly Glu Asp Val Val
    210                 215                 220

Phe Val Cys Asn Asp Trp His Thr Gly Leu Leu Ala Cys Tyr Leu Lys
225                 230                 235                 240

Ser Asn Tyr Gln Ser Ser Gly Ile Tyr Arg Thr Ala Lys Val Ala Phe
                245                 250                 255

Cys Ile His Asn Ile Ser Tyr Gln Gly Arg Phe Ser Phe Asp Asp Phe
            260                 265                 270

Ala Gln Leu Asn Leu Pro Asp Arg Phe Lys Ser Ser Phe Asp Phe Ile
    275                 280                 285

Asp Gly Tyr Asp Lys Pro Val Glu Gly Arg Lys Ile Asn Trp Met Lys
    290                 295                 300

Ala Gly Ile Leu Gln Ala Asp Lys Val Leu Thr Val Ser Pro Tyr Tyr
305                 310                 315                 320

Ala Glu Glu Leu Ile Ser Gly Glu Ala Arg Gly Cys Glu Leu Asp Asn
                325                 330                 335

Ile Met Arg Leu Thr Gly Ile Thr Gly Ile Val Asn Gly Met Asp Val
            340                 345                 350

Ser Glu Trp Asp Pro Ala Lys Asp Lys Phe Leu Ala Ala Asn Tyr Asp
    355                 360                 365

Val Thr Thr Ala Leu Glu Gly Lys Ala Leu Asn Lys Glu Ala Leu Gln
    370                 375                 380

Ala Glu Val Gly Leu Pro Val Asp Arg Lys Val Pro Leu Val Ala Phe
385                 390                 395                 400

Ile Gly Arg Leu Glu Glu Gln Lys Gly Pro Asp Val Met Ile Ala Ala
            405                 410                 415

Ile Pro Glu Ile Leu Lys Glu Glu Asp Val Gln Ile Val Leu Leu Gly
```

```
                420             425             430
Thr Gly Lys Lys Lys Phe Glu Arg Leu Leu Lys Ser Val Glu Glu Lys
            435             440             445

Phe Pro Ser Lys Val Arg Ala Val Val Arg Phe Asn Ala Pro Leu Ala
        450             455             460

His Gln Met Met Ala Gly Ala Asp Val Leu Ala Val Thr Ser Arg Phe
465             470             475             480

Glu Pro Cys Gly Leu Ile Gln Leu Gln Gly Met Arg Tyr Gly Thr Pro
                485             490             495

Cys Ala Cys Ala Ser Thr Gly Gly Leu Val Asp Thr Ile Met Glu Gly
            500             505             510

Lys Thr Gly Phe His Met Gly Arg Leu Ser Val Asp Cys Asn Val Val
        515             520             525

Glu Pro Ala Asp Val Lys Lys Val Val Thr Thr Leu Lys Arg Ala Val
    530             535             540

Lys Val Val Gly Thr Pro Ala Tyr His Glu Met Val Lys Asn Cys Met
545             550             555             560

Ile Gln Asp Leu Ser Trp Lys Gly Pro Ala Lys Asn Trp Glu Asp Val
                565             570             575

Leu Leu Glu Leu Gly Val Glu Gly Ser Glu Pro Gly Val Ile Gly Glu
            580             585             590

Glu Ile Ala Pro Leu Ala Met Glu Asn Val Ala Ala Pro
        595             600             605

<210> SEQ ID NO 11
<211> LENGTH: 2886
<212> TYPE: DNA
<213> ORGANISM: Tviticum aestivum L.

<400> SEQUENCE: 11
cctgcgcgcg ccatggcggc tctggtcacg tcccagctcg ccacctccgg caccgtcctc      60
ggcatcaccg acaggttccg gcgtgcaggt ttccagggcg tgaggccccg gagcccggcg     120
gatgcggctc tcggcatgag gaccgtcgga gctagcgccg ccccaacgca aagccggaaa     180
gcgcaccgcg ggacccggcg gtgcctctcc atggtggtgc gcgccaccgg cagcggcggc     240
atgaacctcg tgttcgtcgg cgccgagatg gcgccctgga gcaagaccgg cggcctcggc     300
gacgtcctcg ggggcctccc cccagccatg gccgtaagct agacagcacc actgtcttct     360
cataatgttc atcttgcagt tgcagccatg cctgccgtta caacgggtgg tgtgtccgtg     420
caggccaacg gccaccgggt catggtcatc tccccgcgct acgaccagta caaggacgcc     480
tgggacacca gcgtcgtctc cgaggtactt gaaccctacc cgcaacttta cgatcaaaa      540 ttcgcatgct cctgcacatt tctgcaggat cctactgact gactaactgg atctcgcaga     600
tcaaggtcgt tgacaagtac gagagggtga ggtacttcca ctgctacaag gcgggggtgg     660
accgcgtgtt cgtcgaccac ccgtgcttcc tggagaaggt gaccgatcgt cgtcgtggac     720
cgatcaagct agctcttcgt cgtctcaacc ttgataggca tggtgattga tttcagttgt     780
ttctgctggt tgcaatttcc aggtccgggg caagaccaag gagaagatct acgggcccga     840
cgccggcacg gactacgagg acaaccagca gcgcttcagc cttctctgcc aggcggcgct     900
ggaagtgccg aggatcctga acctcgacaa taaccctac ttttctgggc ctacggtaa      960 gatcaagatc aagcacgcct actagttcaa gctagagtgt gtgtaatctg aactctgaag    1020
aacttgatat tttcttgaga gagctggatg atcaccattt ttttttgtat ctgggtgccg    1080
tcgtcgtccc ttgttgcgcg ccgcgcaggg gaggacgtgg tgttcgtgtg caatgactgg    1140
```

-continued

```
cacacgggcc ttctggcctg ctacctcaag agcaactacc agtccaatgg catctacagg    1200
gccgcaaagg ttttgcatct tcttctcaaa ctatatatcc tctctgcatt catatgcatg    1260
catatcttgc tcttcattct gaaacaggca tatcaatttt gcggttcatt ctggcctgaa    1320
ttttacattg caacttcatt tcatggccag gtggcattct gcatccacaa catctcgtac    1380
cagggccgct tctccttcga cgacttcgcg cagctcaacc tgcccgacag gttcaagtcg    1440
tccttcgact tcatcgacgg ctacgacaag ccggtggagg ggcgcaagat caactggatg    1500
aaggccggga tcctgcaggc cgacaaggtg ctgacggtga cccctacta cgcggaggag    1560 ctcatctctg gcgaagccag gggctgcgag ctcgacaaca tcatgcgcct cactgggatc    1620
accggcatcg tcaacggcat ggatgttagc gagtgggacc ccaccaagga caagttcctc    1680
gccgtcaact acgacatcac caccgtgagc aaccacacaa agatttcttc ctcttcttcc    1740
ggtgatcgct ggttctgggt gggttctcac gaacgaggca aagtgacagg cgttggaggg    1800
gaaggcgctg aacaaggagg cgctgcaggc cgaggtgggg ctgccggtgg accggaaggt    1860
gcccctggtg gcgttcatcg gcaggctgga ggagcagaag ggccccgacg tgatgatcgc    1920
cgccatcccg gagatcctga aggaggagga cgtccagatc gttctcctgg tacatcatcg    1980
agcccgcaac ccgaccgcca ttgctgaaac ttcgatcaag cagacctaag gaatgatcga    2040
atgcattgca gggcaccggg aagaagaagt tcgagcggct actcaagagc attgaggaga    2100
aattcccgag caaggtgagg gccgtggtca ggttcaacgc gccgctggct caccagatga    2160
tggccggcgc cgacgtgctc gccgtcacca gccgcttcga gccctgcggc ctcatccagc    2220
tccaggggat gcgctacgga acggtaaact tttccttctt gccaagtcct tacttcctga    2280
gcaatcatga gccatgccca tgaccgaagt tccttccaaa ttttcagccg tgcgcgtgcg    2340
cgtccaccgg cgggcttgtc gacacgatcg tggagggcaa gaccgggttc cacatgggcc    2400
ggctcagtgt cgatgtaagt tcatcaatct cttcaataaa ttcttcatct tgttcatcct    2460
gggagctcag gcagatcatc aaacgggttt cctttttcct cttggtggcc agtgcaacgt    2520
ggtggagccg gccgacgtga agaaggtggt gaccaccctg aagcgcgccg tcaaggtcgt    2580
cggcacgccg gcataccatg agatggtcaa gaactgcatg atacaggatc tctcctggaa    2640
ggtaagtcag tctctggtct ggtttaggat gcattttcca gaacaactaa gagttaagac    2700
tacaatggtg ctcttgttcg atgtatccat taatggtggc ttgcgcatat ggtgcagggg    2760
ccagccaaga actgggagga cgtgcttctg gaactgggtg tcgaggggag cgagccgggg    2820
gtcatcggcg aggagattgc gccgctcgcc atggagaacg tcgccgctcc ctgaagagag    2880
aaagaa                                                               2886
```

<210> SEQ ID NO 12
<211> LENGTH: 604
<212> TYPE: PRT
<213> ORGANISM: Tviticum aestivum L.

<400> SEQUENCE: 12

Met Ala Ala Leu Val Thr Ser Gln Leu Ala Thr Ser Gly Thr Val Leu
1               5                   10                  15

Gly Ile Thr Asp Arg Phe Arg Arg Ala Gly Phe Gln Gly Val Arg Pro
            20                  25                  30

Arg Ser Pro Ala Asp Ala Ala Leu Gly Met Arg Thr Val Gly Ala Ser
        35                  40                  45

Ala Ala Pro Thr Gln Ser Arg Lys Ala His Arg Gly Thr Arg Arg Cys
    50                  55                  60

```
Leu Ser Met Val Val Arg Ala Thr Gly Ser Gly Met Asn Leu Val
 65                  70                  75                  80

Phe Val Gly Ala Glu Met Ala Pro Trp Ser Lys Thr Gly Leu Gly
                 85                  90                  95

Asp Val Leu Gly Gly Leu Pro Pro Ala Met Ala Ala Asn Gly His Arg
                100                 105                 110

Val Met Val Ile Ser Pro Arg Tyr Asp Gln Tyr Lys Asp Ala Trp Asp
                115                 120                 125

Thr Ser Val Val Ser Glu Ile Lys Val Val Asp Lys Tyr Glu Arg Val
    130                 135                 140

Arg Tyr Phe His Cys Tyr Lys Arg Gly Val Asp Arg Val Phe Val Asp
145                 150                 155                 160

His Pro Cys Phe Leu Glu Lys Val Arg Gly Lys Thr Lys Glu Lys Ile
                165                 170                 175

Tyr Gly Pro Asp Ala Gly Thr Asp Tyr Glu Asp Asn Gln Gln Arg Phe
                180                 185                 190

Ser Leu Leu Cys Gln Ala Ala Leu Glu Val Pro Arg Ile Leu Asn Leu
            195                 200                 205

Asp Asn Asn Pro Tyr Phe Ser Gly Pro Tyr Gly Glu Asp Val Val Phe
            210                 215                 220

Val Cys Asn Asp Trp His Thr Gly Leu Leu Ala Cys Tyr Leu Lys Ser
225                 230                 235                 240

Asn Tyr Gln Ser Asn Gly Ile Tyr Arg Ala Ala Lys Val Ala Phe Cys
                245                 250                 255

Ile His Asn Ile Ser Tyr Gln Gly Arg Phe Ser Phe Asp Asp Phe Ala
                260                 265                 270

Gln Leu Asn Leu Pro Asp Arg Phe Lys Ser Ser Phe Asp Phe Ile Asp
            275                 280                 285

Gly Tyr Asp Lys Pro Val Glu Gly Arg Lys Ile Asn Trp Met Lys Ala
290                 295                 300

Gly Ile Leu Gln Ala Asp Lys Val Leu Thr Val Ser Pro Tyr Tyr Ala
305                 310                 315                 320

Glu Glu Leu Ile Ser Gly Glu Ala Arg Gly Cys Glu Leu Asp Asn Ile
                325                 330                 335

Met Arg Leu Thr Gly Ile Thr Gly Ile Val Asn Gly Met Asp Val Ser
            340                 345                 350

Glu Trp Asp Pro Thr Lys Asp Lys Phe Leu Ala Val Asn Tyr Asp Ile
            355                 360                 365

Thr Thr Ala Leu Glu Gly Lys Ala Leu Asn Lys Glu Ala Leu Gln Ala
370                 375                 380

Glu Val Gly Leu Pro Val Asp Arg Lys Val Pro Leu Val Ala Phe Ile
385                 390                 395                 400

Gly Arg Leu Glu Glu Gln Lys Gly Pro Asp Val Met Ile Ala Ala Ile
                405                 410                 415

Pro Glu Ile Leu Lys Glu Glu Asp Val Gln Ile Val Leu Leu Gly Thr
            420                 425                 430

Gly Lys Lys Lys Phe Glu Arg Leu Leu Lys Ser Ile Glu Glu Lys Phe
        435                 440                 445

Pro Ser Lys Val Arg Ala Val Arg Phe Asn Ala Pro Leu Ala His
        450                 455                 460

Gln Met Met Ala Gly Ala Asp Val Leu Ala Val Thr Ser Arg Phe Glu
465                 470                 475                 480

Pro Cys Gly Leu Ile Gln Leu Gln Gly Met Arg Tyr Gly Thr Pro Cys
```

```
                        485                 490                 495
Ala Cys Ala Ser Thr Gly Gly Leu Val Asp Thr Ile Val Glu Gly Lys
            500                 505                 510

Thr Gly Phe His Met Gly Arg Leu Ser Val Asp Cys Asn Val Val Glu
        515                 520                 525

Pro Ala Asp Val Lys Lys Val Val Thr Thr Leu Lys Arg Ala Val Lys
    530                 535                 540

Val Val Gly Thr Pro Ala Tyr His Glu Met Val Lys Asn Cys Met Ile
545                 550                 555                 560

Gln Asp Leu Ser Trp Lys Gly Pro Ala Lys Asn Trp Glu Asp Val Leu
                565                 570                 575

Leu Glu Leu Gly Val Glu Gly Ser Glu Pro Gly Val Ile Gly Glu Glu
            580                 585                 590

Ile Ala Pro Leu Ala Met Glu Asn Val Ala Ala Pro
        595                 600

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
gcgtttaccc cacagagc                                                   18

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tttaccccac agagcacact c                                               21

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcgccataca gcaagtcata                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gttttcaccg ttcactggta                                                 20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
```
acgcgccata cagcaagtca ta                                          22

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gttattcatt tcttcggtac a                                           21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
tcttcggtac accattggct a                                           21

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
atttcttcgg tacaccattg gcta                                        24

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
gcgtattgga ttggctac                                               18

<210> SEQ ID NO 22
<211> LENGTH: 16
<212> TYPE: DNA
<213> ORGANISM: Artificial Sequence
<220> FEATURE:
<223> OTHER INFORMATION: primer

<400> SEQUENCE: 22
tgccctccag gtcgtg                                                 16

<210> SEQ ID NO 23
<211> LENGTH: 14
<212> TYPE: DNA
<213> ORGANISM: Artificial Sequence
<220> FEATURE:
<223> OTHER INFORMATION: Primer

<400> SEQUENCE: 23
tgccgcagca tgcc                                                   14

<210> SEQ ID NO 24
<211> LENGTH: 26
<212> TYPE: DNA
<213> ORGANISM: Artificial Sequence

```
<220> FEATURE:
<223> OTHER INFORMATION: Primer

<400> SEQUENCE: 24 ggggagctgaa attttattgc ttattg                                            26

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
tgattttgtg ttcattgact atgttgg                                            27

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tcgcggtgaa gagaacatgg                                                    20

<210> SEQ ID NO 27
<211> LENGTH: 6619
<212> TYPE: DNA
<213> ORGANISM: Triticum aestivum

<400> SEQUENCE: 27
gggggccgtt cgtacgtacc cgcccctcgt gtaaagccgc cgccgtcgtc gccgtccccc        60
gctcgcggcc attccccgg  cctgaccccg tgcgtttacc ccacagagca cactccagtc       120
cagcgcagca ctggccgcgc gcgccgccgg gaagaaggac gcgagggtcg acgacgacgc       180
cgcgtccgcg aggcagcccc gcgcacgccg cggtggcgcc gccaccaagg tagttggttc       240
gttatgactt gctgtatggc gcgtgcgcct cgagatcagc tcacgaattg tttctacaaa       300
acgcacgcgc tcgtgtgcag gtcgcggagc ggagggatcc cgtcaagacg ctcgatcgcg       360
acgccgcgga aggtggcgcg ccggcaccgc cggcaccgag gcaggacgcc gcccgtccac       420
cgagtatgaa cggcacgccg gtgaacggtg agaacaaatc taccggcggc ggcggcgcga       480
ccaaagacag cgggctgccc gcacccgcac gcgcgcccca tccgtcgacc cagaacagag       540
taccagtgaa cggtgaaaac aaagctaacg tcgcctcgcc gccgacgagc atagccgagg       600
tcgtggctcc ggattccgca gctaccattt ccatcagtga caggcgccg  gagtccgttg       660 tcccagccga gaagccgccg ccgtcgtccg gctcaaattt cgtggtctcg gcttctgctc       720
ccaggctgga cattgacagc gatgttgaac ctgaactgaa gaagggtgcg gtcatcgtcg       780
aagaagctcc aaacccaaag gctctttcgc cgcctgcagc ccccgctgta caagaagacc       840
tttgggactt caagaaatac attggcttcg aggagcccgt ggaggccaag gatgatggct       900
gggctgttgc agatgatgcg ggctcctttg aacatcacca gaaccatgat tccgacctt       960 tggcagggga gaacgtcatg aacgtggtcg tcgtggctgc tgaatgttct ccctggtgca      1020
aaacaggcat ggacattacc tcttcagtct ctcttcccgt tgttcataaa actttgctcg      1080
aatcactcat aagaacaaac attgtgttgc ataggtggtc ttggagatgt tgcgggtgct      1140
ctgcccaagg ctttggcaaa gagaggacat cgtgttatgg tactgcaggc tttcacttaa      1200
ctctgttgag tccatatgtt cgaataatat cagtgattgg cataatgtta ttaagtgcaa      1260
```

```
gacatgaaag tgttcttctg ttagagtatt tcatagccaa ccctggaggt taggttgttg    1320
gggcctactg ggtgcgggag ggggtttgca aaaagtggtg gttagcagtc ggatttcaca    1380
aataaggagg ctgataacca cgccatcagt gaagggaatg agtgtcgggt acccgatcga    1440
ccgttttgcc cgacgtcagg tttacctgcc ctgtagatcc gaataagtag ttcctatcct    1500
cagttaagta ccaaatatcg ccagcacccg tgtgtgtatt tatagtactg gatgatcaat    1560
ttatcaacat ttccggttaa tggttgctat catattcact gtaattgtta gtaaacagtg    1620
gatgtttgta atgtagatga tggctaaatg tatgttgtca agctttcatt ttaaagaaaa    1680
ttttattggg agctagtttt cgggtttggt tagagccacc aaaacccag aattttttggg    1740 agttggcttg tgacagaggg ttttggggag ttaactttcg ggattcagtt agagacgctc    1800
ttactagttc cagtaaagag taaactattt tctgcagtca tcccaattgt tctgtagaaa    1860
ttaaaagtag aaaatagttg tggtatcata taaaccatat attattcaaa atctagaatc    1920
atggacttgg ctagactttg atgatctgaa attttaaatt tgatgataat tgagaaatga    1980
tcctttctat cttaggttgt ggtaccaagg tatggggact atgaggaagc ctacgatgtc    2040
ggagtccgaa aatactacaa ggctgctgga caggtaagcg aaaatgcaat caaaggggag    2100
ctgaaatttc aatgcttact atcataataa atcaatttta agtaaaaaaa tttgtcctgc    2160
aggatatgga agtgaattat ttccatgctt atatcgatgg agttgatttt gtgttcattg    2220
acgctcctat cttccgacac cgtcaggaag acatttatgg gggcagcaga caggttaatt    2280
ttctatatgt tggtgtttga ttgcactgat aaactgagaa taagccaagg cctactgact    2340
ggcatatgat tacacatttt attttttcag gaaattatga agcgcatgat tttgttctgc    2400
aaggccgctg tcgaggtatc ctctccaact caattgacaa cctattacca ctatacaatt    2460
atgtgtatgc atgtatttca acagatacgt aatctcccct gtgaagtgta tatatactaa    2520
taacatttca atacctcaca tgcacatttg gtcaagcgtt atgatttaac ttctgataat    2580
ctattgcact gatgaacaat aatattgatg atccttgtta cttcatcgtt atgtttatgt    2640
tctcttcacc ggcgcattga ttttggaaat agcatttcca cctgccacaa acaataatat    2700
atactcctac tttcatccaa tgtagatatt ttcgcacttg gcatatcatc ccattaaata    2760
ttattggtcc atcatttta ttcctctata atttgcaggt tccttggcac gttccatgcg    2820
gcggtgtccc ttatggggat ggaaatctgg tgtttattgc aaatgattgg cacacggcac    2880
tcctgcctgt ctatctgaaa gcatattaca gggaccatgg tttgatgcag tacactcggt    2940
ccattatggt gatacataac atcgcgcacc aggttccttt tctcctaatc ttgttttttc    3000
tctagtctct actattcact ccacattgtt tgaggaaact aaaggggttg caaaattatg    3060
atggcttatg aaagttatgg aggtaaatgc atcagtggtg cttgaacttg tcacgcatgt    3120
tcactttggt gcttacagtt gtagactacg gaaaactggt gcaaaaactt ggctattgtg    3180
tgcaatacgg tgtattttcc gtatgtaggg tcaaatgttg cctatgtggc attgtattcc    3240
cgtctataga tgttagaccg tgcctacatc gccattgggc ccacacactc cctattacat    3300
gtgggaccca cttgtcagcc tatgacataa ataaatgaa aatttataat aaaaatgatg    3360
gcctggggtc ttgaaaatgg gacctcgcag gtatgccgct agccagcacg ccctaatcat    3420
taatccccta tgcacttcag tatgtgtgtg tctgtgtgtg gagtcggggg ggggggggg    3480 gtatgtattc ttatatcctt tgctctaagg ctatcattgg cgtgctagca ccgccgggtc    3540
tccatcaaca ccgacatcat ccacgacccc atccagctct tcctcaacaa gcccacctcc    3600
agcctcaact cgggcagcac cttcatggtg gcctaggtgc tctgcaccat cgctcgaagt    3660
```

```
ggcaacgtcg ttgtcatgac catccaccaa cccaacacgc aaaatcctca acatcatttg   3720
acagtgagca tgcccctctt gtcatttccc cctcatacce aaacctgtct cgataaccct   3780
tggagctgca caagttgtga ccatcgcctg cgtcgctgca caacgcctga cctagccgga   3840
ccattataga agcctgcctt gggagcccat acctcctgc atcctcct ctttccccat     3900 agaccgtgcc gccatcgcaa atcgacttct cctctcctcc ttctcctgct ctggccgttt   3960
tccccgccgc gaagctgcaa tccatggcga gttggccatg ccctattcc ccaattgctc    4020 gcactaggag gtcctccttg aagcctagca ccttttcccc tcactaattg caagttgggg   4080
agcccctcac gagctcccta cattggccgt agtcgcctgc cgcctcaact ctggtccaga   4140
cctcgttccc gtggcctcga cgacatctcc tcgacctccc attccacacg cggcctggag   4200
aggatcaccg catgttcatc catccgaccc gaatcatcat agaaccaacg ccagagaggt   4260
catcccgacg acgtcgcact gttcctctat ttcccccaag ctgtgtcgcg tcataatata   4320
agacgggctt gtttgtatct ctaggggtca tcggttcaa tggctagctc atgcatggac    4380
ctgactttag gtcccaggtt cgaaccccg cgtgcacata atttatttgc tatttatttc    4440
tcctatctac taataagtgg gacccacaca tcatactaag cccttttgt ctcttgcctg    4500 ctgataagtg ggacccacac gcaatactta gccagagaga gaacatgagc ttgttggtgc   4560
cgcgttggca agccacgcca gcagtcttaa cggctacaaa cagaggatat ggtgtcacat   4620
caacgtgcag agcgtttacg aatggaaagt gtactatatg cacacaagag ccagagccag   4680 gttttttgcac cagttttttg tattctacaa ctgcgagcac caaagtgtac atgccgaacc   4740
aaagtgaaca cggcgagtcc attctttttct ggtacgatgg gtggctcaaa gacacccaa   4800 tagaagctat cacctcggac attgccaatt gggtgccgaa ctacattaaa gtggcaaggt   4860
cagttgattg cgctatgtgt tggatcaggg acataaacga ttccataaat attgcaatgt   4920
tcattcaaat tcttaacatt tgcgaggcgc ttcatgattt ccatctccct catatcagag   4980
acatttggtc gtgtacacta aatttctcag gtcacttctc gtctaaatcc gcatatgtag   5040
ctcacttcaa tgacttgact ttggtccagc taacgccatt tggcgctctt gggccccttt   5100
gcgtagcaat ttttcatat ggctcgctcc gcgcaatagg atttggatca cgggcagacg    5160
cgctagatga ggtcttccac acaatgaaca ttgcgttctt tgctctgctc ttccagaaga   5220
cacttgtgat tttattacga gttgtgccat agatgccggt gggtttcagc taggaacagg    5280
gtgtcacctt cggacaagaa gaagttgcat agtttggtcg tcttaactgc ttggtcgatt   5340
tggaaggagc acaacaacag tctttgaagg caaagctaat tcccctcgatc aagttattag   5400 acggatcaaa tgtggtacag tgccatggct agttgcttgg agtcacttt aagctaggtc    5460 gcttgccatc acgctttgtg ttaagcgctt ggggtcgctt ttgctcaatt tgtatttgt    5520 tgttatgtgt ttttagttat gtagcctgaa cttctggac ttagttttt cctctataat    5580 gatcacatgc tttggtcagt tattcctttc ttgggtactc cgttgggcta attctttctc   5640
ttgattgatg ttgtatatgc agggccgtgg cccagtagat gaattcccgt tcaccgagtt   5700
gcctgagcac tacctggaac acttcagact gtacgaccc gtgggtggtg agcacgccaa    5760
ctacttcgcc gccggcctga agatggcgga ccaggttgtc gtggtgagcc ccgggtacct   5820
gtgggagctc aagacggtgg agggcggctg ggggcttcac gacatcatac ggcagaacga   5880
ctggaagacc cgcggcatcg tcaacggcat cgacaacatg gagtggaacc ccgaggtgga   5940
cgtccacctc cagtcggacg gctacaccaa cttctccctg agcacgctgg actccggcaa   6000
gcggcagtgc aaggaggccc tgcagcgcga gctgggcctg caggtccgcg ccgacgtgcc   6060
```

-continued

```
gctgctcggc ttcatcggcc gcctggacgg gcagaagggc gtggagatca tcgcggacgc      6120
catgccctgg atcgtgagcc aggacgtgca gctggtcatg ctgggcaccg gccgccacga      6180
cctggagagc atgctgcggc acttcgagcg ggagcaccac gacaaggtgc gcgggtgggt      6240
ggggttctcc gtgcgcctgg cgcaccggat cacggcgggc gccgacgcgc tcctcatgcc      6300
ctcccggttc gagccgtgcg ggctgaacca gctctacgcc atggcctacg caccgtccc      6360 cgtcgtgcac gccgtcggcg ggctgaggga caccgtgccg ccgttcgacc ccttcaacca      6420
ctccggcctc gggtggacgt tcgaccgcgc cgaggcgcac aagctgatcg aggcgctcgg      6480
gcactgcctc cgcacctacc gggactacaa ggagagctgg aggggcctcc aggagcgcgg      6540
catgtcgcag gacttcagct gggagcatgc cgccaagctc tacgaggacg tcctcctcaa      6600
ggccaagtac cagtggtga                                                    6619

<210> SEQ ID NO 28
<211> LENGTH: 6986
<212> TYPE: DNA
<213> ORGANISM: Triticum aestivum

<400> SEQUENCE: 28
gggggccgtt cgtacgtacc caccctcgt gtaaagccgc cgccgtcgtc gccgtccccc        60
gctcgcggcc atttcctcgg cctgaccccg tgcgtttacc ccacacagag cacactccag      120
tccagtccag cccactgccg cgctactccc cactcccact gccaccacct ccgcctgcgc      180
cgcgctctgg gcggaccaac ccgcgcatcg tatcacgatc acccaccccg atcccggccg      240
ccgccatgtc gtcggcggtc gcgtccgccg cgtccttcct cgcgctcgcg tccgcctccc      300
ccgggagatc acggaggagg acgagggtga gcgcgtcgcc acccccacac ggggctggca      360
ggttgcactg gccgccgtcg ccgccgcagc gcacggctcg cgacggagca gtggccgcgc      420
gcgccgccgg gaagaaggac gcggggatcg acgacgccgc gcccgcgagg cagccccgcg      480
cactccgcgg tggcgccgcc accaaggtag ttagttatga ccaagttatg acgcgtgcgc      540
gcgccttgag atcatcgtcg tctcgctgac aaattgttta tacaaaacgc acgcgcgcgc      600
gtgtgtgcag gttgcggagc ggagggatcc cgtcaagacg ctcgatcgcg acgccgcgga      660
aggtggcgcg ccgtccccgc cggcaccgag gcaggaggac gcccgtctgc cgagcatgaa      720
cggcatgccg gtgaacggtg aaaacaaatc taccggcggc ggcggcgcga ctaaagacag      780
cgggctgccc gcacccgcac gcgcgcccca gccgtcgagc cagaacagag taccggtgaa      840
tggtgaaaac aaagctaacg tcgcctcgcc gccgacgagc atagccgagg tcgcggctcc      900
ggatcccgca gctaccattt ccatcagtga caaggcgcca gagtccgttg tcccagccga      960
gaaggcgccg ccgtcgtccg gctcaaattt cgtgccctcg gcttctgctc ccgggtctga     1020
cactgtcagc gacgtggaac ttgaactgaa gaagggtgcg gtcattgtca agaagctcc     1080 aaacccaaag gctctttcgc cgcctgcagc acccgctgta caacaagacc tttgggactt     1140
caagaaatac attggtttcg aggagcccgt ggaggccaag gatgatggcc gggctgttgc     1200
agatgatgcg ggctccttcg aacaccacca gaatcacgat tccggccctt tggcagggga     1260
gaacgtcatg aacgtggtcg tcgtggctgc tgaatgttct ccctggtgca aaacaggcat     1320
ggacattacc tcttcagtgt ctttttttctc tctgttcata aaacctggct tgaattactc     1380
ataagaacaa acgttgtgtt gcataggtgg tcttggagat gttgccggtg ctttgcccaa     1440
ggctttggcg aagagaggac atcgtgttat ggtaccacat gctttcattt aactctgttg     1500
aatccatatg ttcgaataat atcagtgagc agtataatgt tattaagtgc aagacatgaa     1560
```

```
agtgttcttc tgttatagag tatttcatag ccaaccctgg aggttaggtt gttggggcct    1620
actgggtgtg ggaggggggtt tgaaaaaagt gttggttagc agtcggattt cacaaagaac    1680
gctgataacc acgccatcag tgaagggaat gaatgtcggg tacccgatcg accgttttgc    1740
ccgacgtcag gtttacccgc cctgtaggtc cgaataagta gttcctatcc tcagttaagt    1800
accaaatatc ggcagcgccc gtgtgtgtat ttatagtact ggatgatcaa tttatcaaca    1860
ttttcagtta atggttgcta tcatattcac tgtaattgtt agtaaacagt ggatgtttgt    1920
aatgtagatg atggctaaat gtatgttgtc aagctttcat ttcaatgcaa ttttttattgg   1980 gagctagttt tggggttcgg ttagagccac caaaaccccca gaatttctgg gagttggctt   2040
gtgagagagg gttttggcga gttgactttc gggattcagt tagagacgct cttactagtt    2100
ccagtaaaga agtaaactat tttctgcaga catcccaatt attctgtaga aattagaagt    2160
agaaaatagt tatggtatca tataaccata tattattcaa aatctagaat catggacttg    2220
gctagacttt gatgatctga aatttttaaat ttgatgataa ttgagaaatg atcctttcta   2280
tcttaggttg tggtaccaag gtatggggac tatgaggaag cctacgatgt cggagtccga    2340
aaatactaca aggctgctgg acaggtaagc gaaaatgcaa tcaaggggga gctgaaattt    2400
caatgcttac tatcataata aatcaatttt aagtgttttt ttttgtcctg caggatatgg    2460
aagtgaatta tttccatgct tatatcgatg gagttgattt tgtgttcatt gacgctcctc    2520
tcttccgaca ccgccaggaa gacatttatg ggggcagcag acaggttaat cttctatatg    2580
ttggtgtttg attgcactga taaactgaga acaagccaag gcctactgac cggcatatga    2640
ttacacattt tatttttca ggaaattatg aagcgcatga ttttgttctg caaggccgct     2700
gtcgaggtat cctctccaac tcaattgaca acctattaca actatacaat tatgtgtatg    2760
catgtatttc aacagatacg taatctcttg tgaagtgcat atatactaac aacatttcaa    2820
taccttacat gcacatttgg tcaagcgtta tgatttaact tctaataatc tattgcactg    2880
atgaacaatt atcttgatga tccttggtac ttcatcgtta tgtttccatg ttctcttcac    2940
cgattgattt ggaaatagca tttccacctg ccacaaacaa taatatacac tcctactttc    3000
atccaatgta gatattttcg cacttggcat atcatcccat taaatattat tggtccatca    3060
tttttattcc tctataattt gcaggttcca tggcacgttc catgcggcgg tgtcccttat    3120
ggggatggaa atctggtgtt tattgcaaat gattggcaca cggcactcct gcctgtctat    3180
ctgaaagcat attacaggga ccatggtttg atgcagtaca ctcggtccat tatggtgata    3240
cataacatcg ctcaccaggt tccttttctc caaatcttga ttttttctcta gtctctacta   3300 tttactccac attgtttgag gaaactaaac gggttgcaaa attatgatgg cttatgaaag    3360
ttatagtctt atataggtaa atgcaccagt ggtgcttgca cttgtcacgc gtgttcactt    3420
tggtgcttac agttgtagac aataaaaaac tagtgcaaaa acttggctgt tgtgtgcaat    3480
acggtgcatt ttccgtatgt aggagtcaaa tattgcctgt gtggcattgt attcccgtct    3540
atagctgtta gaccatgcct acgtcgccat tgggcccaca caccctctat tacatgtggg    3600
ccccacttgt cagcctatga cataaataaa tggaaattta taatgaaaat gatggcctgg    3660
ggtcttgaaa atgggccgtc gcaggtatgc tggtagccag catgccctaa tcattaatcc    3720
ccctatgcac ttcatgtctt tgtgtatgtgt gtgtgggaaa gggggggggt atgtatgctt    3780
atgcttatat cctttgctcc aaggctgcca tcctcaacaa gcccacctcc agcttcaaca    3840
cggccagcgc cttcatgatg gcccaggtgc tccgcaccat cgatcgaagc ggcaacgtcg    3900
tcgtcacgac catccaccaa cccaacgcac aaaatcctca ggctccgttc ggtacggagg    3960
```

```
aagagaaaat gcaggaaaaa acaacttcat gggaacaagg tttggtgaac agtaaaaaca    4020
tgtggaatct gaaaatgtag gtaccagaaa aaccggcctg ttcggtttgc aggaaaaagc    4080
atacttgcag cagcactgtt tggccctttc cagtgtaagg ctaaccatag tgggagtaac    4140
ataactaata ttatgtactt ggaactcaca acatgcttta tgtggcaggc aattaaagaa    4200
gagagagaga gtcatagtaa catagttaga taccgtatca taataaatat tatgttacta    4260
tgtgtcatgc atgacaataa atgagaccat ctgtgatact acgttatgat attatgcact    4320
atagatgtag tatcatacac tagtatcata tgcatgatac tagtgtatgt tactccccac    4380
tatgaccagc ctaacgaggg gatgggcatc agtagtgatt accagttttt attatttttt    4440
attcggctgg acgccctact cttgtggtgc gtagcgaaaa aaggcagtgc tagcttcggg    4500
actccgcgag cacatgaggt tctaccggat tttagatttc ctataaaaag tacaggctca    4560 cgcaacttttt caatggaaca gaccatcaag attcctttga accgaacgca ctgcatgcaa    4620
gaattccaat gaaaaacgag ccgtcaaatg ttcctgcgaa tttcctctat accgaacaga    4680
ccctcaacat cctcaaatag tgagcatgcc cctcttgtcc tttcccccctc gtacccaaac    4740 gccatttggc gctcttggtg ttggatcatt tgcctcgggc atttgccaat ttggcgccga    4800
accatattaa agctatgact acttggtgtt ggatcaggga cgcaaagaat cccataaata    4860
ttgcaacgtt cattcaaatt cttaacattt gcgaggcgct tcatgatttc catctccgtc    4920
aggtctgaga catttggtcg tgtacactaa atttctcagg tcacttctcg tctaaatccg    4980
catatgtagc tcacttcaat gacttgcctt tggtctagct aacgccattt ggcgctcttg    5040 ggccccccttg cttagcaaat ttttcatatg gctcgcactg cgcaagagga tttagatcac    5100
gggcagacgc gctagacgag gtcttccgca caatgaacat tgcgttcttt gctctgctct    5160
tcccggagac acttgtgatc ttattacgag ttgtgccatt tcaaacatct gtctctccat    5220
ggtcgctcca gccatagatg ccttgttctc tgaatggtgg gtttcagcta ggaacagggt    5280
gccaccttcg acaagaagtt gcatagtttg gtcgtcttga ctgcttggtc gatttggaag    5340
gaacgcaaca taagagtctt tgaaggcaaa gctaatttct ttgatcaagt tattagccag    5400
atcaaatgtg atgtattcta ctggtacaag gccggggcta tttgctttga gtcacttttt    5460
agctaaggcc gcttgggcta agcgcttggg gtcgttttttg ctcaactgta gcctgaactt    5520
tctggacttt gtaattttttt ttatcctcta taatgatcac atacagctct cctgcatggt    5580
tcgaaaggaa aaaatgtgaa catgtgtggc aagtttaagc acaacccgtg catttacctc    5640
aaagttatac aacactgaca tgctgaatta cattttttttt gaggatctga catgccgaat    5700
tacatgcttt ggacagttat tcatttcttc ggtacaccat tggctaatta tttctcttga    5760
cagttgctga attagtacat gctttggtcg cagttattcc tttgttcggt actctgttgg    5820
gctaattatt tctcttgatt gatgttgcat gcagggccgt ggcccagtag atgagttccc    5880
gttcaccgag ttgcctgagc actacctgga acacttcaga ctgtacgacc ccgtgggtgg    5940
tgaacacgcc aactacttcg ccgccggcct gaagatggcg gaccaggttg tcgtcgtgag    6000
cccggggtac ctgtgggagc tgaagacggt ggagggcggc tgggggcttc acgacatcat    6060
acggcagaac gactgaaaga cccgcggcat cgtgaacggc atcgacaaca tggagtggaa    6120
ccccgaggtg gacgtccacc tcaagcagtg gcgtagccaa tccaatacgc cagggtggtc    6180
cattgataga aacatttaca taagattatt tatttttttaa agaaatactt ttttactgca    6240
ctgtacataa gctatggaga aattccaggg tggtccatgg accaccctgg cccaccccta    6300
gctacgccac tgacctcaag tcggacggct acaccaactt ctccctgggg acgctggact    6360
```

```
ccggcaagcg gcagtgcaag gaggccctgc agcgggagct gggcctgcag gtccgcggcg    6420
acgtgccgct gctcggcttc atcgggcgcc tggacgggca aagggcgtg gagatcatcg     6480 cggacgcgat gccctggatc gtgagccagg acgtgcagct ggtcatgctg ggcaccgggc    6540
gccacgacct ggagggcatg ctgcggcact tcgagcggga gcaccacgac aaggtgcgcg    6600
ggtgggtggg gttctccgtg cggctggcgc accggatcac ggccggcgcc gacgcgctcc    6660
tcatgccctc ccggttcgag ccgtgcggac tgaaccagct ctacgccatg gcctacggca    6720
ccgtccccgt cgtgcatgcc gtcggcgccc tgagggacac cgtgccgccg ttcgaccccet   6780 tcaaccactc cgggctcggg tggacgttcg accgcgcaga ggcgcagaag ctgatcgagg    6840
cgctcgggca ctgcctccgc acctaccggg actacaagga gagctggagg gggctccagg    6900
agcgcggcat gtcgcaggac ttcagctggg agcatgccgc caagctctac gaggacgtcc    6960
tcgtcaaggc caagtaccag tggtga                                         6986
```

<210> SEQ ID NO 29
<211> LENGTH: 6946
<212> TYPE: DNA
<213> ORGANISM: Triticum aestivum

<400> SEQUENCE: 29

```
gggggccgtt cgtacgtacc cgcccctcgt gtaaagccgc cgccgtcgtc gccgtccccc      60
gctcgcggcc atttcttcgg cctgaccccg ttcgtttacc cccacacaga gcacactcca     120
gtccagtcca gcccactgcc accgcgctac tctccactcc cactgccacc acctccgcct     180
gcgccgcgct ctgggcggac caacccgcga accgtaccat ctcccgcccc gatccatgtc     240 gtcgcggtc gcgtccgccg catccttcct cgcgctcgcg tcagcctccc ccgggagatc      300
acgcaggcgg gcgagggtga gcgcgcagcc accccacgcc ggggccggca ggttgcactg     360
gccgccgtgg ccgccgcagc gcacggctcg cgacggagct gtggcggcgc tcgccgccgg    420
gaagaaggac gcggggatcg acgacgccgc cgcgtccgtg aggcagcccc gcgcactccg    480
cggtggcgcc gccaccaagg tagttagtta tgaccaagtt atgacgcgtg cgcgcgcctc    540
gagatcatcg tcgtctcgct cacgaattgt ttatttatac aaaacgcacg cccgcgtgtg    600
caggtcgcgg agcgaaggga tcccgtcaag acgctcgacc gcgacgccgc ggaaggcggc    660
gggccgtccc cgccggcagc gaggcaggac gccgcccgtc cgccgagtat gaacggcatg    720
ccggtgaacg gcgagaacaa atctaccggc ggcggcggcg cgactaaaga cagcgggctg    780
cccacgcccg cacgcgcgcc ccatccgtcg acccagaaca gagcaccggt gaacggtgaa    840
aacaaagcta acgtcgcctc gccgccgacg agcatagccg aggccgcggc ttcggattcc    900
gcagctacca tttccatcag cgacaaggcg ccggagtccg ttgtcccagc tgagaagacg    960
ccgccgtcgt ccggctcaaa tttcgagtcc tcggcctctg ctcccgggtc tgacactgtc   1020
agcgacgtgg aacaagaact gaagaagggt gcggtcgttg tcgaagaagc tccaaagcca   1080
aaggctcttt cgccgcctgc agcccccgct gtacaagaag accttgggaa tttcaagaaa   1140
tacattggtt tcgaggagcc cgtggaggcc aaggatgatg gccgggctgt cgcagatgat   1200
gcgggctcct ttgaacacca ccagaatcac gactccggac cttttggcagg ggagaatgtc  1260 atgaacgtgg tcgtcgtggc tgctgagtgt tctccctggt gcaaacagg catggacatt    1320 acctcttcag tctctcttcc tgttgttcat aaaactttgc tcgaattact cataagaaca    1380
aacattgtgt tgcataggtg gtctgggaga tgttgcgggt gctctgccca aggctttggc   1440
aaagagagga catcgtgtta tggtactaca agctttcatt taactctgtt gggtccatat    1500
```

```
gttcgaataa tatcagtgag tagtataatg ttattaagtg caagacatga aagtgttctt   1560
ttgtcatact ccctccgtaa attaatataa gagcgtttag attactactt tagtgatcta   1620
aacgctctta tagtagttta cagacggagt agagtatttc atagccaacc ctggaggtta   1680
ggttgctgag gcctactggg tgggggaggg ggtttgaaac aagtggtggt tagcagccag   1740
atttcacaaa gaaggaggct gataaccaca ccatcagtga aggaatgaat gtcgggtacc   1800
cgatcgaccg ttttgcccaa cgtcgggttt acccgcccta tagatccgaa taagtagttc   1860
ctatcttcaa ttaggtacca aatatcgcca gcgcccgtgt gtgtatttat actactggat   1920
gatcaattta tcaacatttc cggttaatgg tttctatcat attcactgta attgttagta   1980
aacagtagat gtttgtaatg tagatgatgg ataaatgtat gttgtcgagc tttcatttca   2040
atgcaatttt gattgggagc tagtttcgcg gttcggttag agccatcaaa accccagaat   2100
ttttgggagt tggcttgtga gagagggttt tggggagtta actttcggga ttcagttaga   2160
gacgctctta ctagttccag taaagagtaa actatttct gcaggcatcc caattattct    2220
gtagaaatta gaagtggaaa atagttatgg tatcatataa accatatatt attcaaaatc   2280
tagaatcatg gacttggcta gactttgata atctgaaatt ttaaatttga tgataattga   2340
gaaatgatcc tttctatctt aggttgtggt accaaggtat ggggactatg aagaagccta   2400
cgatgtcgga gtccgaaaat actacaaggc tgctggacag gtaagcaaaa atgcaatcga   2460
aggggagctg aaattttatt gcttattgtc ataataaatc aattttaag tgtttttttt     2520 gtcctgcagg atatggaagt gaattatttc catgcttata tcgatggagt tgattttgtg   2580
ttcattgact atgttggtgt ttgattgcac tgataaactg agaacaagcc aaggcctact   2640
gactggcata tgattacaca ttttattttt tcaggaaatt atgaagcgca tgattttgtt   2700
ctgcaaggcc gctgttgagg tatctctcca actcaattga caacctatta ccactataca   2760
attatgtgta tgcatgtatt tcaacagata cataatctct tgtgaagtgc atatatacta   2820
ataacatttc aataccttac atgcacattt ggtcaagcgt tatgatttaa cttctgataa   2880
tctattgcac tgatgaacaa ttatcttgat gatccttgtt acttcatcgt tatgtttcca   2940
tgttctcttc accgcgaatt gatttggaaa tagcatttcc acctgccaca aacaataata   3000
tacactccta ctttcatcca atttagatat tttcgtactt ggcatatcat cccattaaat   3060
attattggtc catcattttt attcctctat aatttgcagg ttccatggca cgttccatgc   3120
ggcggtgtcc cttatgggga tggaaatctg gtgtttattg caaatgattg gcacacggca   3180
ctcctgcctg tctatctgaa agcatattac agggaccatg gtttgatgca gtacactcgg   3240
tccattatgg tgatacataa catcgctcac caggttcctt ttctcctaat cttgattttt   3300
ctctagtctc tactatttac tccacattgt ttgaggaaac taaacgggtt gcaaaattat   3360
gatggcttat gaaagttata gtcttataga ggtaaatgca ccagtggtgc ttgaacttgt   3420
cacgcgtgtt cactttggtg cttacagttg tagactatga aaaacgggtg caaaaacttg   3480
ctgttgtgtg ccatacggtg cattttccgt atgtaggagt caaacgttgc ctatgtgggc   3540
attgtattcc cgtctatagc tgttagaccg tgcctacgtc gccattgggc ccacacactc   3600
tctatttaca tgtgggcccc acttgtcaac ctatgacata aataaatgga aatttataat   3660
aaaaatgatg gcctggggtc ttgaaaatgg gacctcgcag gtatgctggt agccagcacg   3720
ccctaaacat taatccccta tgcacttcat gtcttgtgta tgtgtgtgtc tgtgtgggga   3780 gggggggta tgtatgctta tatccttttgc tccaaggcta ccatcctcaa caagcccacc   3840
tccgcttcaa cacggccagc gccttcatga tggcccaggt gctccgcacc atcgctcaaa   3900
```

```
gcggcaacgt cgttgtcatg accatccacc aacccaacac acaaaatcct caacatccgc    3960
aaatagtgag catgcccctc ttgtcctttc ccctcgtacc caaacatgtc ttgataaccc    4020
ttggagctgc acaagttgtg accatcgcct gcgtcgcctc atagagcccg acctagccgg    4080
accgttatag aagcctactt gggagcccat acctccctgc acatcctcct ctttccccat    4140
agatcgtgcc gccatcgcaa accaacttct cctctccttc tcccactctg ccgtttccc     4200 ccgccgcgaa gctgcaatac atgccgagtt ggccatggcc ctattcccca attgctcgca    4260
ctaggaggtc ctcctctaag cctagcacct tttcccctca ccaattgcaa gttggggagc    4320
ccctcgcgag ctccctacgt cggctgcagt tgcctgccgc ctcaactctg atccagacct    4380
cgttcccgtg gcctcggcga catctcctcg acctcccatt ccacacgtgg cctggcgagg    4440
atcaccgcat gttcatccat gtgaaccgaa tcatcataga actaacaccg gagaggtcat    4500
cccgacggcg tcgcactgtt cctctattcc ccccaagccg tgtcgcgtca taatataaga    4560
cggacttatt tgtatccctt gggtcatcgg ttcaatggct atttctttct cctgtctact    4620
gataagtggg acccacacgc cacactaagc cctttctttc tcctacccgt tgataagtgg    4680
gacccacaca cagtacttag ccagagagag aacatgagct tgttggtgcc acgtcggcaa    4740
gccatgtcag cagtcttaac ggctacaaac aacggatatg gtgtcacgtg agcgtttacg    4800 aatgaaagt  gcatcatact gcatgcgaga gccagagcca ggttttttgca ccagttttct    4860 gtattttaca actgcgagca tcaaagtgta catatgccga accaaagtga acatggtgag    4920
tccattcttt tctggtgcgg tgggtggctc aaagacaccc caatagaagc tattgcctcc    4980
gacattgcca attcggtgcc gaaccatatt gaagtggtga ggtcagttgc ttgtgctatg    5040
actactaggt attggatgag ggacataaag gatctcataa atattgcaat gttcattcaa    5100
attcttaaca tttgcgaagc gcttcatgat ttccatctcc cctagatcag agacacttgg    5160
tcgtgtacac tgaatttctc aggtcgcttc tcgtctaaat ccgcatatgt agctcacttc    5220
aatgacttgc ctttggtcca gctaacgcca tttgcgtagc aaattttttca tatggctcgc    5280 tctgcgcaag aggatttgga tcacgggcag acgcgctaga caaggtcttc cgcacaatga    5340
acattgagtt ttttgatccg ctcttcccga agacacttgt gatcttatta cgagttgtgc    5400
catttcaaac atctgtctct ccatggtcgc cccagccata gatgccttgt tctctgaatg    5460
gtgggtttca gctaggaaca gggtgccacc ttcggacaag aagttgcgta gtttggtcgt    5520
cttaactgct tggttgattt ggaaggaaca caacaacagt ctttgaaggc aaagctaatt    5580
ccttcgatca agttattaga cggatcaagt gtgatgaatc ctactggtac aatgccgttg    5640
ctagttgctt ggagtcacta tttggctagg tcgcttgcca tcccgctctg tgctaagcgc    5700
ttggggtcgc ttttgctcaa tttgtatttt gttgttatgt gtttttagta atgtaacctg    5760
aactttctgg actaagtaga aaaaaattct cctccataat gatcacatac agttctcctg    5820
catggttcga aaaaaaaatg agaacatccg tggcaagttt aagcaccacc ggtgcatttt    5880
tacctcaaag ttatatacaa cactgacatg ccgaattaca tgctttggtc agttattcca    5940
ttcttcggta ctccgttggg ctaattcttt ctcttcatgt tgcatgcagg gccgtggccc    6000
tgtagatgaa ttcccgttca ccgagttgcc tgagcactac ctggaacact tcagactgta    6060
cgaccccgtg ggtggtgaac acgccaacta cttcgccgcc ggcctgaaga tggcggacca    6120
ggttgtcgtg gtgagccccg ggtacctgtg ggagctgaag acggtggagg gcggctgggg    6180
gcttcacgac atcatacggc agaacgactg gaagacccgc ggcatcgtca acggcatcga    6240
caacatggag tggaaccccg aggtggacgc ccacctcaag tcggacggct acaccaactt    6300
```

```
ctccctgagg acgctggact ccggcaagcg gcagtgcaag gaggccctgc agcgcgagct    6360
gggcctgcag gtccgcgccg acgtgccgct gctcggcttc atcggccgcc tggacgggca    6420
gaagggcgtg gagatcatcg cggacgccat gccctggatc gtgagccagg acgtgcagct    6480
ggtgatgctg ggcaccgggc gccacgacct ggagagcatg ctgcagcact tcgagcggga    6540
gcaccacgac aaggtgcgcg ggtgggtggg gttctccgtg cgcctggcgc accggatcac    6600 ggcggggggcg gacgcgctcc tcatgccctc ccggttcgag ccgtgcgggc tgaaccagct    6660
ctacgccatg gcctacgca ccgtccccgt cgtgcacgcc gtcggcggcc tcagggacac    6720
cgtgccgccg ttcgacccct tcaaccactc cgggctcggg tggacgttcg accgcgccga    6780
ggcgcacaag ctgatcgagg cgctcgggca ctgcctccgc acctaccgag acttcaagga    6840
gagctggagg gccctccagg agcgcggcat gtcgcaggac ttcagctggg agcacgccgc    6900
caagctctac gaggacgtcc tcgtcaaggc caagtaccag tggtga                   6946
```

The invention claimed is:

1. Wheat comprising a genome which does not express any of the proteins (a)-(f):
(a) Wheat Starch Synthase II-A1 Protein encoded by Wheat Starch Synthase II-A1 gene of SEQ ID NO:1;
(b) Wheat Starch Synthase II-B1 Protein encoded by Wheat Starch Synthase II-B1 gene of SEQ ID NO:3;
(c) Wheat Starch Synthase II-D1 Protein encoded by Wheat Starch Synthase II-D1 gene of SEQ ID NO:5;
(d) Granule Bound Starch Synthase A1 Protein encoded by Granule Bound Starch Synthase A1 gene of SEQ ID NO:7;
(e) Granule Bound Starch Synthase B1 Protein encoded by Granule Bound Starch Synthase B1 gene of SEQ ID NO:9; and
(f) Granule Bound Starch Synthase D1 Protein encoded by Granule Bound Starch Synthase D1 gene of SEQ ID NO:11.

2. Wheat comprising a genome which does not express any of the enzyme activities of the proteins (a)-(f):
(a) Wheat Starch Synthase II-A1 Protein encoded by Wheat Starch Synthase II-A1 gene of SEQ ID NO:1;
(b) Wheat Starch Synthase II-B1 Protein encoded by Wheat Starch Synthase II-B1 gene of SEQ ID NO:3;
(c) Wheat Starch Synthase II-D1 Protein encoded by Wheat Starch Synthase II-D1 gene of SEQ ID NO:5;
(d) Granule Bound Starch Synthase A1 Protein encoded by Granule Bound Starch Synthase A1 gene of SEQ ID NO:7;
(e) Granule Bound Starch Synthase B1 Protein encoded by Granule Bound Starch Synthase B1 gene of SEQ ID NO:9; and
(f) Granule Bound Starch Synthase D1 Protein encoded by Granule Bound Starch Synthase D1 gene of SEQ ID NO:11.

3. The wheat of claim 1, which contains 0.1% by mass or more of glucose and 0.1% by mass or more of maltose in a mature seed whose embryo has been removed.

4. The wheat of claim 2, which contains 0.1% by mass or more of glucose and 0.1% by mass or more of maltose in a mature seed whose embryo has been removed.

* * * * *